(12) United States Patent
Multhoff

(10) Patent No.: US 8,440,188 B2
(45) Date of Patent: May 14, 2013

(54) THERAPEUTIC AND DIAGNOSTIC ANTI-HSP70 ANTIBODIES

(75) Inventor: Gabriele Multhoff, Munich (DE)

(73) Assignee: Multimmune GmbH, Munich (DE)

(*) Notice: Subject to any disclaimer, the term of this patent is extended or adjusted under 35 U.S.C. 154(b) by 0 days.

(21) Appl. No.: 13/081,015

(22) Filed: Apr. 6, 2011

(65) Prior Publication Data

US 2012/0087931 A1 Apr. 12, 2012

Related U.S. Application Data

(63) Continuation-in-part of application No. 12/707,502, filed on Feb. 17, 2010, now abandoned, which is a continuation of application No. 10/581,960, filed as application No. PCT/EP2004/013854 on Dec. 6, 2004, now Pat. No. 7,700,737.

(30) Foreign Application Priority Data

Dec. 5, 2003 (EP) .................................. 03028144

(51) Int. Cl.
- *A61K 39/395* (2006.01)
- *G01N 33/53* (2006.01)
- *G01N 33/577* (2006.01)

(52) U.S. Cl.
USPC ................. 424/130.1; 435/7.21; 436/501

(58) Field of Classification Search .................. None
See application file for complete search history.

(56) References Cited

FOREIGN PATENT DOCUMENTS

| WO | WO 9116928 A1 | * 11/1991 |
| WO | WO 0222656 A2 | * 3/2002 |
| WO | WO 03/086383 | 10/2003 |
| WO | WO 2005/054868 | 6/2005 |

OTHER PUBLICATIONS

Payne, Progress in immunoconjugate cancer therapeutics. Cancer Cell 3:207-212, Mar. 2003.*
Stangl et al., Targeting membrane heat-shock protein 70 (Hsp70) on tumors by cmHsp70.1 antibody. Proc Natl Acad Sci USA. 108 (2):733-738, Jan. 11, 2011; Epub Dec. 27, 2010.*
Stangl et al.,In vivo imaging of CT26 mouse tumours by using cmHsp70.1 monoclonal antibody. J Cell Mol Med. 15(4):874-87, Apr. 2011; Epub Apr. 6, 2010.*
Botzler C et al, "Definition of extracellular localized epitopes of Hsp70 involved in an NK immune response," Cell Stress and Chaperones, Edinburgh, GB, vol. 3, 1998 pp. 6-11.
Multhoff G et al, "CD3-large granular lymphocytes recognize a heat-inducible immunogenic determinant associated with the 72-kD heat shock protein on human sarcoma cells," Blood, W.B. Saunders Philadelphia, VA vol. 86, Aug. 15, 1995, pp. 1374-1382.
Wei Yu-Quan et al, "Induction of autologous tumor killing bt heat treatment of fresh human tumor cells: Involvement of gamma-delta T cells and heat shock protein 70" Cancer Research,vol. 56 1996, pp. 1104-1110.

* cited by examiner

*Primary Examiner* — Ruixiang Li
(74) *Attorney, Agent, or Firm* — Casimir Jones SC

(57) ABSTRACT

Methods and compositions for the detection, prevention and treatment of infectious diseases, primary and metastatic neoplastic diseases, including, but not limited to human sarcomas and carcinomas are described. In particular, specific antibodies are provided, which are capable of binding an epitope of Hsp70 that is extracellularly localized on diseased tissue and cells, in particular on tumor cells and infected cells.

9 Claims, 19 Drawing Sheets

```
                        SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asn Leu Leu Gly Arg Phe Glu Leu
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Thr Lys Asp Asn Asn Leu Leu Gly Arg Glu Phe Leu Ser Gly
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Asn Gly Leu Thr Leu Lys Asn Asp Phe Ser Arg Leu Glu Gly
1               5                   10
```

THERAPEUTIC AND DIAGNOSTIC ANTI-HSP70 ANTIBODIES

CROSS REFERENCE TO RELATED APPLICATIONS

This application is a continuation-part of U.S. patent application Ser. No. 12/707,502, filed Feb. 17, 2010 (now abandoned), which is a continuation of U.S. patent application Ser. No. 10/581,960, filed May 14, 2007 (now U.S. Pat. 7,700,737, issued on Apr. 20, 2010), which is a U.S. National Stage Application under 35 U.S.C. 371 of PCT International Patent Application Serial No.: PCT/EP2004/013854, filed Dec. 6, 2004, which claims priority to European Patent Application Serial No.: EP 03 028 144.8, filed Dec. 5, 2003, each of which are herein incorporated by reference in its entirety.

FIELD OF THE INVENTION

The present invention relates to methods and compositions for the detection, prevention and treatment of infectious diseases, primary and metastatic neoplastic diseases, including, but not limited to leukemia, human sarcomas and carcinomas. In accordance with the present invention, the practice of the detection, prevention and treatment of infectious diseases and cancer is mediated and/or indicated by the presence and localization of certain tumor markers on the cell surface of diseased tissue or cells. In particular, the present invention relates to antibodies and antigen-binding molecules which are capable of binding to an epitope of heat shock protein Hsp70 that is localized extracellularly on tumor cells. Furthermore, the present invention relates to compositions comprising said antibodies and their use in methods of diagnosis and treating immune response related and other diseases including tumors. The present invention further concerns the use of an antibody capable of recognizing membrane-bound Hsp70 protein or a binding domain thereof for the detection and/or treatment of a tumor or an infectious disease.

BACKGROUND OF THE INVENTION

Heat shock proteins (Hsps) are highly conserved molecules mediating protection against lethal damage following various stress stimuli in prokaryotic and eukaryotic cells. Also under physiological conditions they support folding of non-native or misfolded proteins and prevent aggregation during proliferation and cellular differentiation (Hartl and Hayer-Hartl, Science 295 (2002), 1852-1858). The best characterized group of chaperones belong to the Hsp70 family. Like other stress proteins, Hsp70s are most efficient if they operate in concert with co-factors as cellular chaperone machineries. Together with J domain co-chaperones (i.e. Hsp40), they support protein folding and assist translocation across membranes (Pilon and Schekman, Cell 97 (1999), 679-682). Heat shock proteins (HSP) are also inducible by physiological processes including cell differentiation and development (Lindquist and Craig, Annu. Rev. Genet. 22 (1988), 631). Intracellular HSP functions not only as molecular chaperones, they are involved in antigen processing and presentation as well (DeNagel and Pierce, Immunol. Today 13 (1992), 86; Hartl et al., Nature 381 (1996), 571). HSP with a molecular weight of 70 and 90 kDa also have been shown to function as carrier proteins for immunogenic tumor-derived peptides that induce a T cell mediated immune response against cancer (Tamura et al., Science 278 (1997), 117; Schild et al., Current Opinion in Immunology 11 (1999), 109; Srivastava et al., Immunity 8 (1998), 657). Antigen presenting cells are key for the receptor mediated uptake of HSP-peptide complexes (Arnold-Schild et al., J. Immunol. 162 (1999), 3757). Several groups reported an unusual plasma membrane localization of HSP on tumor cells (Altmeyer et al., Int. J. Cancer 69 (1996), 340; Ferrarini et al., Int. J. Cancer 51 (1992), 613; Piselli et al., J. Biol. Regul. Homeost Agents 9 (1995), 55; Tamura et al., J. Immunol. 151 (1993), 5516). The inventors were the first who demonstrated that NK cells also have to be considered as relevant effector cells for the recognition of membrane-bound Hsp70 on tumor cells (Multhoff et al., Blood 86 (1995a), 1374; Multhoff et al., Int. J. Cancer 61 (1995b), 272; Multhoff et al., J. Immunol. 158 (1997), 4341; Botzler et al., Cancer Immunol. Immunother. 43 (1996a), 226; Botzler et al., Int. J. Cancer 65 (1996b), 633). With respect to these findings and due to the fact that normal cells lack expression of Hsp70, on the plasma membrane, one might speculate that Hsp70 acts as a tumor-selective recognition structure for NK cells. Antibody blocking studies revealed that Hsp70 is a relevant recognition structure for transiently plastic adherent NK cells (Multhoff et al., Blood 86 (1995a), 1374; Multhoff et al., Int. J. Cancer 61 (1995b), 272; Multhoff et al., J. Immunol. 158 (1997), 4341; Botzler et al., Cell Stress & Chaperones 3 (1998), 6).

It was recently demonstrated that proliferation and cytolytic activity of NK cells against Hsp70-expressing tumor cells could be stimulated with recombinant Hsp70 protein but not with Hsc70 or DnaK (Multhoff et al., Exp. Hematology 27 (1999), 1627). As target cells for the cytolytic activity of NK cells the tumor sublines CX+ and CX− with an identical MHC and adhesion molecule expression pattern that differ with respect to the capacity to express Hsp70 on the plasma membrane, were used (Multhoff et al., J. Immunol. 158 (1997), 4341).

As described above, the presence and localization of Hsp70 on the cell surface of diseased tissue or cells, in particular on tumor cells provides a valuable marker and target for therapeutic intervention. It is thus highly desirable to have antibodies or other binding molecules, which specifically recognize extracellular epitopes of Hsp70 on such tissue and cells.

Although several antibodies directed against Hsp70 are commercially available and have been described in the literature, these appear to be uncapable and/or unreliable in detecting membrane-bound Hsp70 on the surface of cells. The inventors tested a panel of these antibodies for the ability to detect plasma membrane bound Hsp70. Most of the tested antibodies were unsuitable for this task (SPA-820, Stressgen; H553220-clone7; BD Pharmingen; H5147 clone BRM-22; Sigma; 0A500 polyclonal, Dako; MS-482 clone W27, Neo-Markers), while others gave conflicting results.

The anti-Hsp70 antibodies from Affinity Bioreagents (MA3-006 and MA3-009) showed different specificities for different batches. Some batches were suitable for the detection of Hsp70 on the plasma membrane to some extent (Botzler et al., Cell Stress & Chaperones 3 (1998), 6) but recent batches showed no reactivity towards Hsp70 localized on the cell surface of tumor cells. Similarly, clone C92F3A-5 supplied by Stressgen Inc. as SPA-810 and by MBL, Japan, as SR-B810 has been described to react with cell surface localized Hsp70 on some occasions (Barreto et al., Cell. Immunol. 222 (2003), 97-104; Feng et al., Blood 100 (2002), 4108-4115) but the inventors were unable to repeat the reported results. In the report of Feng et al. cell surface Hsp70 was only detected in apoptotic cells, which may be due to antibodies entering the degrading apoptotic cells whose cell membrane was no longer intact and detecting intracellular Hsp70. The conflicting results of Baretto et al and other investigators might further be due to quality differences of the batches used for the respective experiments. Also there are no reports of binding cell surface Hsp70 so far for the MBL supplied antibody.

Loss of specificity or a change of specificity of a monoclonal antibody may also be due the hybridoma cell line producing said antibody not being derived from a single cell line. A mixture of two or more different hybridomas will produce a mixture of two or more monoclonal antibodies with different specificity. The ratio of the cells within the culture and thereby the ratio of the different monoclonal antibodies produced by them may vary during cultivation. Also, a particular hybridoma producing the antibody with the desired specificity might be lost from the mixture if the other hybridoma cells have an evolutionary advantage. A mixture of hybridomas in the culture can also result from mutations in certain cells leading to shifting specificities of the antibodies produced.

Thus, there is a need for a reliable source of anti-Hsp70 antibodies capable of detecting extracellular epitopes of Hsp70 and thereby enabling the specific detection and treatment of tumor cells or cells infected by a pathogen.

The solution to said technical problem is achieved by providing the embodiments characterized in the claims and described further below.

SUMMARY OF THE INVENTION

The present invention relates to the technical field of immunology and the treatment of diseases mediated and/or indicated by the presence and localization of certain tumor markers on the cell surface of diseased tissue or cells. In a first aspect, the present invention relates to an antibody or antigen-binding fragment thereof that binds to an epitope of Hsp70 that is localized extracellularly on tumor cells.

Although the combination of monoclonal antibodies (mAb) with standard therapies plays a pivotal role in the treatment of cancer (1-4), the therapeutic success of this strategy is limited by the restricted availability of tumor-specific antibodies. Therefore, one object of the present invention is the search for innovative tumor-specific target structures for tumor therapy and the inventors of the present invention revealed heat shock protein 70 (Hsp70-1, HspA1A #3303) [1], the major stress-inducible member of the 70 kDa heat shock proteins, as one such target. Both Hsp70 and gp96, an ER-resident member of the 90 kDa heat shock protein group (gp96, HspC3#7184), have been found on the plasma membrane of a variety of different human tumors [2-4]. During the studies of the present invention the inventors generated and characterized a mouse monoclonal antibody (mAb), termed cmHsp70.1, which specifically detects the cell surface localized Hsp70 on viable tumor cells with intact plasma membrane. The amino acid sequence of the Hsp70 molecule, which is exposed to the extracellular milieu of these tumors has been identified as being part of the 14-mer peptide TKDNNLLGRFELSG (SEQ ID NO: 2) (TKD) [5,6].

Screening of tumor biopsies and the corresponding normal tissues has indicated that primary diagnosed carcinoma samples, but none of the tested normal tissues, frequently exhibit an Hsp70 membrane-positive phenotype [7-9]. Moreover, an Hsp70 membrane-positive tumor phenotype has been associated with a significantly decreased overall survival in patients with lung cancer and lower rectal carcinomas suggesting that Hsp70 membrane-positivity might serve as a negative prognostic marker [10]. It has also been shown that the density of membrane Hsp70 on tumor cells can be further enhanced following therapeutic intervention such as radio- or chemotherapy [11].

The anchorage of Hsp70 protein in the plasma membrane of non-stressed tumors is enabled by the glycosphingolipid globoyltriaoslyceramide (Gb3) [12,13], which is frequently over-expressed in colorectal and gastric tumors and rarely found in the plasma membrane of normal cells. Following stress, elevated levels of Hsp70 are co-located with phosphatidylserine (PS) on the cell surface of tumor cells [14-16]. Moreover, an Hsp70 membrane-positive phenotype is associated with a higher resistance towards radiochemotherapy and membrane Hsp70 expression might therefore predict an unfavourable therapeutic outcome in lung and lower rectal tumors [17]. Taken together, these findings indicate the importance of determining the Hsp70 membrane status of tumors.

Within the last few years, non-invasive devices for the imaging of tumors in small animals have been developed [18]. Intraoperative and near-infrared fluorescence (NIRF) analyses are innovative approaches for tracking fluorophor-labelled probes, such as antibodies, in mice. The present invention provides for the first time a syngeneic tumor mouse model to study the distribution and binding characteristics of the cmHsp70.1 mAb in vivo. Screening of several mouse tumor cell lines revealed an Hsp70 membrane-positive phenotype on CT26 colon carcinoma, ADJ plasmocytoma, B16/F10 melanoma and MOS162 mouse osteosarcoma cells at 4° C. Following a temperature shift to 37° C., the cmHsp70.1 mAb was rapidly taken up into early endosomes and lysosomes of CT26 tumor cells in vitro. Following i.v. injection of fluorescence-conjugated cmHsp70.1 mAb into the tail vein of CT26 tumor-bearing mice, the cmHsp70.1 mAb selectively and rapidly accumulates in endo-lysosomal compartments in vivo. In addition to its tumor imaging capacity, the cmHsp70.1 mAb can mediate cellular cytotoxicity (ADCC).

In addition, The TKD sequence which is exposed to the extracellular milieu of tumors resides in the C-terminally localized oligomerization domain of the Hsp70 molecule (11). Furthermore, this TKD peptide in combination with low dose IL-2 has been found to stimulate the migratory and cytolytic capacity of NK cells against membrane Hsp70 positive tumor cells (12). The present invention herein demonstrates as mentioned above, consecutive injections of the cmHsp70.1 mAb into mice bearing CT26 tumors can significantly reduce the mass of membrane Hsp70 positive tumors and increase overall survival during therapy via the induction of antibody-dependent cellular cytotoxicity (ADCC). The in vitro ADCC activity could be further enhanced by using TKD/IL-2-activated NK cells as effector cells instead of unstimulated mouse spleen cells. The findings in accordance with the present invention therefore demonstrate that membrane Hsp70 serves as a novel therapeutic target for antibody mediated therapies for a broad spectrum of different tumor entities.

Particularly, the present invention concerns a monoclonal antibody cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, and cmHsp70.2 as well as the hybridoma producing it cmHsp70.2, deposited with the DSMZ—Deutsche Sammlung von Mikroorganismen und Zellkulturen GmbH on Nov. 14, 2003, and assigned Accession Number DSM ACC2630.

In a preferred embodiment, the antibody is a human, humanized, xenogeneic, or a chimeric human-murine antibody. Therapeutic compositions including the antibody or active fragments thereof, or agonists and cognate molecules, or alternately, antagonists of the same, and methods of use of such compositions in the prevention, diagnosis or treatment of tumorigenic or infections diseases using these compositions are also included, wherein an effective amount of the composition is administered to a patient in need of such treatment. However, for diagnostic uses and research in general murine antibodies are preferred as well.

The antigen-binding fragment of the monoclonal antibody can be a single chain Fv fragment, an F(ab') fragment, an F(ab) fragment, and an F(ab')$_2$ fragment, or any other antigen-binding fragment. In a specific embodiment, infra, the monoclonal antibody or fragment thereof is a murine IgG or IgM isotype antibody.

Naturally, the invention extends to the hybridoma that produces monoclonal antibody cmHsp70.1 or cmHsp70.2, which hybridoma is deposited with the DSMZ as indicated hereinbefore.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region of the antibody cmHsp70.1 or cmHsp70.2.

Accordingly, the present invention also encompasses vectors comprising said polynucleotides and host cells transformed therewith as well as their use for the production of an antibody capable of binding specifically extracellular localized epitopes of Hsp70 on intact cells, in particular tumor cells, or a functional fragment or immunoglobulin chain(s) thereof.

It is also an object of the invention to provide bi- or multifunctional molecules that comprise a binding domain of an antibody, an immunoglobulin chain or a binding fragment of the present invention, which binds cell surface membrane-bound heat shock protein (HSP), and at least one further functional domain.

The antibody, immunoglobulin chain(s), binding fragments thereof and ligands other than Hsp70 binding to said antibody can be used in pharmaceutical and diagnostic compositions for modulating and detecting an immune response or for the detection and/or treatment of a tumor.

Additionally, methods are provided for determining a tumor comprising assaying cells in a sample from a patient with the antibody or the bi- or multifunctional molecule according to the invention, wherein the presence or increased amount of extracellular localized Hsp70 is indicative for the tumor, and for treating a tumor or modulating the immune response in a subject in need thereof, comprising administering to the subject a therapeutically effective amount of said antibody or bi- or multifunctional molecule.

The use of the foregoing compositions in the preparation of medicament is preferred. In preferred embodiments, the medicament is useful in the treatment of conditions related to a tumor or an infections disease.

BRIEF DESCRIPTION OF THE DRAWINGS

FIG. 1 shows the result of a representative experiment with monoclonal antibody cmHsp70.1. Either unstimulated (NKd0) or stimulated (NKd3) NK cells were used as effector cells at E:T ratios ranging from 20:1 to 2:1. Unstimulated NK cells (NKd3) showed only weak lysis of CX+ and CX− tumor cells, in contrast Hsp70 activated NK cells (NKd3) showed significant lysis of CX+ tumor cells but only weak lysis of CX− tumor target cells. After pre-incubation of CX+ and CX− tumor target cells with Hsp70 specific antibody (5 µg/ml) for 1 h and then used as target cells in a 4 h Cr-51 release assay, lysis of CX+ tumor cells (left graph) could be completely blocked by Hsp70 Ab whereas lysis of CX− target cells (right graph) remained unaffected. The data represent the mean values of three independent experiments+/−SE.

Figure 1:
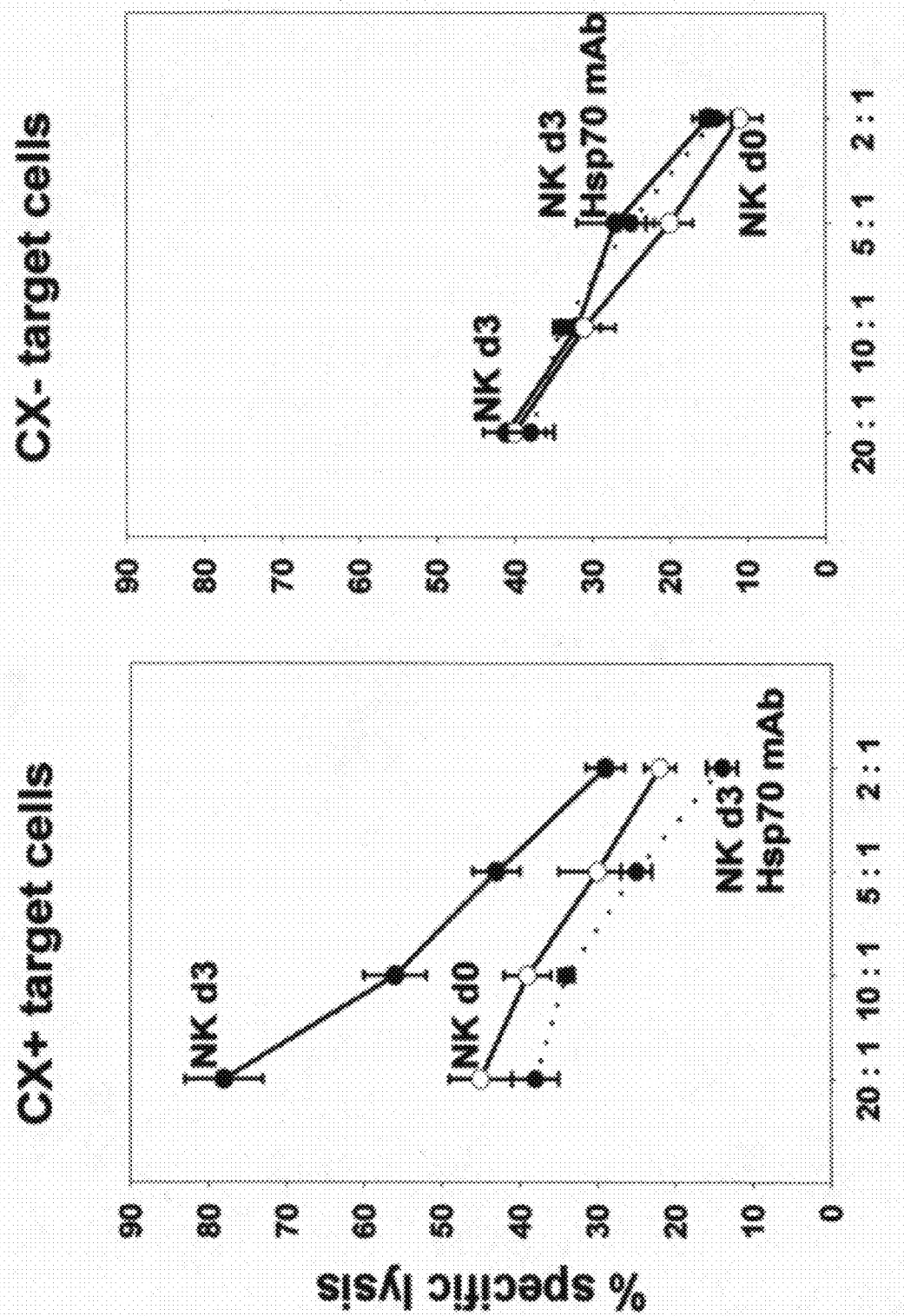
FIG. 1: Hsp70 antibody of the invention block cytolytic activity of activated NK cells (NKd3).

Two and three consecutive injections of cmHsp70.1 mAb (intravenously) result in a significant reduction in tumor weight (*P<0.05). The cmHsp70.1 mAb (20 μg per injection) is injected intravenously on days 3, 5 and 7 following intraperitoneal injection of $2.5\times10^4$ CT26 tumor cells. Mice are killed on day 14 and tumor weights are determined Data are means of six to nine animals (*P<0.05). (C) Three (filled square) but not one (filled triangle) injections of cmHsp70.1 mAb (i.v.) result in a significant growth delay of subcutaneously injected CT26 tumors (*P<0.05). The cmHsp70.1 mAb (20 μg per injection) is injected intravenously on days 4, 7, and 10 following subcutaneous injection of $1\times10^6$ CT26 tumor cells. Tumor weight is measured in each mouse every second day after the last antibody injection (*P<0.05 for all time points from day 10 onwards). (D) Control mice (open circles) and mice that have been injected only once with mAb cmHsp70.1 (filled circles, day 5) become moribund from day 18 onwards, whereas mice that have been injected three times (filled squares, day 4, 7, 10) with cmHsp70.1 mAb shows a significant increase in overall survival (*P<0.05). Each data point represents measurements of six to nine mice.

Figure 5:
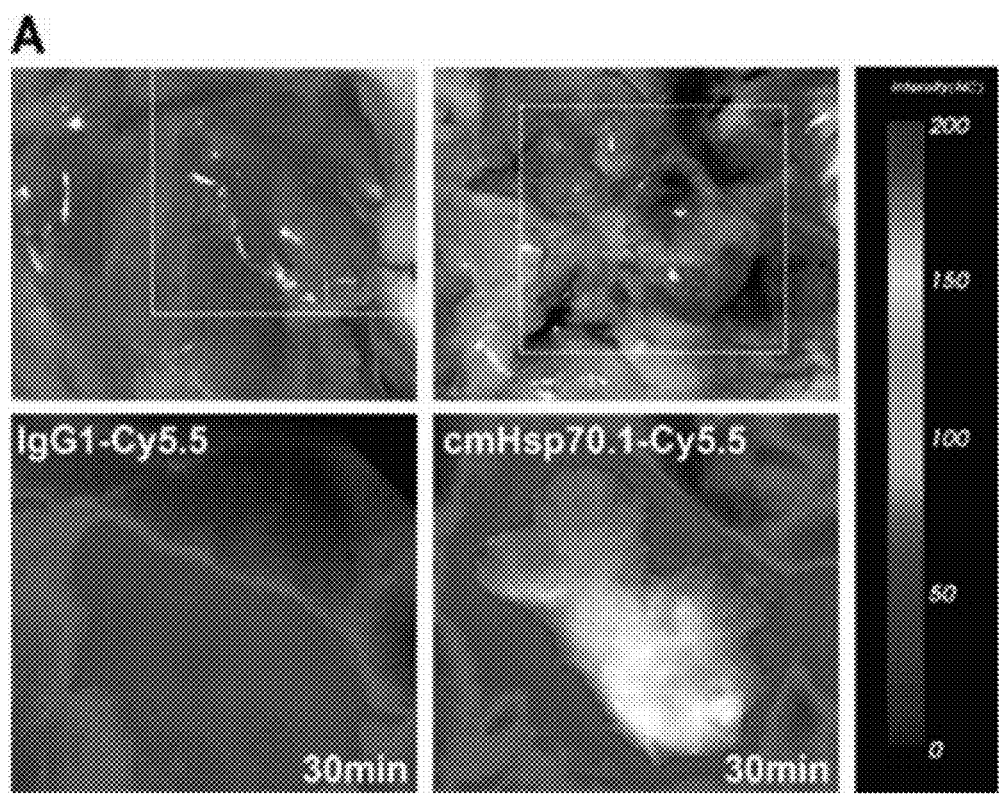
Figure 5:
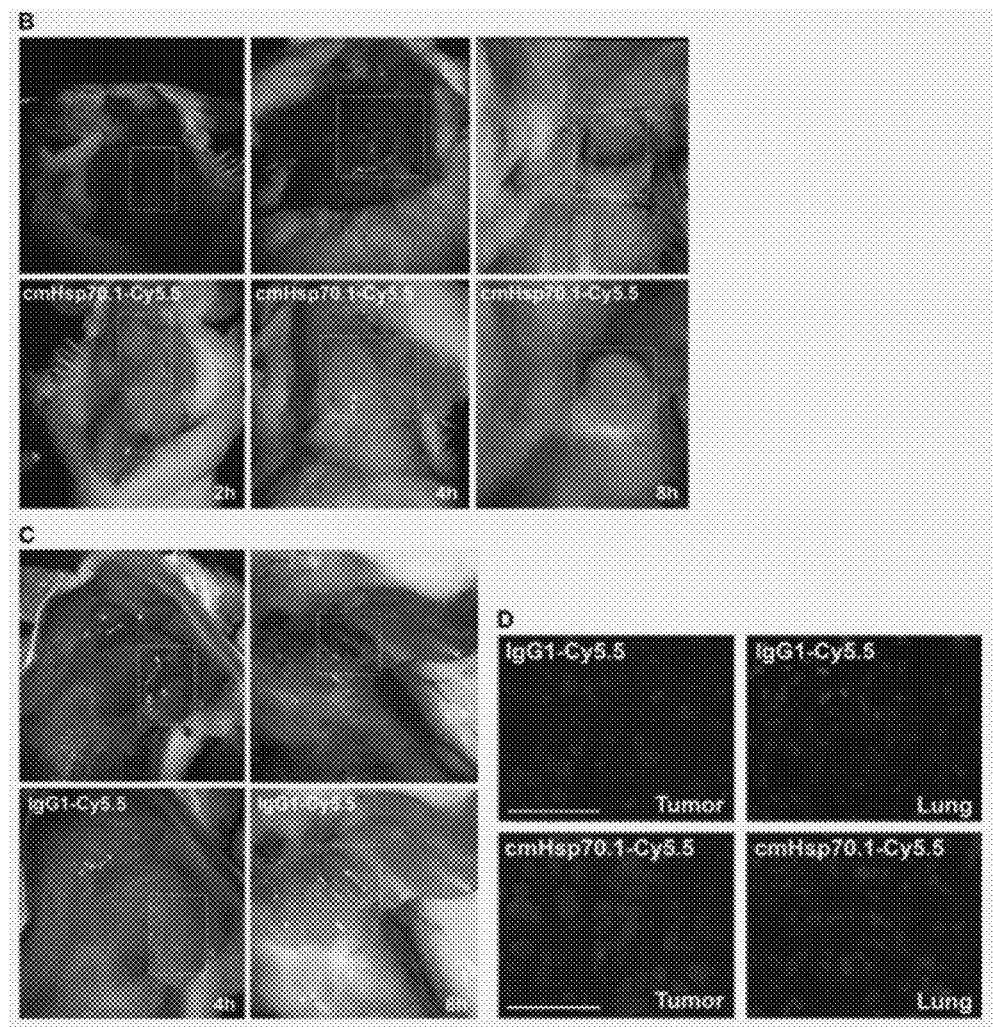

FIG. 5: (A) Optical imaging. Intraoperative detection of cmHsp70.1-Cy5.5 mAb in tumor-bearing BALB/c mice. 100 μg of cmHsp70.1-Cy5.5 mAb as well as the IgG1-Cy5.5 control were injected i.v. into the tail vein of CT26 tumor-bearing mice on day 14. Representative views of the Cy5.5 fluorescence and autopsy images of the dorsal part of the mice were taken 30 min after i.v. injection of the antibodies. Upper panel, autopsy image of the dorsal located mouse tumor in true colors. Lower panel, false color images of the Cy5.5 staining within the tumor. The massive fluorescence signal corresponds to the anatomic position of the CT26 tumor which is stained with cmHsp70.1-Cy5.5 mAb. Almost no staining with an equivalently labelled IgG1 isotype-matched control is detectable. (B) Kinetics of the intraoperative detection of cmHsp70.1-Cy5.5 mAb in CT26 tumor-bearing mice on day 14. Representative views of the Cy5.5 fluorescence images of the dorsal part of the mice were taken 2, 4 and 8 h after i.v. injection of the antibody. Upper panel, autopsy images of the dorsal located mouse tumor in true colors. Lower panel, false color images of the Cy5.5 staining within the tumor indicated in red. (C) Kinetics of the intraoperative detection of IgG1-Cy5.5 control immunoglobulin in CT26 tumor-bearing mice on day 14. Representative views of the Cy5.5 fluorescence images of the ventral part of the mice were taken 4 and 8 h after i.v. injection of the antibody. Upper panel, autopsy images of the ventral located mouse tumor in true colors. Lower panel, false color images of the Cy5.5 staining indicated in red. No staining was detectable within the tumor following the administration of the IgG1-Cy5.5 isotype-matched control. (D) Immunofluorescence views of tumor and normal tissue (lung) sections (10 μm) derived from the same animals, 8 h after i.v. injection of IgG1-Cy5.5 (upper panel) or cmHsp70.1-Cy5.5 mAb (lower panel). The nuclei are visualized in blue (DAPI) and the localization of Hsp70 is visualized in red (Cy5.5). The scale bar represents 50 μm.

Figure 6:
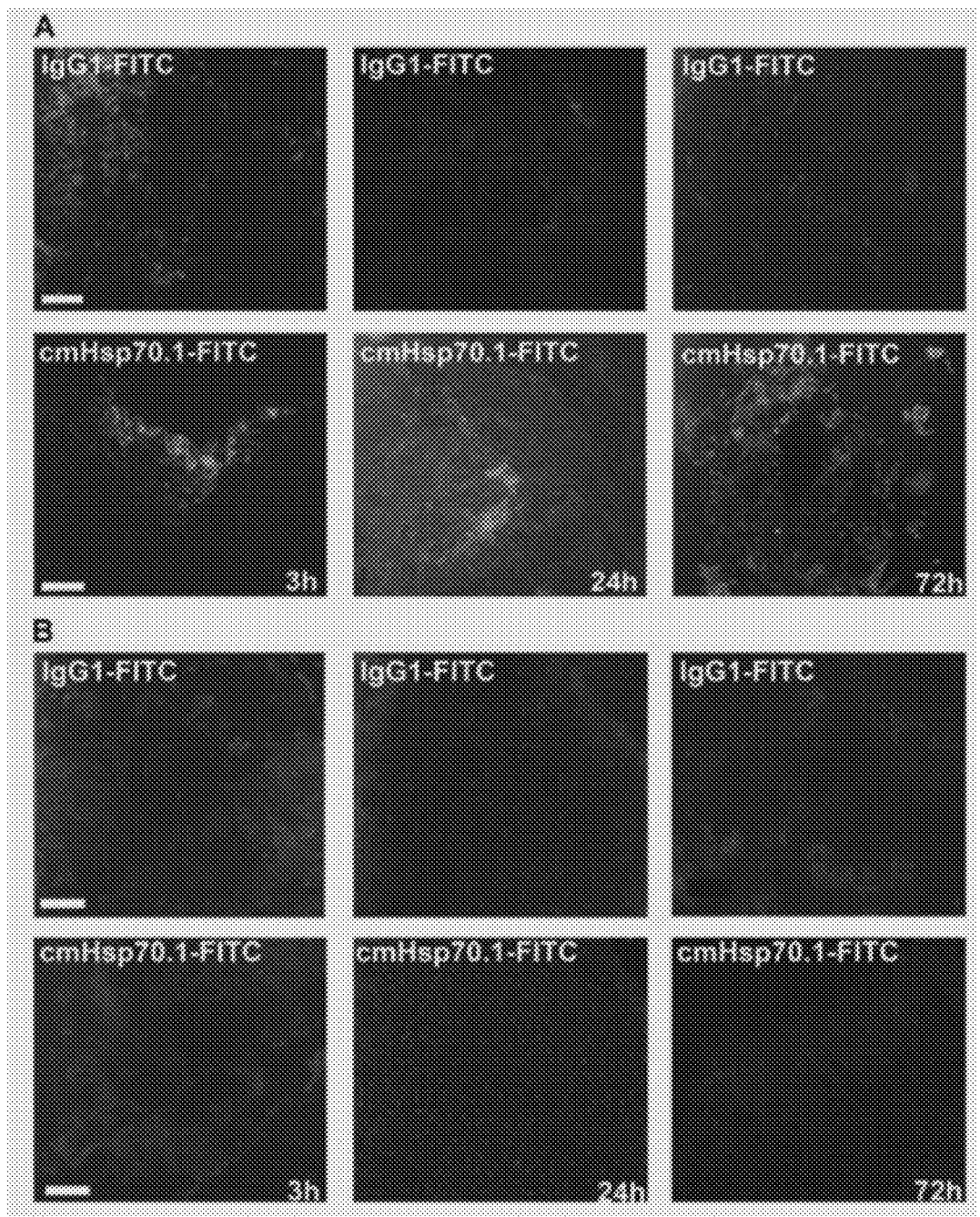
Figure 6:
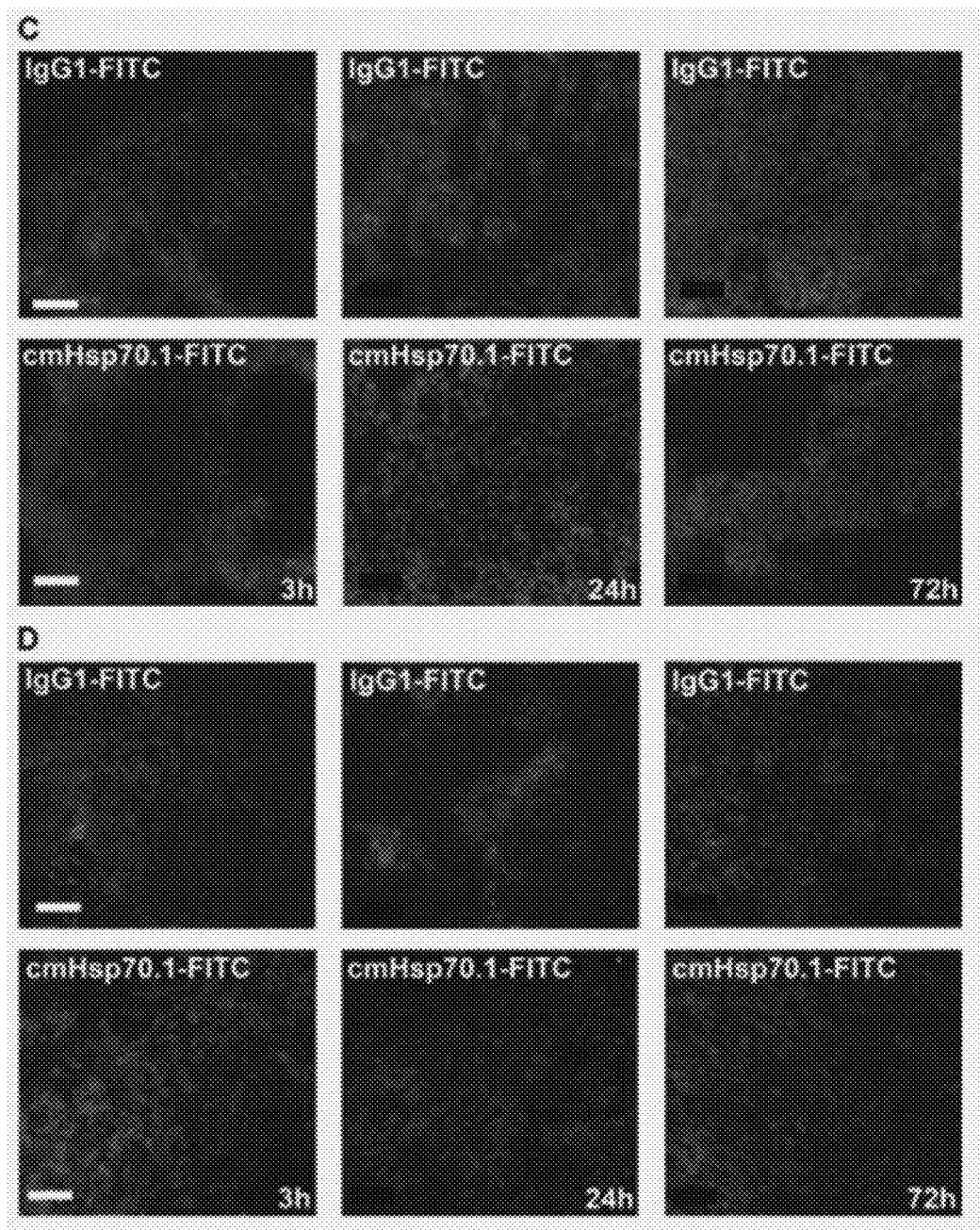

FIG. 6: Immunofluorescence analysis of tumor and normal tissue sections. cmHsp70.1-FITC mAb (lower panel) or the identically labelled IgG1 control (upper panel, 100 μg each) was injected into the tail veins of tumor-bearing mice on day 14 after i.p. tumor cell (CT26) injection. Animals were sacrificed 3, 24 and 72 h thereafter and the tumor (A), liver (B), lung (C) and kidney (D) were cryo-conserved. Representative views of sections (5 μm) of the tumors and organs were taken at the indicated time points after the injection of the IgG1-FITC (upper panel) and cmHsp70.1-FITC mAb (lower panel). The nuclei are stained in blue (DAPI) and the localization of Hsp70 is visualized in green (FITC). The scale bar represents 100 p.m.

Figure 7:
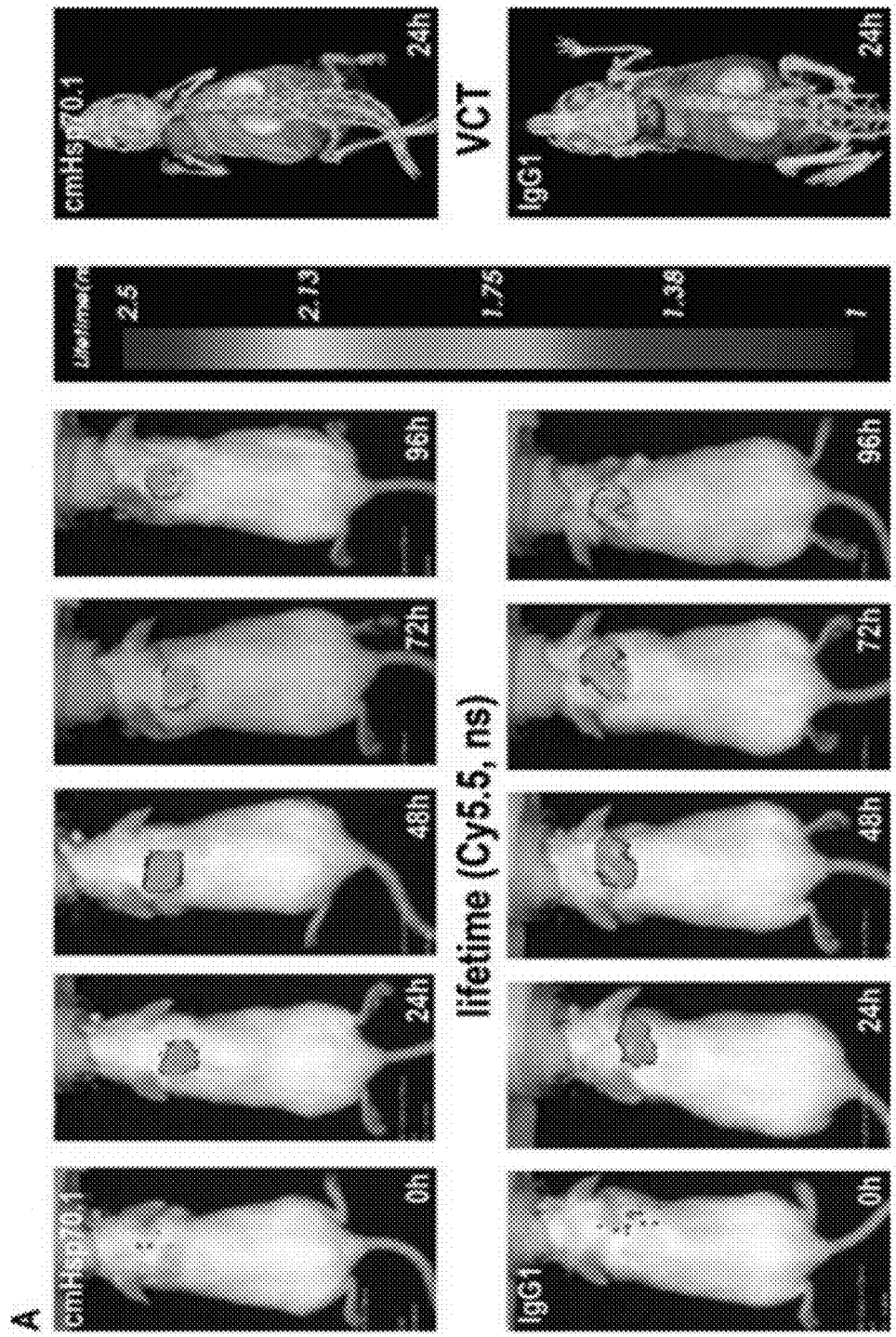
Figure 7:
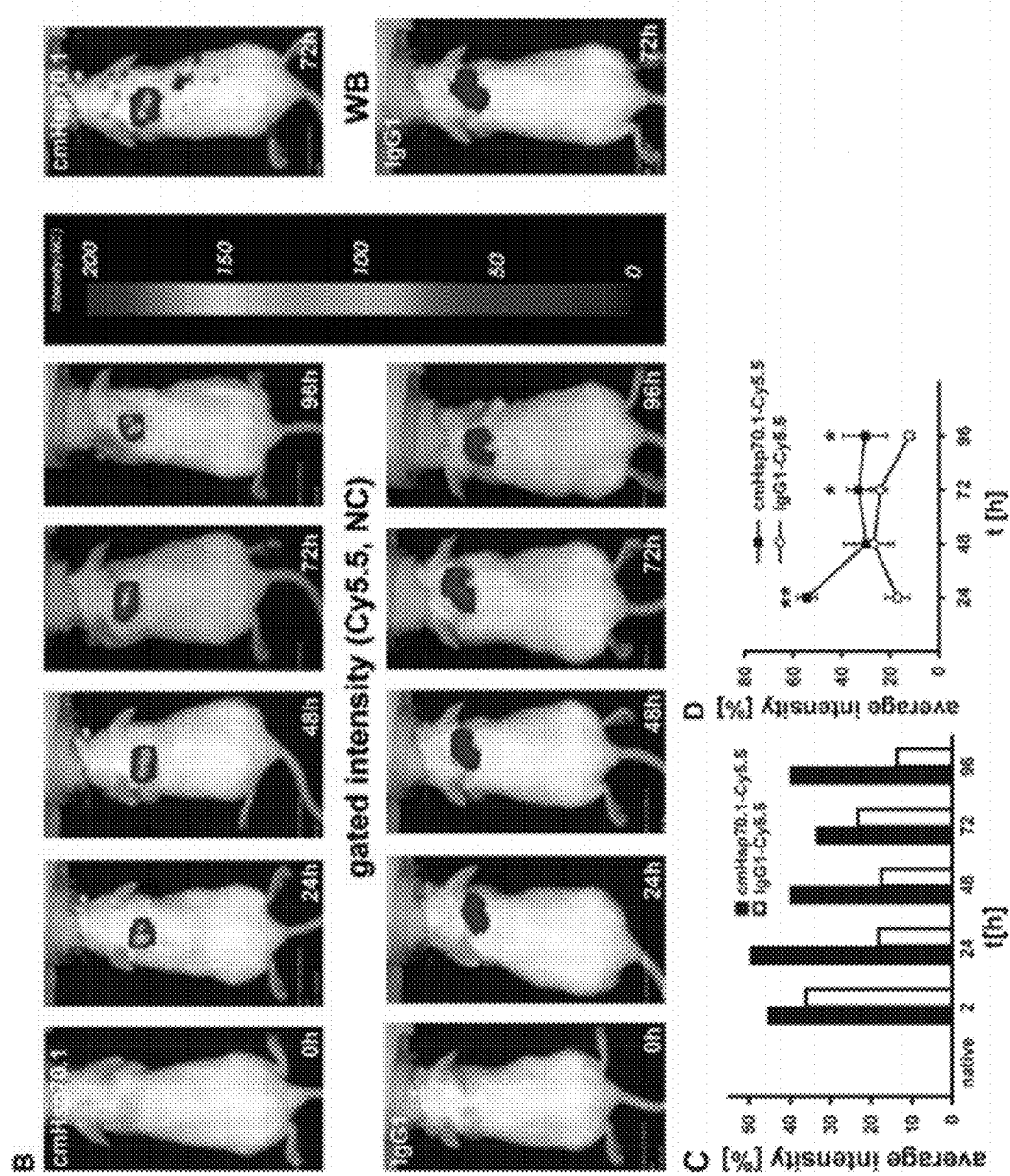

FIG. 7: (A) Lifetime images and flat-panel VCT scans. Representative lifetime images were obtained using the Optix system. Representative fluorescence signals over the s.c. located CT26 tumor regions show lifetimes of 1.7 ns which are characteristic for Cy5.5-conjugated cmHsp70.1 mAb (upper panel) and the IgG1 (lower panel) isotype-matched control. Images were taken 0, 24, 48, 72 and 96 h after i.v. injection into the tail vein. The peak emission of Cy5.5 is at 694 nm in the bright green area. Localization of the CT26 colon adenocarcinoma in the dorsal neck region of the mice is depicted in the volume rendered flat-panel VCT scans which were taken 24 h after the injection of the cmHsp70.1 mAb and isotype-matched control on days 14, 15, 16 and 17 after the tumor cell injection. On day 14, the tumor size which was determined by flat-panel VCT, was 0.227 $cm^3$ in mice injected with cmHsp70.1 mAb, and 0.211 $cm^3$, in mice injected with the IgG1 control antibody. (B) Representative fluorescence intensity images obtained by the Optix system. Fluorescence intensity is displayed in normalized counts (NC) and is presented from two CT26 tumor-bearing mice 0, 24, 48, 72 and 96 h after i.v. injection of the cmHsp70.1-Cy5.5 mAb (upper panel) and an identically labelled IgG1 isotype-matched control (lower panel). Strong fluorescence signals (red outline) over the tumor of the mouse that had received the cmHsp70.1-Cy5.5 mAb, but not over the tumor in the animal that had been injected with the IgG1-Cy5.5 control were visible between 24 and 96 h. Whole body scans (WB) of the identical mice 72 h after injection of the mAb and isotype control are shown on the outer right part of the graph. Fluorescence signals were only apparent over the tumor region. (C) Quantitative analysis of the fluorescence intensity images of the tumors of mice that received either cmHsp70.1-Cy5.5 mAb (black bars) or IgG1-Cy5.5 (white bars). Average intensities of fluorescence signals in the s.c. tumor regions of the two mice shown in B at the indicated time-points 0, 24, 48, 72 and 96 h after i.v. injection of the antibodies are displayed. The data were corrected for their labelling intensities. (D) Kinetics of average fluorescence intensity of cmHsp70.1-Cy5.5 mAb (black dots) and IgG1-Cy5.5 control (white dots) in tumor-bearing mice. The data represent a summary of the average fluorescence intensity over tumor regions in mice at 24, 48, 72 and 96 h after i.v. injection of the antibodies. Data represent mean values of 5 animals; * marks values p<0.05; ** marks values p<0.001.

Figure 8:
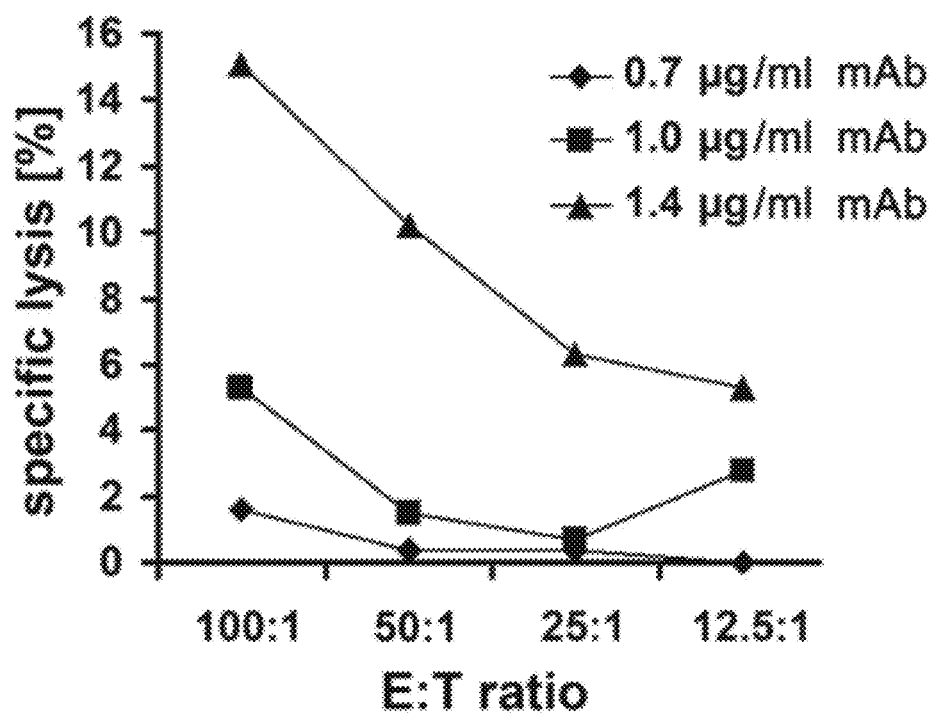

FIG. 8: Capacity of cmHsp70.1 mAb to induce ADCC against CT26 tumor cells in vitro. In vitro ADCC of CT26 colon (containing 55% Hsp70 membrane-positive cells) carcinoma cells, using 0.7, 1 and 1.4 μg/ml cmHsp70.1 mAb and unstimulated mouse spleen cells at E:T ratios ranging from 100:1 to 12.5:1. The data show one representative experiment out of 3 independent experiments showing similar results.

Figure 9:
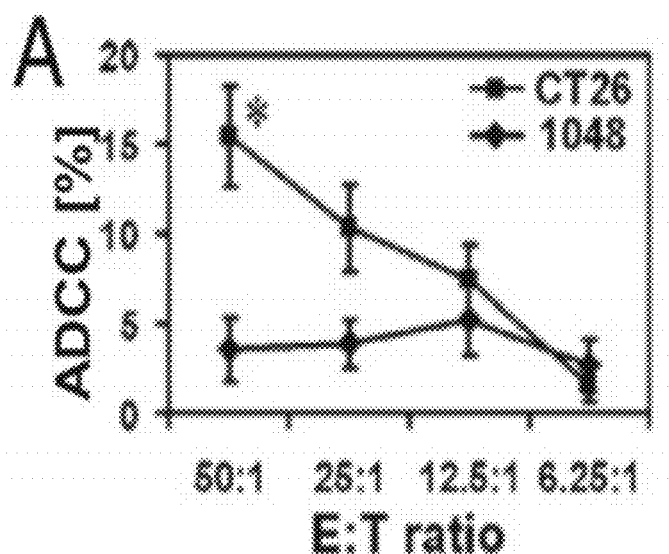
Figure 9:
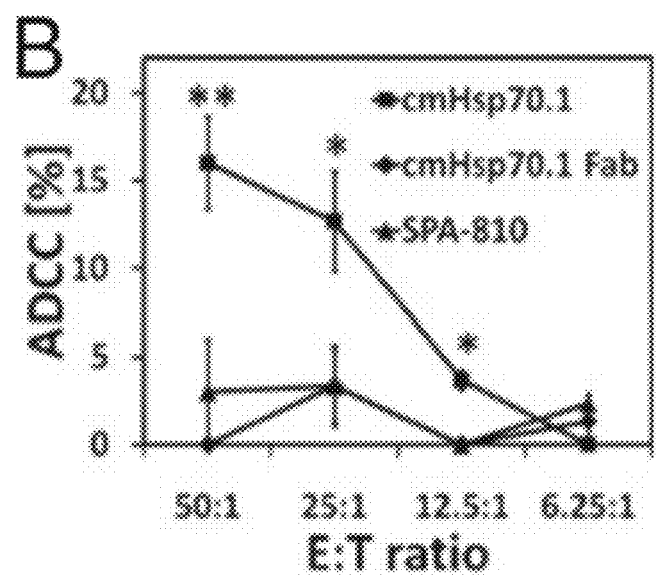
Figure 9:
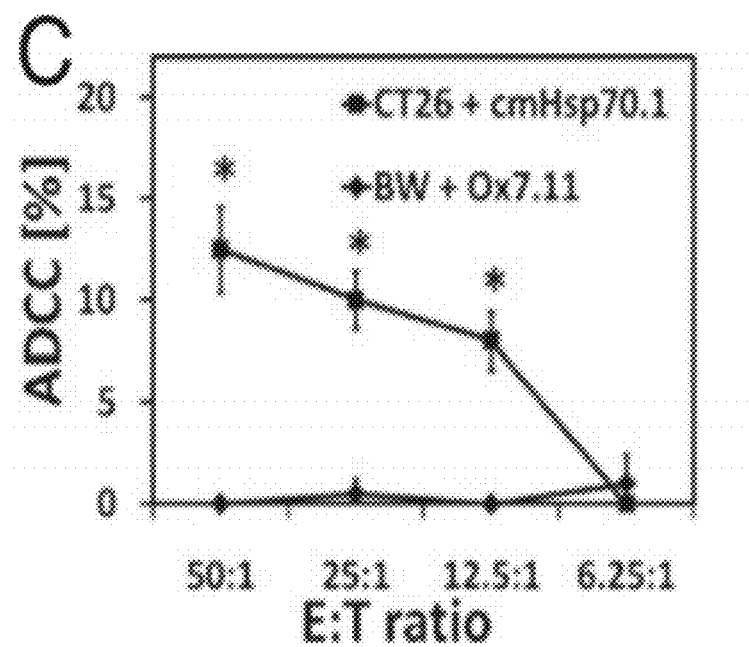
Figure 9:
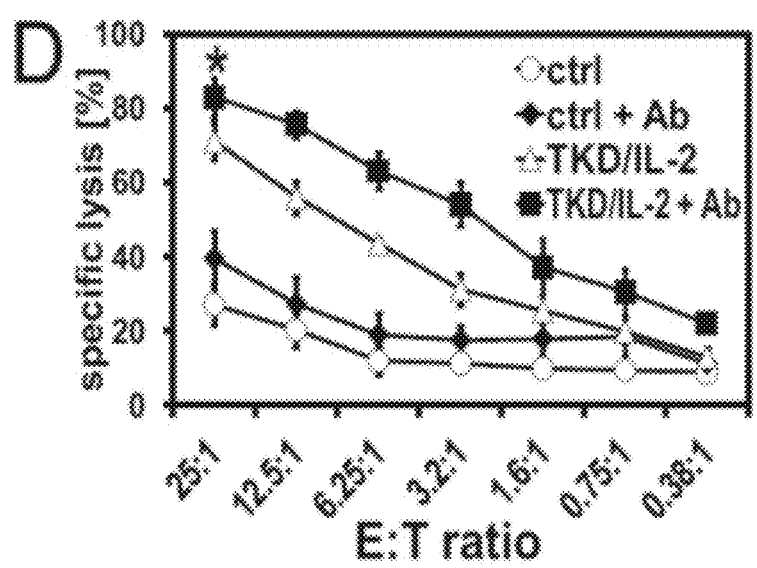

FIG. 9: Comparative analysis of ADCC using different IgG1 mAbs and cmHsp70.1 Fab fragment. (A) In vitro ADCC of membrane $Hsp70^+$ mouse CT26 colon (60%, filled squares) and membrane $Hsp70^-$ 1048 pancreatic carcinoma cells (filled diamonds), using 50 μg/mL Hsp70.1 mAb and unstimulated mouse spleen cells at E:T ratios ranging from 50:1 to 6.25:1. (B) In comparison with cmHsp70.1 mAb (filled squares), no significant ADCC is induced in mouse CT26 colon carcinoma cells (61% cmHsp70.1$^+$) using the nonbinding IgG1 mAb SPA810 (filled circles) or cmHsp70.1 Fab fragment (filled triangles). (C) The IgG1 O×7.11 mAb, which detects the theta antigen on 56% of the BW mouse tumor cells, does not induce ADCC in BW mouse tumor cells (filled triangles). Specific ADCC is measured using 50 μg/mL antibody or Fab fragment, respectively; unstimulated mouse spleen cells at E:T ratios ranging from 50:1 to 6.25:1 are used as effector cells. Specific lysis mediated by the direct cytotoxic effect of NK cells in the absence of cmHsp70.1 mAb are subtracted. The phenotypes of the effector cells are summarized in Table 4. Data are means±SE of at least three independent experiments (**P<0.01; * P<0.05). (D) Comparative analysis of the capacity of unstimulated (ctrl, open circles; ctrl+Ab, filled diamonds) and TKD (2 μng/mL) plus IL-2 (100 IU/mL) preactivate (TKD/IL-2, open triangles; TKD/IL-2+Ab, closed squares) mouse spleen cells to kill CT26 carcinoma cells. The ADCC experiment are performed either in the absence (open symbols) and presence (+Ab; closed symbols) of 50 μg/mL cmHsp70.1 mAb. Lysis is mediated by ADCC in the presence of cmHsp70.1 mAb and by a direct cytotoxic effect of mouse NK cells in the absence of mAb, at E:T ratios ranging from 25:1 to 0.38:1. Data are means±SE of at least three independent experiments. Lysis of activated effector cells in the absence and presence of cmHsp70.1 mAb are significantly different (*P<0.05, all E:T ratios). ADCC are calculated using the formula: percent of specific lysis=(experimental release−spontaneous release)/(maximum release−spontaneous release)×100.

Figure 10:
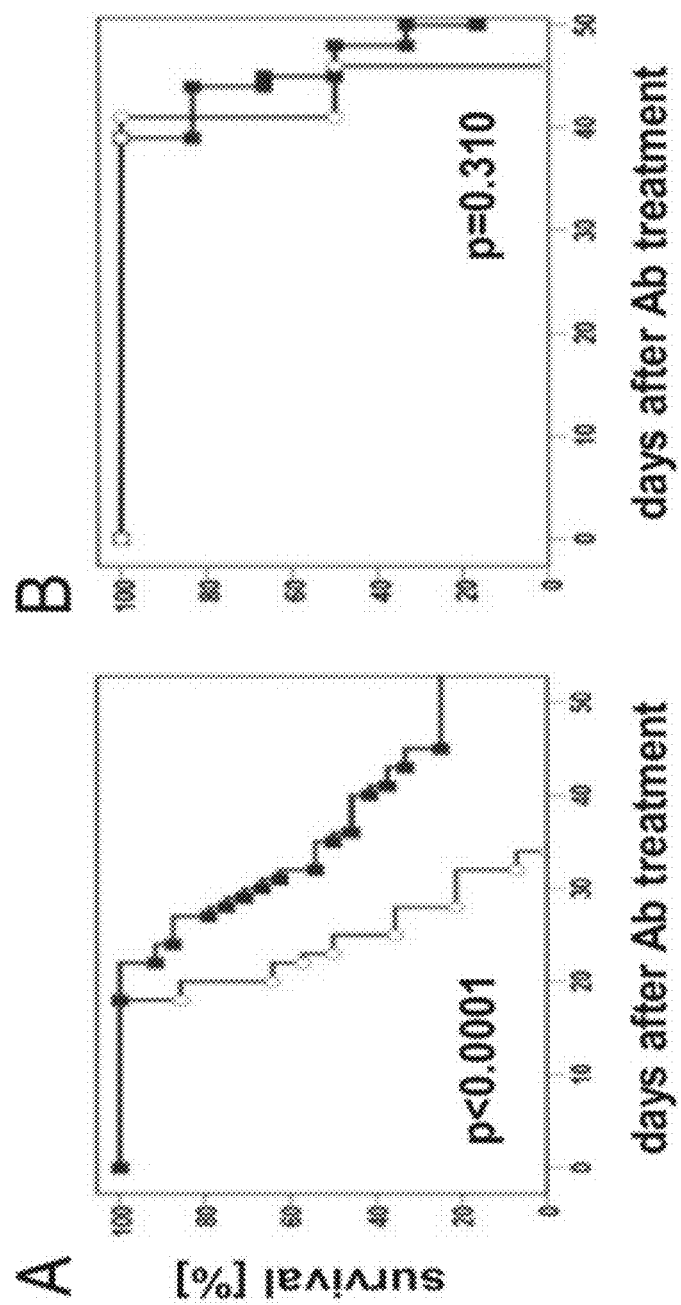

FIG. 10: (A) Kaplan-Meyer curves of overall survival of mice treated with an isotype-matched control antibody or cmHsp70.1 mAb on days 3, 5 and 7 after tumor injection of CT26 tumor cells (20 μg per injection). The overall survival of mice (3×Ab cmHsp70.1; filled squares; n=24) treated with cmHsp70.1 mAb is significantly higher than that of animals (ctrl; open circles; n=14) that receive the IgG1 isotype-matched control antibody (p<0.0001). (B) In contrast, the cmHsp70.1 mAb treatment (3×Ab cmHsp70.1; filled squares) has no significant effect on the survival of mice bearing membrane Hsp70 negative A20 lymphomas (n=12) compared to mice receiving the IgG1 isotype-matched control antibody (ctrl; open circles; n=4) (p=0.310).

Figure 11:
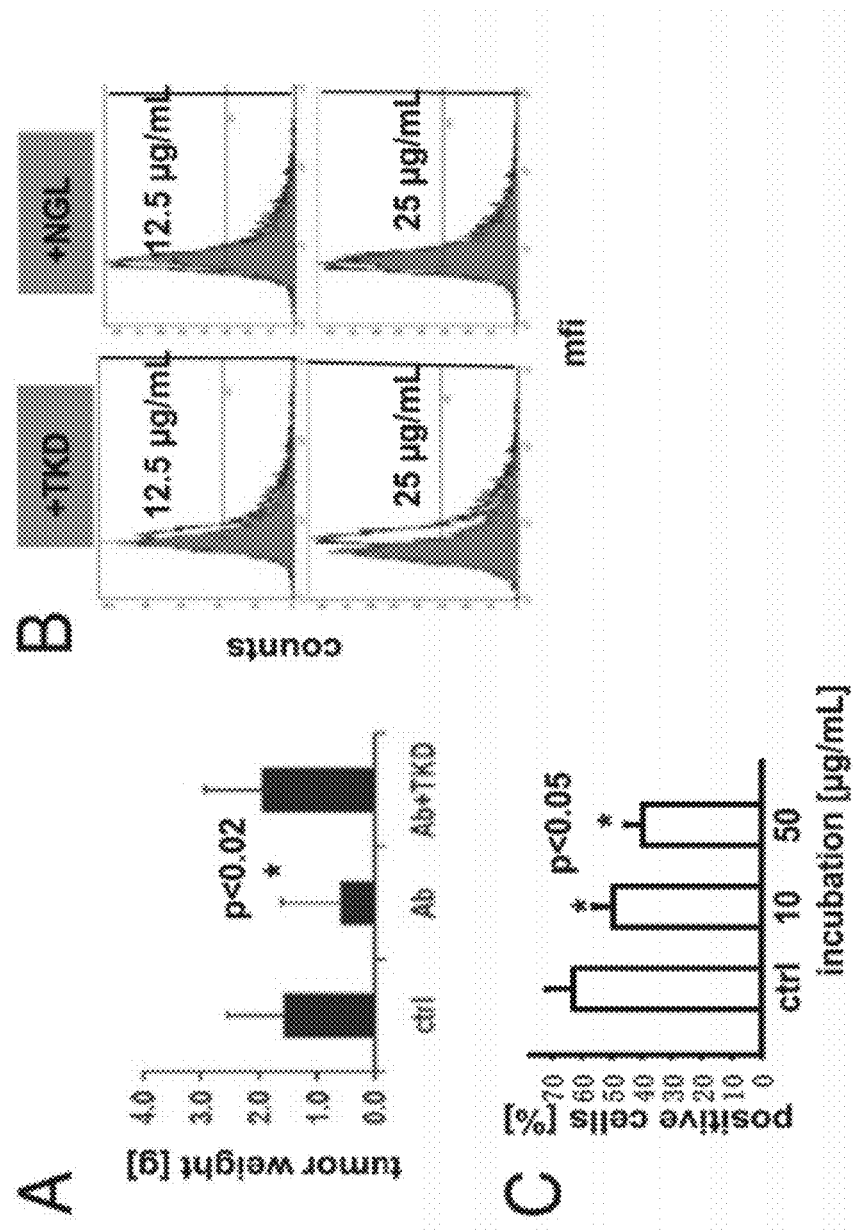

FIG. 11: (A) Coinjection of an excess of the Hsp70 peptide TKD with the cmHsp70.1 mAb completely inhibits the significant antitumoral effect of the latter (*P<0.02). The cmHsp70.1 mAb (20 μg per injection) is coinjected intravenously on days 3, 5 and 7 together with 50 μg TKD following intraperitoneal injection of $2.5 \times 10^4$ CT26 tumor cells; media, n=21; Ab, n=22; Ab+TKD, n=21. Mice are killed on day 14 and tumor weights are determined (B) Binding of cmHsp70.1-FITC mAb to CT26 tumor cells was inhibited by the coincubation with an excess of TKD peptide. As a control, the scrambled NGL peptide is used. Tumor cells are coincubated either with cmHsp70.1-FITC mAb (5 μg/mL; white histogram) or with cmHsp70.1-FITC mAb (5 μg/mL) plus TKD (gray histogram; Left) or NGL peptide (gray histogram; Right) at concentrations of 12.5 and 25 μg/mL, respectively. The data illustrate one representative experiment out of three independent experiments, all of which show similar results. (C) Binding of cmHsp70.1-FITC to CT26 tumor cells is inhibited significantly (*P<0.05) by the coincubation with the C-terminal substrate-binding domain of Hsp70 in a concentration dependent manner (10 and 50 μg/mL).

DETAILED DESCRIPTION OF THE INVENTION

The present invention concerns methods and compositions for the diagnosis, prevention and treatment of primary and metastatic neoplastic diseases and infectious diseases and for eliciting an immune response in a human individual. In particular, the present invention relates to molecules that bind to an extracellular localized epitope of Hsp70 on tumor cells, especially intact tumor cells. More specifically, the present invention relates to antibodies and antigen-binding fragments thereof, which demonstrate the immunological binding characteristics of monoclonal antibody cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or of cmHsp70.2 produced by the hybridoma cmHsp70.2, deposited with the DSMZ—Deutsche Sammlung von Mikroorganismen und Zellkulturen GmbH on Nov. 14, 2003, and assigned Accession Number DSM ACC2630. Where present, the term "immunological binding characteristics," or other binding characteristics of an antibody with an antigen, in all of its grammatical forms, refers to the specificity, affinity, cross-reactivity, and other binding characteristics of an antibody.

As mentioned before, while several antibodies specific for Hsp70 exist, only two of them have been reported to recognize occasionally an epitope that is localized extracellularly. The failure to bind to plasma membrane bound Hsp70 by its extracellular epitope might be due to either instability or varying quality of the antibody or to its requirement for very specific binding conditions that are not always given.

Antibodies for diagnostic and/or therapeutic purposes however need to work reliably under various conditions encountered in routine laboratories and should be produced by a stable source, i.e. hybridoma cell line.

The present invention provides two hybridoma lines and the antibodies produced by them. It was surprisingly found that both purified antibodies are capable of binding to Hsp70 localized on the plasma membrane via an extracellular epitope. Since only transformed and infected human cells, respectively, appear to express Hsp70 on their cell surface the antibodies according to the invention are able to distinguish between normal and tumor cells. Thus, the invention provides an antibody or antigen-binding fragment thereof that binds to an extracellularly localized epitope of Hsp70 on tumor cells, which gives rise to several embodiments described herein.

The experiments performed within the scope of the present invention reveal that similar to the tumor cell lines, single cell suspensions of primary human gastrointestinal and pancreatic tumor samples (n=229) can also be stained with the antibody of the present invention exemplified by cmHsp70.1 mAb. A membrane Hsp70 positive phenotype with the cmHsp70.1 mAb can be determined in more than 40% of the cases. In contrast, the corresponding reference tissues derived from the same patients are always membrane Hsp70 negative as indicated in Table 2 of Example 4.

Since the expression of Hsp70 on the cell surface is a hallmark of several different types of cancer, see supra while being absent from the plasma membrane of normal cells (Multhoff et al., Int. J. Cancer 61 (1995b), 272) a preferred embodiment of the antibody of the present invention binds to tumor cell, wherein said tumor is a human tumor selected from the group consisting of colon, lung, stomach, pancreas, head and neck, ovary, and/or breast cancer, melanoma, glioblastoma, sarcoma blastocytoma and/or hematological malignancies which are usually strongly correlated with tumor type and may play a role in earliest stages of tumor initiation, those hematological malignancies comprise Acute Myeloid Leukemia (AML), Myelodysplastic Syndromes (MDS), Myeloproliferative Disorders (MPD), Acute Lymphoblastic Leukemia (ALL), lymphomas such as Burkitt's lymphoma, Hodgkin's disease, non-Hodgkin's and non-Burkitt's lymphomas, and Lymphoproliferative Disorders (LPD), i.e. B- and T-lineage disorders.

In a preferred embodiment of the present invention, the antibodies recognize an epitope that comprises or consists of the amino acid sequence NLLGRFEL (SEQ ID NO: 1) or TKDNNLLGREFLSG (SEQ ID NO: 2). The peptides of SEQ ID NO: 1 and 2 were shown to be presented on the extracellular side of the plasma membrane when Hsp70 is localized on the cell surface and inhibit the binding of antibodies according to the invention in a dose dependent manner. Most preferably, said antibodies are monoclonal antibodies. In particular, the antibody or the antigen-binding fragment thereof of the present invention preferably exhibit the immunological binding characteristics of monoclonal antibody cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or of cmHsp70.2 as produced by the hybridoma cmHsp70.2, deposited with the DSMZ—Deutsche Sammlung von Mikroorganismen und Zellkulturen GmbH on Nov. 14, 2003, and assigned Accession Number DSM ACC2630. The immunological binding characteristics of monoclonal antibody cmHsp70.1 are substantially the same as those of antibody RPN1197 described inter alia in international patent application WO02/22656; see particularly the examples, the disclosure of which is incorporated herein by reference. However, while international application WO02/22656 as well as other publications by the inventors, e.g., Botzler et al., Cell Stress & Chaperones 3 (1998), 6-11, describe the desired immunological characteristics of an antibody of the present invention, especially that the antibodies are capable of binding to viable Hsp70-expressing (CX+) tumor cells and preferably also substantially inhibit the lysis of CX+ cells, the present invention for the first time enables the unlimited provision of such antibodies and reliable sources, in particular corresponding hyprodoma cell lines. Hence, the provision of the hybridomas producing monoclonal antibodies cmHsp70.1 and cmHsp70.2, respectively, enables the person skilled in the art to design and produce functionally equivalent antibodies, for example by adapting the antigen-binding site of either of the mentioned antibodies.

Each of the two antibodies specifically provided is unique with respect to its respective immunological and biological activities. Both may be distinguished from other anti-Hsp70 antibodies by their ability to bind to extracellular epitopes of Hsp70, in particular on intact and viable tumor cells. They are also capable of exhibiting an inhibitory effect on the cytolytic activity of NK cells against Hsp70 expressing tumor cells; see FIG. 1. Hence, Hsp70 binding molecules derived from cmHsp70.1 or from cmHsp70.2 are preferably used in but not limited to therapeutic and diagnostic applications.

In this context, it should be noted that the epitope that is recognized by the antibodies of the present invention can also be directly recognized by transiently plastic adherent NK cells via their CD94 receptor (C-type lectin like kill receptor). This NK sub-cell population express high amounts of CD94 upon incubation with the TKD peptide and low dose of IL-2; see WO 02/022656 at page 20, second and third paragraph as well as in Table 3 and the following conclusions. Therefore, when the cmHsp70.1 and cmHsp70.2 antibodies of the present invention bind to Hsp70 on the cell surface of tumor cells the epitope cannot be recognized by this CD94+ NK cell sub-cell population and the cytolytic activity of NK cells against Hsp70 expressing tumor cells is blocked.

In addition, the antibody-dependent cellular cytotoxicity (ADCC) as shown in the Examples 10 to 11 and in FIGS. 8 and 9 is mediated inter alia by another subtype of unstimulated NK cells, which express high amounts of the cell surface receptor CD16. This receptor has been described to be expressed on both murine and human NK cells and facilitates ADCC by binding to the Fc portion of various antibodies, thereby triggering the lyses of the target cells which is of common general knowledge of a person skilled in the art. While NK cells stimulated with a combination of the TKD peptide and IL-2 down regulate the CD16 receptor and up regulate the CD94 receptor those cells are not able to induce ADCC. However, NK cells which express high amounts of CD16 receptor on their cells surface, i.e. not stimulated, mediate the observed ADCC effect.

The ADCC is also mediated by neutrophils and monocytes and therefore is increased in vivo. As evident from Table 3 of Example 6 lymphocytic and granulocytic infiltration of CT26 tumors after injection of the cmHsp70.1 antibody results that the ADCC effect is also mediated by the different lymphocytic cells in vivo.

H As evident from the Examples of the present invention and in particular as shown in FIGS. 8, 9 and 11 and the Examples 10 to 13, a significant cmHsp70.1-antibody dependent cellular cytotoxicity (ADCC) response can be induced selectively in membrane Hsp70 positive tumor cells by unstimulated mouse spleen cells. The tumor killing is further enhanced by using TKD/IL-2 pre-stimulated effector cells in the ADCC-assay. Three consecutive injections of the cmHsp70.1 mAb into CT26 tumor-bearing mice (i.p.) resulted in a significant inhibition of tumor growth and an enhanced overall survival which is associated with an infiltration of NK cells, macrophages and granulocytes. The ADCC response is completely reversed when cmHsp70.1 mAb are co-injected with the cognate TKD peptide; see Example 13 and FIG. 11. In line with these results, co-incubation of CT26 tumor cells with cmHsp70.1 mAb and the TKD peptide inhibited the antibody-binding in vitro, hence confirming the Hsp70-specificity of the anti-tumor response; see also the Examples.

Furthermore, in one embodiment the antibodies of the present invention are preferably characterized in that 0.1 to 10 µg/ml, preferably less than 5 µg/ml and most preferably about 0.1 to 1 µg/ml of the antibody of the invention is sufficient for the detection of CX tumor cells followed by protein A-bold labelling (10 µm Aurion) and viewed in a Zeiss EM 10CR electron microscope; see for experimental details, e.g., Botzler et al., Cell Stress & Chaperons 3 (1998), 6-11. Furthermore, the antibodies of the present invention are preferably characterized in that they are able to block the cytolytic activity of activated NK cells; see FIG. 1. In such experiments usually 1 to 20 µg/ml, preferably 5 to 10 µg/ml, and most preferably about or less than 5 µg/ml of the given antibody is sufficient to obtain the same results as described in FIG. 1.

Alternatively, the antibody of the present invention is a monoclonal antibody or antigen-binding fragment thereof, which competes for binding to an extracellular epitope of Hsp70 with an antibody provided by the present invention. Those antibodies may be murine as well; however, human, humanized, xenogeneic, or chimeric human-murine antibodies being preferred, in particular for therapeutic applications. An antigen-binding fragment of the antibody can be, for example, a single chain Fv fragment, an F(ab') fragment, an F(ab) fragment, and an F(ab')$_2$ fragment. Thus, for some applications only the variable regions of the antibodies are required, which can be obtained by treating the monoclonal antibody isolated from the hybridoma with suitable reagents so as to generate Fab', Fab, or F(ab")$_2$ portions. Such fragments are sufficient for use, for example, in immunodiagnostic procedures involving coupling the immunospecific portions of immunoglobulins to detecting reagents such as radioisotopes.

Naturally, the invention extends to the hybridoma producing antibodies according to the invention as well. Thus, the invention advantageously provides an indefinitely prolonged cell source of a monoclonal antibody of the invention: the hybridoma. Particularly preferred is a hybridoma selected from the group consisting of hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or cmHsp70.2, deposited with the DSMZ—Deutsche Sammlung von Mikroorganismen und Zellkulturen GmbH on Nov. 14, 2003, and assigned Accession Number DSM ACC2670.

As an alternative to obtaining immunoglobulins directly from the culture of hybridomas, the immortalized hybridoma cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogues as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

In accordance with the above, the present invention also relates to a polynucleotide encoding at least a variable region of an immunoglobulin chain of the antibody described above. Typically, said variable region encoded by the polynucleotide comprises at least one complementarity determining region (CDR) of the $V_H$ and/or $V_L$ of the variable region of the antibody produced by any one of the above described hybridomas. The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs". The CDRs contained in the variable regions of the antibody of the invention can be determined, e.g., according to Kabat, Sequences of Proteins of Immunological Interest (U.S. Department of Health and Human Services, third edition, 1983, fourth edition, 1987, fifth edition 1990 and updates thereof). The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described herein above. The person skilled in the art will readily appreciate that using the variable domains or CDRs described herein antibodies can be constructed according to methods known in the art, e.g., as described in EP-A10 451 216 and EP-A10 549 581. Furthermore, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat. Thus, the present invention also relates to antibodies wherein one or more of the mentioned CDRs comprise one or more, preferably not more than two amino acid substitutions.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions.

Thus a vector comprising said polynucleotide, optionally in combination with a polynucleotide that encodes the variable region of the other immunoglobulin chain of said antibody is a preferred embodiment of the invention Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979).

Once the appropriate genetic material is obtained and, if desired, modified to encode an analogue, the coding sequences, including those that encode, at a minimum, the variable regions of the heavy and light chain, and inserted into an appropriate expression system, i.e. a vector which can be transfected, the antibody or fragment thereof may be expressed recombinantly in host cells. A variety of such host cells may be used; for efficient processing, however, mammalian cells are preferred. Typical mammalian cell lines useful for this purpose include CHO cells, 293 cells, or NSO cells.

A host cell comprising a polynucleotide or a vector according to the invention is thus a preferred embodiment. Vectors may be plasmids, cosmids, viruses and bacteriophages used conventionally in genetic engineering. Apart from a polynucleotide encoding a variable domain of an immunoglobulin chain of an antibody of the invention; they may optionally comprise a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well known methods, which vary depending on the type of cellular host. For example, calcium chloride transfection is commonly utilized for prokaryotic cells, whereas calcium phosphate treatment or electroporation may be used for other cellular hosts; see Sambrook, supra.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

The present invention also provides a method for preparing an antibody that binds to an extracellular localized epitope of Hsp70 on tumor cells, or a functional fragment or immunoglobulin chain(s) thereof, thereof, said method comprising
(a) culturing a cell described above; and
(b) isolating said antibody or functional fragment or immunoglobulin chain(s) thereof from the culture.

The expression systems are preferably designed to include signal peptides so that the resulting antibodies are secreted into the medium; however, intracellular production is also possible.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporeally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

Furthermore, the present invention relates to a method of obtaining antibodies from hybridomas comprising a novel purification protocol as outlined in example 2. While common purification protocols may be used for obtaining antibodies of the invention, they may be less effective than the method described in example 2. Historically, Protein A has been the preferred method of immunoglobulin purification. However, there are certain types of antibodies, such as the single-chain antibodies IgE, IgY and IgM that cannot be purified using the Protein A. An alternative method of immunoglobulin purification, thiophilic adsorption chromatography, is ideal for these types of applications, as well as immunoglobulin purification in general. For general references relating to protein purification procedures including purification of immunoglobulins see for example the booklet from BD Biosciences Clontech, Pablo Alto, Calif., USA, www.clontech.com. Based on previous methods using thiophilic agarose a novel purification protocol has been established in accordance with the present invention, which is particularly suitable for obtaining antibodies of the type IgG1, IgG2a and IgM from hybridomas, particular those hybridomas producing antibodies of the present invention being described herein. However, it is to be understood that the novel method for the purification of antibodies is generally applicable and thus is also subject of the present invention. For experimental details, see example 2. In this respect, it is also to be understood that methods for obtaining antibodies including the purification protocol as described in example 2, which may have minor modifications, e.g., in the composition of the respective buffers, wherein a deviation of +/−10% of the concentration of the different ingredients may be tolerable, are also encompassed in the scope of the present invention as well. Furthermore, the present invention relates to antibodies obtained by the novel method described herein as well as to binding fragments of such antibodies. Naturally, the present invention also extends to derivatives of such antibodies and binding fragments such as those described herein.

As mentioned before, the immunoglobulin or its encoding cDNAs may be further modified. Thus, in a further embodiment the method of the present invention comprises any one of the step(s) of producing a chimeric antibody, humanized antibody, single-chain antibody, Fab-fragment, bi-specific antibody, fusion antibody, labelled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogeneic antibodies. The general principle for the production of xenogeneic antibodies such as human antibodies in mice is described in, e.g., WO 91/10741, WO 94/02602, WO 96/34096 and WO 96/33735. As discussed above, the antibody of the invention may exist in a variety of forms besides complete antibodies; including, for example, Fv, Fab and F(ab)$_2$, as well as in single chains; see, e.g., WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., WO00/30680 for corresponding technical details.

Additionally, the present invention encompasses small polypeptides including those containing a Hsp70 binding fragment as described above, for example containing the CDR3 region of the variable region of any one of the mentioned monoclonal antibodies. Such peptides may easily be synthesized or produced by recombinant means to produce a Hsp70 binding agent useful according to the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide. The sequence of the CDR regions, for use in synthesizing peptide Hsp70 binding agents, may be determined by methods known in the art. The heavy chain variable region is a peptide which generally ranges from 100 to 150 amino acids in length. The light chain variable region is a peptide which generally ranges from 80 to 130 amino acids in length. The CDR sequences within the heavy and light chain variable regions which include only approximately 3-25 amino acids may easily be sequenced by one of ordinary skill in the art. The peptides may even be synthesized by commercial sources.

To determine whether a peptide binds to Hsp70 any known binding assay may be employed. For example, the peptide may be immobilized on a surface and then contacted with labeled Hsp70. The amount of Hsp70 which interacts with the peptide or the amount which does not bind to the peptide may then be quantitated to determine whether the peptide binds to Hsp70. A surface having the aforementioned anti-Hsp70 monoclonal antibodies immobilized thereto may serve as a positive control.

Screening of Hsp70 binding agents also can be carried out utilizing a competition assay. If the Hsp70 binding agent being tested competes with an anti-Hsp70 monoclonal antibody of the present invention, as shown by a decrease in binding of the monoclonal antibody, then it is likely that the agent and the anti-Hsp70 monoclonal antibody bind to the same, or a closely related, epitope. Still another way to determine whether an agent has the specificity of the anti-Hsp70 monoclonal antibodies described above is to pre-incubate the monoclonal antibody with Hsp70 with which it is normally reactive (i.e., binds), and then add the agent being tested to determine if the agent being tested is inhibited in its ability to bind Hsp70. If the agent being tested is inhibited then, in all likelihood, it has the same or a functionally equivalent epitope and specificity as the anti-Hsp70 monoclonal antibodies.

Using routine procedures known to those of ordinary skill in the art, one can determine whether a Hsp70 binding agent is useful according to the invention by determining whether the agent is one which modulates T cell proliferation or cytotoxicity in an in vitro assay such as measuring release of TNF from T cells or by $^{51}$Cr release assay; see, e.g., Herin et al., Int. J. Cancer 39 (1987), 390-396. Other assays are described in the Examples and elsewhere herein; see also WO02/22656.

The polypeptides (e.g. antibodies) and other Hsp70 binding agents described above can also be used immunotherapeutically for disorders in humans. The term "immunotherapeutically" or "immunotherapy" as used herein in conjunction with the Hsp70 binding agents denotes both prophylactic as well as therapeutic administration. Thus, the peptides can be administered to high-risk subjects in order to lessen the likelihood and/or severity of a disease such as a tumor, or infectious disease, or administered to subjects already evidencing such diseases.

Hsp70 binding agents which increase or decrease NK cell activity can be selected using the assays described, for example, in WO02/22656 and according to standard killer cell cytotoxicity and proliferation assays, such as mixed lymphocyte reactions, chromium release assays, TNF release assays, and thymidine incorporation assays. It is believed that a monovalent Hsp70 binding agent, for example derivatives of single chain antibodies which have only one binding domain of the original antibody, will inhibit the stimulatory signal of Hsp70 by reducing Hsp70 polypeptides expressed by target cells.

Hence, the present invention relates to any antibody and similar binding molecules, which preferably have substantially the same immunological binding characteristics as monoclonal antibodies cmHsp70.1 or cmHsp70.2, i.e. which recognize the same epitope and with substantially the same affinity, or at least 1/10 of the affinity as the antibodies of the invention exemplified herein. Such antibodies and binding molecules can be tested for their binding specificity and affinity by for example by using competitive assays with an antibody produced by a hybridoma of the invention. The antibodies of the present invention will typically find use individually in treating substantially any disease susceptible to monoclonal antibody based therapy. In particular, the immunoglobulins can be used as immunosuppressive agents. For an antibody of the invention, typical disease states suitable for treatment include inflammatory symptoms. The antibodies can be used therapeutically in, e.g., patients suffering an diseases related to immune response; see supra. Such therapy can be accomplished by, for example, the administration of antibodies of the invention.

Such administration can utilize unlabeled as well as labeled antibodies or antigens. Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., WO 94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The above described fusion protein may further comprise a cleavable linker or cleavage site for proteinases. These spacer moieties, in turn, can be either insoluble or soluble (Diener et al., Science 231 (1986), 148) and can be selected to enable drug release from the antigen at the target site. Examples of therapeutic agents which can be coupled to the antibodies, antigens and epitopes of the invention for immunotherapy are drugs, radioisotopes, lectins, and toxins. The drugs with which can be conjugated to the antibodies, antigens and epitopes of the invention include compounds which are classically referred to as drugs such as mitomycin C, daunorubicin, and vinblastine. In using radioisotopically conjugated antibodies, antigens or epitopes of the invention for, e.g., immunotherapy, certain isotopes may be more preferable than others depending on such factors as leukocyte distribution as well as stability and emission. Depending on the autoimmune response, some emitters may be preferable to others. In general, α and β particle emitting radioisotopes are preferred in immunotherapy. Preferred are short range, high energy α emitters such as $^{212}$Bi. Examples of radioisotopes which can be bound to the antibodies, antigens or epitopes of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody, antigen or epitope of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or the corresponding vectors instead of the proteinaceous material itself.

As described above, the polynucleotide of the invention can be used alone or as part of a vector to express the (poly) peptide of the invention in cells. In principle this also enables gene therapy of diseases related to inappropriate expression of Hsp70 on the plasma membrane. For example, it is envisaged to introduce a polynucleotide or a vector of the invention into a cell of the immune system, preferably a cytotoxic killer cell in order to enable the cell to express a receptor comprising the binding domain of an antibody of the present invention, which renders the cell capable of recognizing specifically tumor cells or other diseased cells, which express Hsp70 on their cell surface. The polynucleotides or vectors of the invention are introduced into the cells which in turn produce the antibody or corresponding receptor molecules. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Plasma membrane bound Hsp70 interacts with other cell surface molecules, and it is reasonable to assume that agents modulating these interactions will have beneficial, additive and preferably synergistic effects on the treatment of diseases and conditions, wherein either of these proteins are involved in. Furthermore, such agents are expected to be useful in diagnosis, where the presence or absence of either of said proteins is associated with said disease or condition. Accordingly, the present invention also provides novel bi- or multi-functional molecules that comprise the binding domain of an antibody according to the invention, an immunoglobulin chain thereof or a binding fragment thereof which bind cell surface membrane-bound heat shock protein (HSP70), and at least one further functional domain; see also supra. In a preferred embodiment said bi- or multifunctional molecule is bispecific molecule, particularly preferred a bispecific antibody.

The term "bispecific molecule" includes molecules which have at least the two mentioned binding domains directly or indirectly linked by physical or chemical means. However, the bispecific molecule of the present invention may comprise further functional domains such as additional binding domains and/or moieties such as a cytotoxic agent or a label and the like; see also supra.

Means and methods for the preparation of multivalent, multispecific molecules having at least one specificity for a desired antigen are known to the person skilled in the art. For example, WO99/59633 describes multimeric molecules with at least one specificity for the HLA class II invariant chain (Ii) and their use for the clearance of therapeutic or diagnostic agents, autoantibodies, anti-graft antibodies, and other undesirable compounds. As used herein, unless otherwise indicated or clear from the context, antibody or binding domains, regions and fragments are accorded standard definitions as are well known in the art; see, e.g., Abbas et al., Cellular and Molecular Immunology (1991), W. B. Saunders Company, Philadelphia, Pa.

Certain bispecific molecules of the present invention are used for binding to antigen or to block interaction of a protein and its ligand; their use to promote interactions between immune cells and target cells however is preferred. Finally, antigen-binding molecules of the invention are used to localize immune cells, tumor cells, infected cells, anti-tumor agents, target moieties, reporter molecules or detectable signal producing agents to an antigen of interest.

Bispecific molecules of the invention can cross-link antigens on target cells with antigens on immune system effector cells. This can be useful, for example, for promoting immune responses directed against cells which have a particular antigens of interest on the cell surface. According to the invention, immune system effector cells include antigen specific cells such as T cells which activate cellular immune responses and nonspecific cells such as macrophages, neutrophils and natural killer (NK) cells which mediate cellular immune responses. Hence, bispecific molecules of the invention can have a further binding site for any cell surface antigen of an immune system effector cell. Such cell surface antigens include, for example, cytokine and lymphokine receptors, Fc receptors, CD3, CD16, CD28, CD32, CD64 and CD94. In general, antigen binding sites are provided by scFvs which are derived from antibodies to the aforementioned antigens and which are well known in the art. Antigen-binding sites of the invention which are specific for cytokine and lymphokine receptors can also be sequences of amino acids which correspond to all or part of the natural ligand for the receptor. For example, where the cell-surface antigen is an IL-2 receptor, an antigen-binding protein of the invention can have an antigen-binding site which comprises a sequence of amino acids corresponding to IL-2. Other cytokines and lymphokines include, for example, interleukins such as interleukin-4 (IL-4), interleukin-5 (IL-5), interleukin-15 (IL-15) and colony-stimulating factors (CSFs) such as granulocyte-macrophage CSF (GM-CSF), and granulocyte CSF (G-CSF).

In addition, any one of the described bispecific molecules may contain a binding domain binding FcgammaRI on activated effector cells. The clinical potential of this approach for the treatment of tumors such as B cell malignancies looks most attractive. Triggering of antitumor immunity by expression of anti-FcgammaR scFv on cancer cell surface has been described by Gruel et al., Gene Ther. 8 (2001), 1721-1728.

In addition or alternatively, the bispecific molecule of the invention may comprise a binding domain binding CD3. This embodiment is particularly useful for the treatment of carcinoma; see, e.g., Riesenberg et al., J. Histochem. Cytochem. 49 (2001), 911-917, which report on the lysis of prostate carcinoma cells by trifunctional bispecific antibodies (alpha EpCAMxalpha CD3).

These and other combinations of functional domains in the bispecific molecule of the present invention and uses thereof are encompassed by the present invention.

In a preferred embodiment, the bispecific molecule of the present invention is a bispecific antibody. The bispecific antibodies may comprise Fc constant regions, for example for association of the polypeptide chains comprising the binding domains. In addition to providing for association of the polypeptide chains, Fc constant domains contribute other immunoglobulin functions. The functions include activation of complement mediated cytotoxicity, activation of antibody dependent cell-mediated cytotoxicity and Fc receptor binding. When antigen-binding proteins of the invention are administered for treatment or diagnostic purposes, the Fc constant domains can also contribute to serum halflife. The Fc constant domains can be from any mammalian or avian species. When antigen binding proteins of the invention are used for treatment of humans, constant domains of human origin are preferred, although the variable domains can be non-human. In cases where human variable domains are preferred, chimeric scFvs can be used. Further means and methods for the production of bispecific antibodies are described in the art; see, e.g., WO97/14719 which describes a process for producing bispecific or bivalent double head antibody fragments, which are composed of a binding complex containing two polypeptide chains, and WO01/80883. Furthermore, the bispecific molecules of the invention can be optimized in their avidity for antigen(s) while maintaining their ability to function as a natural antibody, including the ability to activate complement mediated cytotoxicity and antibody dependent cellular toxicity; see, e.g., WO01/90192.

Furthermore, the present invention relates to a composition comprising, the antibody, the bi- or multifunctional molecule, the polynucleotide or the above described vector or cell of the invention. The composition of the present invention may further comprise a pharmaceutically acceptable carrier.

Additionally moieties may be added that improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition. Furthermore, the pharmaceutical composition may also be formulated as a vaccine, for example, if the pharmaceutical composition of the invention comprises a bispecific molecule described above for passive immunization.

Therapeutic or diagnostic compositions of the invention are administered to an individual in a therapeutically effective dose sufficient to treat or diagnose disorders as mentioned above. The effective amount may vary according to a variety of factors such as the individual's condition, weight, sex and age. Other factors include the mode of administration. The pharmaceutical compositions may be provided to the individual by a variety of routes such as by intracoronary, intraperitoneal, subcutaneous, intravenous, transdermal, intrasynovial, intramuscular or oral routes. In addition, co-administration or sequential administration of other agents may be desirable. A therapeutically effective dose refers to that amount of active molecule of the invention sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The pharmaceutical composition of the present invention further comprises an immune stimulatory agent in a preferred embodiment Immune stimulatory agents are used to enhance an immune reaction or to induce an immune reaction against epitopes which do not trigger an humoral or cytotoxic defence reaction under normal conditions. Such agents are well known in the art and can be chosen from a wide variety of molecules such as co-stimulatory molecules, e.g. cytokines and/or adjuvants.

An "adjuvant" refers to a substance that enhances an immune response, including, for example, but not limited to, an antigen's immune-stimulating properties or the pharmacological effect(s) of a compound or drug. An adjuvant may non-specifically enhance an immune response, e.g., the immune response to an antigen. "Freund's Complete Adjuvant," for example, is an emulsion of oil and water containing an immunogen, an emulsifying agent and mycobacteria. Another example, "Freund's incomplete adjuvant," is the same, but without mycobacteria. An adjuvant may comprise oils, emulsifiers, killed bacteria, aluminum hydroxide, or calcium phosphate (e.g., in gel form), or combinations thereof. An adjuvant may be administered into a subject (e.g., via injection intramuscularly or subcutaneously) in an amount sufficient to produce antibodies. Comparison of the effect of different immunological adjuvants on the antibody and T-cell response to immunization with MUC1-KLH and GD3-KLH conjugate cancer vaccines in the mouse has been described in Kim et al., Vaccine 18 (1999), 597-603. In this publication also ELISA assays for IgM and IgG antibody responses as well as proliferation and cytokine release (IFN-gamma and IL-4) for T-cell responses are described, which can also be performed in accordance with the present invention.

The present invention also refers to a diagnostic composition comprising an antibody, a bi- or multifunctional molecule, a polynucleotide, a vector or a cell according to the invention; and optionally reagents conventionally used in immuno or nucleic acid based diagnostic methods. For use in diagnosis, a variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology", Academic Press, London (1987), or in the series "Methods in Enzymology", Academic Press, Inc. There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, random priming, nick-translations, tailing (using terminal transferases) are well known in the art. Detection methods comprise, but are not limited to, autoradiography, fluorescence microscopy, direct and indirect enzymatic reactions, etc.

In addition, the above described compounds etc. may be attached to a solid phase. Solid phases are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing bispecific molecules of the invention on solid phases include but are not limited to ionic, hydrophobic, covalent interactions and the like. The solid phase can retain one or more additional receptor(s) which has/have the ability to attract and immobilize the region as defined above. This receptor can comprise a charged substance that is oppositely charged with respect to the reagent itself or to a charged substance conjugated to the capture reagent or the receptor can be any specific binding partner which is immobilized upon (attached to) the solid phase and which is able to immobilize the reagent as defined above. Commonly used detection assays can comprise radioisotopic or non-radioisotopic methods. These comprise, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemiluminescent Immune Assay). Other detection methods that are used in the art are those that do not utilize tracer molecules. One prototype of these methods is the agglutination assay, based on the property of a given molecule to bridge at least two particles.

Nucleic acid based diagnostic format are also well known to the person skilled in the art and include, but are not limited to, hybridization of Southern or Northern blots, PCR, sequencing, RFLP and SSCP analyses.

The present invention also relates to a kit comprising an antibody or a bispecific molecule of the invention. Such kits are useful for a variety of purposes including but not limited to forensic analyses, diagnostic applications, and epidemiological studies in accordance with the above described diseases and disorders. Such a kit would typically comprise a compartmentalized carrier suitable to hold in close confinement at least one container. The carrier would further comprise reagents for detection such as labeled antigen or enzyme substrates or the like.

Figure 3:
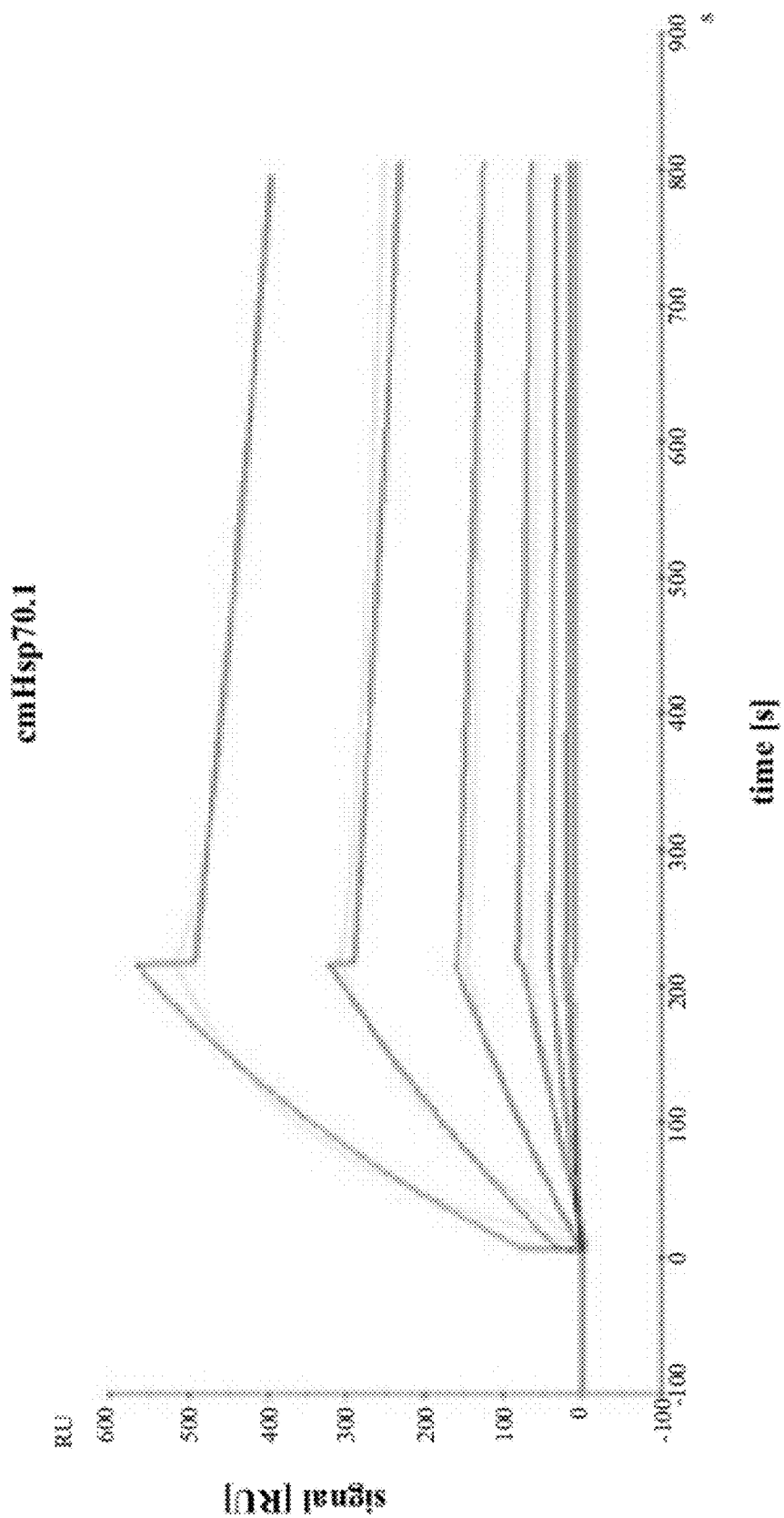
FIG. 3: Global kinetic analysis of cmHsp70.1 mAb binding human Hsp70 using a Biacore. Purified human Hsp70 protein was diluted to final concentrations of 0.78 nM, 1.6 nM, 3.1 nM, 6.3 nM, 12.5 nM, 25 nM, 50 nM and injected onto a cmHsp70.1 mAb-coated gold surface. Relative Response (RR) units were analyzed using BIAevaluation software 4.1. Kinetic constants were $k_{on}=6.99\times10^4$ M$^{-1}$s$^{-1}$, $K_{off}=3.79\times10^{-4}$ s$^{-1}$ and a $K_D=5.4$ nM with a Chi$^2=59.4$, respectively. Gray colored lines contrast the measured data from the simulated fits (black).

Despite the relatively low density of Hsp70 molecules that are presented on the cell surface of CT26 mouse tumor cells (approximately 10,000 per cell) and the fact that the IgG1 isotype has a low capacity to induce ADCC (18) and CDC (19) in mice, the antibodies of the present invention exemplified by cmHsp70.1 mAb mediates specific killing in membrane Hsp70 positive CT26 tumors in vitro as well as in vivo wherein binding to the tumor is highly specific as shown in Examples 7 o 9 and the corresponding FIGS. 5 to 7. In addition, the antibody of the present invention exemplified by the Hsp70.1 exhibit a a Kd=5.4 nM, i.e. high affinity for the human recombinant Hsp70 as shown in FIG. 3 and Example 5. Furthermore, the antibody of the present invention is capable to recognize specifically the Hsp70 cell surface expression of various mouse and human tumor cell lines and tissues in vivo and in vitro as indicated in Table 1 and 2 of the Example 4. Thus, the provision of the above described and deposited hybridomas provide a reliable source of anti-Hsp70 antibodies capable of detecting extracellular epitopes of Hsp70 on viable cells, preferably tumor cells and thereby enabling the specific detection and treatment of cells which display Hsp70 on their cell surface, in particular tumor cells and cells infected by pathogens. Thus, the present invention provides a novel class of anti-Hsp70 antibodies for use in therapy and diagnosis as well as in research in general.

Naturally the present invention also encompasses a method of diagnosing a tumor comprising assaying cells in a sample from a patient with the antibody, or the bi- or multifunctional molecule according to the invention, wherein the presence or increased amount of extracellular localized Hsp70 is indicative for the tumor.

This method preferably comprises an immunological step. Commonly used diagnostic methods employing antibodies and/or bi- or multifunctional molecules are for example immunohistochemistry on frozen or paraffin embedded tissue sections, Western blots, immunoprecipitation etc. Optionally, easy to detect signal producing agents can be used in conjunction with said antibodies or bi- or multifunctional molecules.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible wavelength range, and can be substrates or degradation products of enzyme catalyzed reactions.

As described before, the compositions of the present invention are useful in diagnosis, prophylaxis, vaccination or therapy. Accordingly, the present invention relates to the use of the antibody, the bi- or multifunctional molecule, the nucleic acid molecule or the cell of the present invention for the preparation of a pharmaceutical composition for the treatment of a tumor or modulating an immune response.

For these embodiments, the antibodies or the bi- or multifunctional molecules of the invention can be chemically or biosynthetically linked to anti-tumor agents or detectable signal-producing agents; see also supra. Antitumor agents linked to a bispecific molecule, for example a bispecific antibody, include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods; see, e.g., Hermentin and Seiler, Behring Inst. Mitt. 82 (1988), 197-215. A method of treating a tumor or modulating the immune response in a subject in need thereof, usually comprises administering to the subject a therapeutically effective amount of the antibody or the bi- or multifunctional molecule. As mentioned above, a therapeutically effective dose refers to that amount of active molecule of the invention sufficient to ameliorate the symptoms or condition. Therapeutic efficacy and toxicity of such compounds can be determined by standard pharmaceutical procedures in cell cultures or experimental animals; see also supra.

For the purpose of this invention said pharmaceutical composition is preferably designed to be administered intravenously, intramuscularly, subcutaneously, intraperitoneally, or as an aerosol.

Preferably, the tumor to be treated or diagnosed is selected from the group consisting of carcinomas of lung, colorectum, pancreas, larynx, stomach, head, neck, breast, ovaries, uterine, cervix, liver, peripheral and central nervous system, sarcomas, chronic myeloic leukemia (CML), acute myeloic leukemia (AML), acute lymphatic leukemia (ALL), non Hodgkin Lymphoma (NHL), myeloproliferative syndrome (MPS), myelodysplastic syndrome (MDS), plasmocytoma, melanoma and metastatic cells in general.

Also encompassed by the uses and methods of the present invention are disorders related to an immune response which include, but are not limited to a viral infections, bacterial infections, rheumatoid arthritis, lupus erythematodes, asthma bronchiale etc.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" as employed herein relates to animals in need of amelioration, treatment and/or prevention of a neoplastic or infectious disease. Most preferably said subject is a human.

Since the exclusive expression of Hsp70 on the surface of disease related cells, the invention provides the means for the targeted delivery to these cells while avoiding the normal cells. This is of particular advantage if toxic moieties are linked to a therapeutic molecule as described above. Such a method of targeting a therapeutic and/or diagnostic agent to a cell which expresses an extracellular localized epitope of Hsp70 on the cell surface comprises administering to the subject a therapeutically effective amount of a bi- or multifunctional molecule of the invention. The use of a bi- or multifunctional molecule for targeting a therapeutic and/or diagnostic agent to a cell which expresses an extracellular localized epitope of Hsp70 on the cell surface is, of course, a preferred embodiment of this invention. Said targeted cell can either be preferably a tumor cell or a cell related to an immune disorder or an infectious disease.

From the foregoing, it is evident that the present invention encompasses any use of a ligand binding molecule comprising at least one CDR of the above described antibody, in particular for diagnosing and/or treatment of a disorder related to the expression or malfunction of Hsp70 on the cell surface of target cells, in particular tumor cells or infected cells. Preferably, said ligand binding molecule is an antibody of the present invention or an immunoglobulin chain thereof. In addition, the present invention relates to anti-idiotypic antibodies of any one of the mentioned monoclonal antibodies described hereinbefore. These are antibodies or other binding molecules which bind to the unique antigenic peptide sequence located on an antibody's variable region near the antigen binding site. One concept for immune therapy of cancer involves induction of antigen mimic antibodies to trigger the immune system into a response against the tumor cells. Anti-idiotypic antibodies (Ab2) directed against the antigen-combining site of other antibodies (Ab1) may functionally and even structurally mimic antigen and induce antianti-idiotypic immune response. An example of functional mimicry of an anti-idiotypic antibody to a murine monoclonal immunoglobulin (Ab1), which defines ovarian cancer antigen CA125, is described in Ma et al., Jpn. J. Cancer Res. 93 (2002), 78-84. A murine monoclonal anti-idiotypic antibody as a surrogate antigen for human Her-2/neu is described in Baral et al., Int. J. Cancer 92 (2001), 88 95. Further examples comprise active immunotherapy with anti-idiotypic antibody for patients with nasopharyngeal carcinoma (NPC), described by Li et al., Cancer Biother. Radiopharm. 17 (2002), 673-679 and anti-idiotypic antibodies carrying the "internal image" of peptide YIGSR inhibit spontaneous metastasis of Lewis lung carcinoma in mice described by Koliakos et al. in In Vivo 16 (2002), 511-518. Preferably, the anti-idiotypic antibody is humanized; see also supra.

The biological activity of the antibodies identified here suggests that they have sufficient affinity to make them potential candidates for drug localization to cells expressing the appropriate surface structures. This targeting and binding to cells could be useful for the delivery of therapeutically or diagnostically active agents (including targeting drugs, DNA sequences, RNA sequences, lipids, proteins (e.g., human growth factors)) and gene therapy/gene delivery. Molecules/particles with an antibody of the invention would bind specifically to cells/tissues expressing Hsp70 on the cell surface, and therefore could have diagnostic and therapeutic use. Thus, the antibody or the antigen of the present invention can be labeled (e.g., fluorescent, radioactive, enzyme, nuclear magnetic) and used to detect specific targets in vivo or in vitro including "immunochemistry" like assays in vitro. In vivo they could be used in a manner similar to nuclear medicine imaging techniques to detect tissues, cells, or other material expressing Hsp70, in particular on the cell surface of target cells. Another method involves delivering a therapeutically active agent to a patient. The method includes administering at least one antibody or the antigen-binding fragment and the therapeutically active agent to a patient. Preferably, the therapeutically active agent is selected from drugs, DNA sequences, RNA sequences, proteins, lipids, and combinations thereof. More preferably, the therapeutically active agent is an antibacterial agent, anti-inflammatory agent, or antineoplastic agent.

The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, Int. J. Cancer Surp. SuDP 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, J. Infect Disease 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, Cancer Treat. Res. 68 (1993), 181-194 and by Fanger, Crit. Rev. Immunol. 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

The invention further contemplates linking molecules of the invention to target or reporter moieties. Target moieties are first members of binding pairs. Anti-tumor agents, for example, are conjugated to second members of such pairs and are thereby directed to the site where the antigen-binding protein is bound. A common example of such a binding pair is adivin and biotin. Biotin can be conjugated to an molecule of the invention, and thereby provides a target for an anti-tumor agent or other moiety which is conjugated to avidin or streptavidin. Alternatively, biotin or another such moiety is linked to a molecule of the invention and used as a reporter, for example in a diagnostic system where a detectable signal-producing agent is conjugated to avidin or streptavidin. Suitable radioisotopes for use as anti-tumor agents are also known to those skilled in the art. For example, $^{131}$I or $^{211}$At is used. These isotopes are attached to the antibody using conventional techniques; see, e.g., Pedley et al., Br. J. Cancer 68 (1993), 69-73. Alternatively, the anti-tumor agent which is attached to the antibody is an enzyme which activates a prodrug. In this way, a prodrug is administered which remains in its inactive form until it reaches the tumor site where it is converted to its cytotoxic form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4), interleukin-15 (IL-15) or tumor necrosis factor alpha (TNF-α). The antibody targets the cytokine to the tumor so that the cytokine mediates damage to or destruction of the tumor without affecting other tissues. The cytokine is fused to the antibody at the DNA level using conventional recombinant DNA techniques.

By a further embodiment as mentioned before, the ligand binding molecules and antibodies of the invention may also be used in a method for the diagnosis of Hsp70-related diseases in an individual by obtaining a body fluid sample from the tested individual which may be a blood sample, a lymph sample or any other body fluid sample and contacting the body fluid sample with an antibody of the invention under conditions enabling the formation of antibody-antigen complexes. Similarly, biopsy or other specimen may be taken common in tumor diagnostic. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the antibody or the antigen of the invention.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. Particularly useful means and methods for the recombinant production of bispecific molecules are described in WO94/13804, WO01/80883 and WO01/90192. All references mentioned herein are incorporated in their entirety.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Experimental Procedures

Human and Mouse Tumor Cell Lines

The CX2 human colon adenocarcinoma cell line and the MCF-7, MDA436 human breast carcinoma cell lines are purchased by the Tumorbank DKFZ, Heidelberg, Germany. The melanoma cell lines Malme, Mel Ei, Mel Ho, Parle, A375 and Sk Mel$_{29}$, (kindly provided by Judith Johnson, Institute of Immunology, LMU München) are cultured as described elsewhere (31). The tumorigenic CT26 mouse colon adenocarcinoma (CT26.WT; ADCC CRL-2638) [19], 1048 mouse pancreatic carcinoma (kindly provided by Dieter Saur, Department of Medicine II, Technische Universität München, A20 B cell lymphoma [20], ADJ plasmocytoma cell lines, all derived from BALB/c mouse strains, the B16/F10 malignant mouse melanoma cells (C57/B16 mouse strain), and the MOS162 osteosarcoma cell line (C3H mouse strain; kindly provided by Dr. Michael Rosemann, HMGU Munich) were maintained in DMEM or RPMI 1640 medium supplemented with 10% v/v heat-inactivated fetal calf serum (FCS), 2 mM L-glutamine, 1 mM sodium-pyruvate and antibiotics (100 IU/ml penicillin, 100 μg/ml streptomycin), at 37° C. in 5% $CO_2$. Cell lines were maintained in the exponential growth phase by regular cell passages twice a week and sub-cultivation at a ratio of 1:5 (seeding of $1\times10^6$ cells in 5 ml fresh culture medium). Doubling-time of the cell lines was approximately 20 h. Single cell suspensions were derived by short-term (less than 1 min) 0.25% (w/v) Trypsin 0.53 mM EDTA treatment. All cell culture reagents were purchased from Life Technologies, Rockville, Calif.

Human Primary Tumors and Corresponding Normal Tissues

Tumor specimen and corresponding normal tissues were obtained from patients undergoing surgical removal of their tumors at the University Regensburg, Germany between February 2002 and January 2004. Briefly, fresh biopsy material is washed in antibiotic (penicillin/streptomycin)—containing Dulbecco's modified Eagle's medium (DMEM) and single cell suspensions are prepared by mincing the tissue and forcing it through a sterile mesh. In parallel, tumor cell lines are established (successful for approximately 40% of all samples). The corresponding normal tissue was derived from the same patients at a distance of at least 0.2 cm from the tumor. The study was approved by the Institutional Review Board of the Medical Faculty of the University Hospital Regensburg, Germany and all patients included in the study provided signed informed consent.

Flow Cytometry

The Hsp70 membrane phenotype in mouse tumor cell lines was determined by flow cytometry using the FITC-conjugated cmHsp70.1 mAb (IgG1; multimmune, Munich, Germany). The membrane Hsp70 phenotype of freshly isolated, viable human tumor and normal cells, and of human and mouse tumor cell lines was determined by flow cytometry using either the FITC-conjugated cmHsp70.1 mAb (IgG1; multimmune GmbH, Munich, Germany) which is directed against the extracellularly exposed sequence of membrane Hsp70 or the SPA810 mAb (IgG1; Stressgen via Assay Designs, Ann Arbor, Mich., U.S.A.). For the CT26 mouse colon carcinoma cells as well the above mentioned ones, the Hsp70 status was routinely determined before their injection into the mice, and on single cell suspensions of random tumor samples after explantation on day 14. Briefly, after incubation of viable cells ($0.2\times10^6$ cells) with the appropriate antibody for 30 min at 4° C. and following two washing steps, 7-AAD negative, viable cells were analyzed on a FACSCalibur flow cytometer (Becton Dickinson, Heidelberg, Germany). An IgG1 isotype-matched control antibody was used to determine non-specific staining of the cell lines. The proportion of positively stained cells was defined as the difference of the number of cells stained with the relevant antibody minus the number of cells stained with the appropriate isotype-matched control immunoglobulin. Blocking of the antibody binding was performed by a co-incubation of viable tumor cells ($0.2\times10^6$ cells) with cmHsp70.1-FITC mAb (5 μg/mL) and an excess of "TKD" or "NGL" peptide (12.5 and 25 μg/mL). Following an incubation period of 30 min at 4° C., cells were washed and analyzed by flow cytometry, as described above.

Fluorescence Microscopy and Kinetics of Uptake of mAb cmHsp70.1-FITC

Microscopic immunofluorescence studies were performed with CT26 tumor cells which were cultured in 8-well chamber slides (Nunc, Rochester, N.Y., USA) at a cell density of 20,000 cells/well. After two washing steps in phosphate-buffered saline (PBS), viable cells were incubated for 30 min with cmHsp70.1-FITC mAb either at 4° C. or at 37° C. After fixation and permeabilization the cells were incubated with antibodies directed against Rab4, Rab5a, Rab7, Rab9, Rab11 (all obtained from Santa Cruz Biotechnology, CA, USA), LAMP1, LAMP2 (kindly provided by Prof Stefan Höning, University of Cologne, Germany) for 1 h and with the appropriate Cy3-conjugated secondary antibodies (anti-rabbit-Cy3 and anti-goat-Cy3, Jackson ImmunoResearch, West Grove, Pa., USA) for 30 min. Cells were then washed twice in PBS and mounted in Vectashield containing DAPI solution (Vector Laboratories, Burlingame, Calif., USA). The slides were analyzed on a Zeiss Axioscop 2 plus scanning microscope (Zeiss, Jena, Germany) equipped with a ×100 oil-immersion objective and standard filters. Photographs of representative cells are shown; the localization and co-localization of Hsp70 and early (Rab4, Rab5a), late (Rab7, Rab11), trans golgi network, recycling endosomal (Rab11) and lysosomal (LAMP1, LAMP2) markers were visualized in green (FITC), red (Cy3) and yellow (merge) spectra. The uptake of cmHsp70.1-FITC mAb and the identically labelled IgG1-FITC control antibody into tumor cells was measured by flow cytometry. For this, the tumor cells were incubated with the mAb for 2, 5, 10, 15, 30, and 60 min either at 4° C. or at 37° C. After two washing steps, viable cells were gated and analyzed, as described above.

Flow Cytometry of Effector Cells

The proportion of lymphocyte subpopulations, monocytes, granulocytes and their expression of the activation marker CD25 (α chain of the IL-2 receptor) in the unstimulated and TKD/IL-2-stimulated effector cell populations which were used for the ADCC assays was determined by flow cytometry using FITC/PE-labeled mAb directed against CD4, CD8, CD205, CD11c, Ly6G/Ly6C (Gr-1), B220, CD11b, CD49b, CD56 and CD25 (BD Biosciences, Heidelberg; Germany). The staining procedure has been described above.

Biacore Analysis

Kinetic measurements were performed using a Biacore X instrument (Biacore AB, Uppsala, Sweden) at 25° C. with a CMS chip (GE) and 25 mM HEPES, 150 mM KCl, 5 mM $MgCl_2$ pH 7.6 as running buffer and at a flow rate of 10 µl/min. For this assay, 70 µg/ml cmHsp70.1 mAb diluted in 20 mM acetate (pH 4.8) was covalently coupled to a CMS chip surface with primary amine groups using a standard amine coupling method, which yielded in about 1700 RU. The second channel subjected to the same activation and deactivation treatments, but without the antibody was used as control. Solutions of human Hsp70 (0.78-50 nM) were prepared in running buffer and tested for binding. To determine the binding constants, association ($K_{on}$) and dissociation ($K_{off}$) phase data from each concentration were globally fitted to a simple 1:1 interaction model (A+B=AB) using the BIAevalution software 4.1.

Animals

Female and male BALB/c mice were obtained from an animal breeding colony (Harlan Winkelmann, Borchen, Germany) and maintained in pathogen-free, individually ventilated cages (Tecniplast, Hohenpeissenberg, Germany). Animals were fed with sterilized, laboratory rodent diet (Meika, Großaitingen, Germany) and were used for experiments between 6 and 12 weeks of age. All animal experiments were approved by the "Regierung von Oberbayern" (55.2-1-54-2531-30-07; 55.2-1-54-2531-52-07) and were performed in accordance with institutional guidelines.

Intraperitoneal (i.p.) and Subcutaneous (s.c.) Injection of Tumor Cells

CT26 tumor cells were thawed from a common frozen stock and cultured in vitro for 2 to 3 days before use. BALB/c mice were injected into the peritoneum (i.p.) or s.c. with 100 µl of the CT26 stock solution containing $2.5\times10^4$ cells, or $8\times10^5$ A20 cells (23) using a 1,000 µl plastic syringe with a 22-gauge needle. Injection was visually controlled using a 7× Stereomicroscope (Zeiss, Göttingen, Germany) and tumor weights of single tumors were determined on days 4, 6, 8, 10, 12, 14, 19, and 21 after injection. From day 23 onwards, mice died from progressive tumor growth.

Injection of the Antibodies

For intraoperative and near-infrared fluorescence imaging 100 µg cmHsp70.1 mAb or IgG1 isotype-matched control antibody (clone EM21, directed against O6-ethyl-2-deoxyguanosine) conjugated to Cy5.5—NHS (Squarix GmbH, Marl, Germany) at dye to molar ratios of 0.74 and 1.02, respectively, were injected i.v. into tumor-bearing mice on day 14. As an alternative, both antibodies were labelled with fluorescein isothiocyanate (FITC) at identical fluorescence intensities, as determined on the multilabel Reader Victor X4 (Perkin Elmer, Rodgau-Jügesheim, Germany).

Injection of Antibodies and the 14-mer Hsp70 Peptide "TKD"

For the immunotherapeutic approach, mice were injected i.v. with unconjugated cmHsp70.1 mAb (20 µg mAb per injection) or a non-binding IgG1 isotype-matched control antibody on days 3, 5 and 7 after the injection of CT26 cells ($2.5\times10^4$). For the inhibition assays, 20 µg cmHsp70.1 mAb was co-injected with an excess of the 14-mer Hsp70-peptide TKD (TKDNNLLGRFELSG; 50 µg/mL per injection; purity>97%, EMC microcollections GmbH, Tübingen, Germany) on days 3, 5 and 7 after tumor cell injection (i.p.). All mice were sacrificed on day 14 after tumor cell injection.

Intraoperative Fluorescence Imaging

For intraoperative imaging, mice were sacrificed 30 min, 2, 4, and 8 h after i.v. injection of either cmHsp70.1 mAb or control IgG1 (100 µg per injection) labelled with Cy5.5. The fluorescence imaging measurements used a back illuminated EM-CCD camera (iXon DV887, Andor, Belfast, Northern Ireland). Light from the tissue was collected using a variable zoom objective lens (NT58-240, Edmund Optics). Light collected by the objective was filtered using a 710/10 nm band pass filter. A 670 nm CW diode laser (B&W Tek, Newark, Del., USA) with maximum power 300 mW was used for the excitation. The laser light beam was guided through a multi-mode fiber (200 µm core/0.22 NA) to a collimator and a diffuser (F260SMA-b, ED1-S20, Thorlabs, Newton, N.J., USA) for beam expansion and uniform illumination. A 24 bit color CCD camera (PCO AG, Donaupark, Kelheim, Germany) coupled with the same objective lens was used to obtain color images of the measured tissue. A 250 W halogen lamp (KL-2500 LCD, Edmund Optics, Barrington, N.J., USA) was used for white light illumination.

Autopsy

Control mice and cmHsp70.1 mAb-treated mice were sacrificed by craniocervical dislocation. The peritoneal cavity was macroscopically inspected for tumor dissemination and the primary tumors were excised in total. The weight of each primary colon tumor was measured separately.

Immunofluorescence Studies of Tissue Sections

On day 14, CT26 tumor-bearing mice were injected i.v. either with Cy5.5- or FITC-labelled cmHsp70.1 mAb or with identically labelled IgG1 control immunoglobulin (100 µg) into the tail vein. Mice were sacrificed 3, 8, 24 and 72 h after injection of the antibodies and tumors and organs such as liver, lung, kidney, heart and spleen of the mice were collected, cut in 4 equal pieces and cryo-conserved. Consecutive sections of the tumors and organs (5-10 µm) were prepared using a Leica Cryostat (Leica CM1950, Leica Microsystems GmbH, Wetzlar, Germany) from the ventral margin of each piece for a distance of 250 µm. After fixation in formalin (10%) and counterstaining with Hoechst 33342, to visualize the nuclei, the sections were mounted with an antifade solution (Vectashield mounting media H-1000, Vector Laboratories). Sections were analyzed on an upright epifluorescence microscope (Zeiss Axio Imager.Z1, Carl Zeiss MicroImaging GmbH, Jena, Germany) equipped with a C-Apochromat 40×/1.2 W Korr UV-VIS-IR objective and an AxioCam MRm camera. The visualization of the distribution of the fluorescence signals was performed using the AxioVision software (AxioVS40 V 4.8.1.9, Zeiss, Jena, Germany). Nuclei were visualized in blue (DAPI) and Hsp70 was visualized either in green (FITC) or in red (Cy5.5).

Immunohistochemistry

After weighing, the tumor was cut into 4 mm thick pieces, fixed in Bouin's solution containing 71.5% (v/v) picric acid, 23.8% (w/v) formaldehyde, 4.7% (v/v) acetic acid and embedded in paraffin. Consecutive section-pairs of the tumors (5 μm) were prepared from the ventral margin of each piece for a distance of 250 μm. The morphology of the excised tumors was visualized using standard hematoxylin-eosin (H&E) and Masson-Goldner staining. Nuclei were co-stained in 1% (w/v) Mayer's hematoxylin (Dako, Hamburg, Germany). For the immunohistochemistry, endogenous peroxidase activity was blocked using freshly prepared 1% (v/v) hydrogen peroxide containing 0.1% (w/v) sodium azide. For the detection of effector cells, sections were heated for 30 min at 97° C. and then incubated with anti-NK cell (clone DX5, 1:25, rat-anti-mouse CD49b, IgM; Biozol, Eching, Germany; clone 12F11, 1:100, rat-anti-mouse CD56, BD Biosciences, Heidelberg, Germany), anti-T cell (clone 145-2C11, 1:50, hamster-anti-mouse CD3ε, IgG; Biolegend, San Diego, USA; clone SP7, 1:100, rabbit-anti-goat CD3; Abcam, Cambridge, UK), anti-macrophage (clone BM8, 1:50, rat-anti-mouse F4/80, IgG2a, ACRIS Antibodies GmbH, Herford, Germany, 1:50), anti-granulocyte/macrophage (clone RB6-8C5, 1:50, rat-anti-mouse Gr-1 Ly6C/Ly6G, IgG2bκ; Biolegend) mAb or the appropriate isotype-matched control antibody overnight at 4° C. After washing, sections were incubated for 2 h at room temperature with a rabbit anti-rat or rabbit anti-hamster HRP-conjugated secondary polyclonal antibody preparations as appropriate (Dako, Hamburg, Germany) followed, after washing, by diaminobenzidine (Dako) as the chromogen. Sections were counter-stained with 1% (w/v) Mayer's hematoxylin (Dako) for 30 seconds and analyzed on an Axiovert 25 microscope (Zeiss, Jena, Germany)

Flat-panel Volume CT (VCT)

Figure 4A:
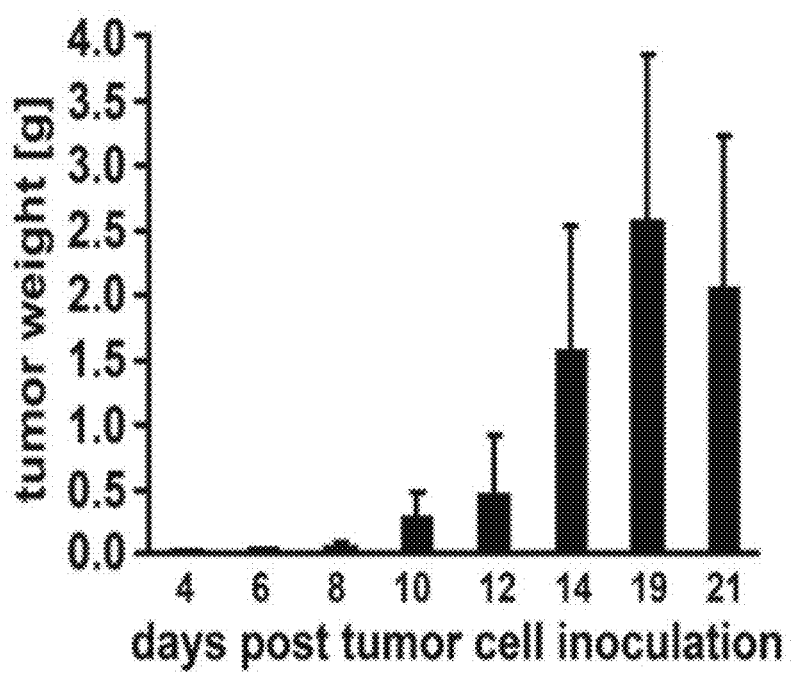
FIG. 4: A. Tumor growth curve for CT26 colon adenocarcinoma cells in BALB/c mice. Following i.p. injection of tumor cells ($2.5\times10^4$) mice were sacrificed on days 4 (0.03±0.11 g; n=3), 6 (0.05±0.2 g; n=3), 8 (0.05±0.03 g; n=5), 10 (0.29±0.2 g; n=7), 12 (0.47±0.44 g; n=7), 14 (1.55±0.9 g; n=35), 19 (2.6±1.3 g; n=17), 21 (2.05±1.18 g; n=10) and tumor weights are determined B-D: Reduction in tumor weight and the delay of CT26 tumor growth in BALB/c mice after one to three injections of cmHsp70.1 mAb is associated with an infiltration of immunocompetent effector cells. (B)
Figure 4:
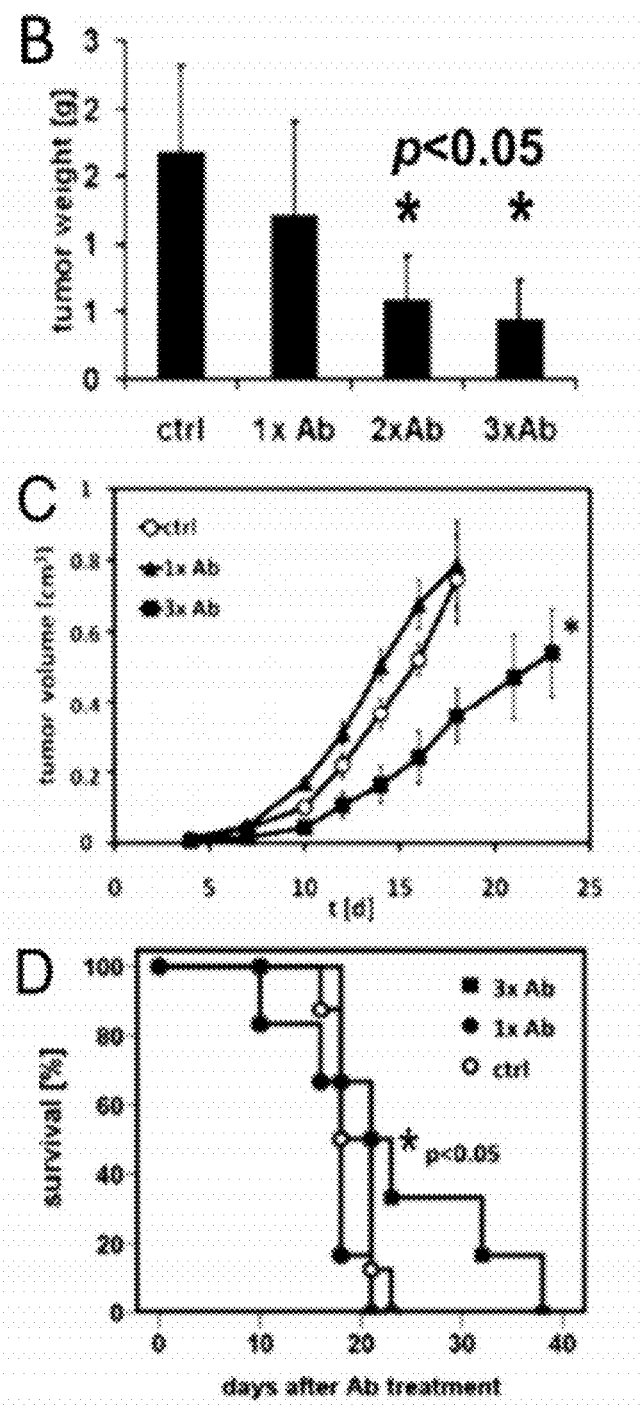

A flat-panel volume CT (VCT; FIG. 4A), a non-clinical CT prototype equipped with two flat-panel detectors (GE Global Research, Niskayuna, N.Y., USA) [21] was used for the CT analyses. Briefly, anaesthesized mice were placed on a multimodality bed throughout the imaging session and injected i.v. with 150 μl of iodine-containing contrast agent Isovist 300 approximately 30 s before starting of the scan. All data sets were acquired with a step-and-shoot technique, using 1,000 views per 1 full rotation, 8 s of rotation time per step, 360 used detector rows, 80 kVp, and 100 mA. For high resolution image reconstructions a modified Feldkamp algorithm implemented on a simultaneous computer with 8 nodes was used.

Near-infrared Fluorescence (NIRF) Imaging

The Optix system (Advanced Research Technologies, Montreal, Canada) is a 2D imaging system that works in a reflection scheme. The output of the system consists of maps of intensity and lifetime of the fluorescence distribution, in relation to a previously acquired camera image of the animal. Lifetime analysis describes the mean residence time of the fluorophor in an excited state and provides a characteristic parameter for the fluorescent probe. The mean transit time of an emitted photon following an excitation pulse can be used to calculate the depth and concentration of the fluorescence intensity by time-resolved measurements [18]. The fluorescence intensity was determined in anaesthesized, viable mice that developed s.c. tumors before (0 h), as well as 24, 48, 72 and 96 h after i.v. injection of the Cy5.5-labelled antibodies into the tail vein.

Antibody Dependent Cellular Cytotoxicity (ADCC) Assay

ADCC was measured using a standard 4 h $^{51}$Cr-release assay (33). Briefly, viable CT26 mouse colon and 1048 mouse pancreatic carcinoma cells were labelled with 0.1 μCi of Na$^{51}$CrO$_4$ at 37° C. for 1 h. After two washes with RPMI 1640 medium, $^{51}$Cr-labelled target cells ($1 \times 10^4$) were transferred into triplicate wells of a 96-well plate and the cmHsp70.1 (IgG1) mAb was added either 50 μg/L and the IgG1 isotype-matched control or (0.7, 1, 1.4 μg/ml). Freshly isolated mouse (BALB/c) spleen cells were added at various effector to target cell ratios (E:T). After a 4 h co-incubation period supernatants (100 μl) were harvested and the levels of radioactive $^{51}$Cr was counted using a gamma counter (Coulter-Counter). Percentage of ADCC-dependent cytotoxicity was calculated using the formula: % specific lysis=(experimental release−spontaneous release)/(maximum release−spontaneous release)×100. The spontaneous release in each target cell ranged between 10 and 15%.

Stimulation of Mouse Spleen Cells for ADCC

Freshly isolated BALB/c mouse spleen cells ($5 \times 10^6$ cells/mL) were cultured in RPMI 1640 medium containing 10% (v/v) FCS alone (unstimulated) or were incubated in supplemented RPMI medium containing low-dose IL-2 (100 IU/mL) plus TKD peptide (TKD, 2 μg/mL) (Bachem, Bubendorf, Switzerland) at 37° C. for 4 days. TKD is a GMP-grade 14-mer peptide of the C-terminal substrate-binding domain of human Hsp70 (TKDNNLLGRFELSG (SEQ ID NO: 2), aa 450-463) which is known to selectively induce the reactivity of human NK cells against membrane Hsp70 positive tumor cells (12). The TKD equivalent region in the mouse (TRDNNLLGRFELSG) (SEQ ID NO: 2) reflects only one conservative amino acid exchange at position 2 (K-R) and this sequence has been found to stimulate mouse NK cells, even in the absence of IL-2 (14).

Immunization

Immunizing mice and epitope specificity of cmHsp70.1 mAb. BALB/c mice were repeatedly injected (i.p. and i.v.) with increasing doses of the 14-mer TKD peptide (50, 100, 200 μg) in the presence of complete and incomplete Freund's adjuvants. Mice are sacrificed on day 120 after immunization and spleen cells were fused with the mouse myeloma cell line SP2/0. After subcloning of immunoglobulin-producing hybridoma cells, the specificity of Hsp70 reactive antibodies, as determined by ELISA technique (R&D systems), is tested against viable CX+ and CX− tumor cell lines with differential Hsp70 membrane expression pattern by flow cytometry.

Statistics

Comparative analysis of the in vitro data was undertaken using the t-test for the analysis of two paired and unpaired samples. A significance level of α=0.05 was used.

Comparative analysis of the in vitro data was undertaken using a non-parametric log rank test (Mann-Whitney). Survival times were estimated from Kaplan-Meyer curves by log-rank test (34).

Example 1

Providing Hybridomas Expressing cmHsp70.1 and cmHsp70.2

Mice were immunized with peptide TKDNNLLGRFELSG (SEQ ID NO: 2) and boosted according to an improved protocol by the inventors. After establishing several cell-lines producing antibodies that could be determined to recognize Hsp70, two hybridomas could be identified that produce antibodies capable of binding an epitope of Hsp70 that is localized extracellularly on tumor cells. In particular, cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, and cmHsp70.2 as produced by hybridoma cmHsp70.2, deposited with the DSMZ—Deutsche Sammlung von Mikroorganismen und Zellkulturen GmbH on Nov. 14, 2003, and assigned Accession Number DSM ACC2630 are provided.

The anti-Hsp70 antibody produced by hybridoma cmHsp70.1 was determined to be an IgG-type immunoglobulin while the anti-Hsp70 antibody produced by hybridoma cmHsp70.2 is an IgM-type immunoglobulin.

Example 2

Purification of Antibodies cmHsp70.1 and cmHsp70.2 by Thiophilic Chromatography

Since previous protocols for purification of immunoglobulins turned out to be cumbersome for the purification of anti-Hsp70 antibodies, a novel purification protocol has been established, comprising hydrophobic interaction chromatography (HIC) and the following materials and methods.

Material

Column material: T-Gel™ Adsorbent (Pierce, Product number: 20500)
Volume: 10 ml
Binding capacity: 20 mg immunoglobulins/ml gel
Wet bead diameter: 45-165 µm (6% beaded agarose)
Äkta Prime FPLC system (Amersham Biosciences)

Supernatants were derived from approx. 1000 ml Hybridoma supernatant from clone cmHsp70.1 or cmHsp70.2, cultured in RPMI1640/10% FCS or DEMEM/20% FCS, respectively. Supernatants from 48 h incubations at a starting cell density of $0.2 \times 10^6$ cells/ml were harvested and centrifuged at 300×g (5 min, 4° C.) following a 1000×g centrifugation (5 min, 4° C.). The supernatants were stored at 4° C.

Chemicals were obtained by Sigma ($Na_3PO_4$;$NaN_3$) or Roth (($NH_4$)$_2SO_4$;Tris), all buffer were made with millipore water.

Buffers

Binding buffer: 0.5 M ammonium sulfate, 50 mM sodium phosphate and 0.05% sodium azide, pH 8.0
  16.5 g $(NH_4)_2SO_4$
  1.78 g $Na_3PO_4$
  125 mg $NaN_3$
  pH 8.0, ad 250 ml
Elution buffer: 50 mM sodium phosphate and 0.05% sodium azide, pH 8.0
  1.78 g $Na_3PO_4$
  125 mg $NaN_3$
  pH 8.0, ad 250 ml
Storage buffer: 0.5 M Tris and 0.02% sodium azide, pH 7.4
  15.1 g Tris
  50 mg $NaN_3$
  pH 7.4, ad 250 ml Sample Preparation While mixing, 66 mg of ammonium sulfate were added per ml of clarified hybridoma supernatant; see supra. The final concentration was 0.5 M ammonium sulfate in the sample. The hybridoma supernatant was gently mixed to avoid denaturation of immunoglobulins by local high salt concentration or air. When the ammonium sulfate is fully dissolved, the sample was adjusted to pH 8.0 and centrifuged at 1000×g. The supernatant was carefully removed and passed through a 0.8 µm cell culture filter (Nalgene, Product number: 126-0020).

Equilibration of the Column

The Äkta Prime FPLC system was used in a cold room facility (6° C.). The tubing system was connected with the buffer flasks and hybridoma supernatant. The tubings were extensively rinsed with the respective buffers (50 ml minimum, at a flow rate of 50 ml/min) using the automatic washing protocols of the Äkta Prime FPLC system. The tubings were connected with the T-Gel-column, while avoiding air bubbles to get into the column. The T-gel was washed with binding buffer (minimum 50 ml) at a flow rate of 1 ml/min. The absorbance was recorded at 280 nm and the conductivity during the washing step. The column was ready to use when the absorbance reached a minimum plateau for more than 10 min and the conductivity was at approx. 140 mSi/cm.

Application of the Sample

It was changed from binding buffer to hybridoma supernatant with the buffer valve at the Äkta Prime FPLC system. The sample was applied to the column at a flow rate of 0.5 ml/min, and the flow through collected. The absorbance raised to approx. 0.2 to 0.6, indicating the absorbance of non bound proteins. In contrast, the conductivity should not change during sample application. The supernatant passed the column over night. Then it was changed from hybridoma supernatant to binding buffer with the buffer valve at the Äkta Prime FPLC system. The column was washed with binding buffer (minimum 50 ml) at a flow rate of 0.5 ml/min. The column was washed when the absorbance reached a minimum plateau for more than 10 min and the conductivity was at approx. 140 mSi/cm.

Elution of the Bound Immunoglobulins

It was changed from binding buffer to elution buffer with the buffer valve at the Äkta Prime FPLC system. The autosampler was started and fractions of 4 ml collected. The bound proteins were eluted with a flow rate of 0.5 ml/min. The absorbance and the conductivity was recorded, the latter falling to approx. 12 mSi/cm. Concomitantly the absorbance gave a peak, indicating the passing of eluted immunoglobulins. It was washed with elution buffer until the absorbance reached a minimum for more than 10 min.

Storage of the T-Gel Column

It was changed from elution buffer to storage buffer with the buffer valve at the Äkta Prime FPLC system. The column was washed with minimum 50 ml at a flow rate of 2 ml/min. The column was disconnected, sealed and stored in the cold room facility.

Every fraction of the eluted proteins was tested for the presence of immunoglobulins with an immunoglobulin-specific ELISA Immunoglobulin-containing fractions were pooled and concentrated/dialyzed against PBS by centriprep YM-30 centrifugation/filtration units (amicon, Product number: 4306) at 1000×g, 4° C. Concentration of protein was determined by conventional Bradford assay.

Specificity of the purified cmHsp70.1 or cmHsp70.2 antibodies was assessed by:

A) FACS analysis using Hsp70 membrane-positive (Colo+, CX+) or -negative (Colo−/CX−) cells.

B) Western blotting using 10 µg of whole cell lysate (K562) separated by 10% SDS-PAGE C) Blocking of NK-mediated killing of Hsp70 membrane-positive tumor target cells (Colo+, CX+); and/or D) Immunohistochemistry with Hsp70 membrane-positive tumor cells; see also example 3.

For further details of one or more of the respective steps of the purification method of the present invention see, e.g., Belew et al., J. Immunol. Meth. 102 (1987), 173-182 and Nopper et al., Anal. Biochem. 180 (1989), 66-71, which refer to previous methods for the purification of monoclonal antibodies using salt-promoted adsorption and chromatography on a thiophilic adsorbent and thiophilic adsorbent for the one-step high-performance liquid chromatography, respectively.

Example 3

Characterization of Binding Properties and Biological Activity of Antibodies cm Hsp70.1 and cmHsp70.2

Antibodies cmHsp70.1 and cmHsp70.2 have been found to inhibit the cytolytic activity of cells against Hsp70 expressing tumor cells using methods described in Multhoff et al., Int. J. Cancer 61 (1995b), 272 and WO02/22656; see also FIG. 1. Due to the fact that cmHsp70.1 and cmHsp70.2 exhibit an inhibitory effect on the cytolytic activity of NK cells against Hsp70 expressing tumor cells it was of interest to map their binding epitopes. By peptide scanning (pepscan) of the C-terminal substrate binding domain within aa 384-618 the 8-mer peptide NLLGRFEL (SEQ ID NO: 1) (aa 454-461) could be determined as the relevant recognition structure for the cmHsp70.1 antibody. This antibody reacts specific with Hsp70 but does not substantially cross-react with Hsc70 as determined with standard assays. The only amino acid difference of Hsp70 and Hsc70 within the 8-mer antibody binding epitope (aa 454-460) is the exchange at position 458 from arginine (R) to lysine (K). Similarly, antibody cmHsp70.2 was determined to specifically recognize a peptide consisting of the amino and sequence TKDNNLLGRFELSG (SEQ ID NO: 2).

The provision of the above described and deposited hybridomas provide a reliable source of anti-Hsp70 antibodies capable of detecting extracellular epitopes of Hsp70 on viable cells, preferably tumor cells and thereby enabling the specific detection and treatment of cells which display Hsp70 on their cell surface, in particular tumor cells and cells infected by pathogens, see also Table 1 and 2 supra. Thus, the present invention provides a novel class of anti-Hsp70 antibodies for use in therapy and diagnosis as well as in research in general.

Example 4

Binding of mAb cmHsp70.1 mAb to Cell Surface-bound Hsp70 on Mouse Tumor Cell Lines In Vitro Antibodies cmHsp70.1 and cmHsp70.2 have been found to inhibit the cytolytic activity of cells against Hsp70 expressing tumor cells using methods described in Multhoff et al., Int. J. Cancer 61 (1995b), 272 and WO02/22656; see also FIG. 1. Due to the fact that cmHsp70.1 and cmHsp70.2 exhibit an inhibitory effect on the cytolytic activity of NK cells against Hsp70 expressing tumor cells it is of interest to map their binding epitopes. By peptide scanning (pepscan) of the C-terminal substrate binding domain within aa 384-618 the 8-mer peptide NLLGRFEL (SEQ ID NO: 1) (aa 454-461) could be determined as the relevant recognition structure for the cmHsp70.1 antibody. This antibody reacts specific with Hsp70 but does not substantially cross-react with Hsc70 as determined with standard assays. The only amino acid difference of Hsp70 and Hsc70 within the 8-mer antibody binding epitope (aa 454-460) is the exchange at position 458 from arginine (R) to lysine (K). Similarly, antibody cmHsp70.2 was determined to specifically recognize a peptide consisting of the amino and sequence TKDNNLLGRFELSG (SEQ ID NO: 2).

Characterization of Binding Properties and Biological Activity of Antibodies cm Hsp70.1 and cmHsp70.2

Screening of different mouse tumor cell lines with the IgG1 anti-human Hsp70 specific monoclonal antibody (mAb) cmHsp70.1, which detects the cell surface localized form of Hsp70 on human tumors, reveal that this antibody also recognizes membrane Hsp70 on mouse tumor cell lines [22]. An Hsp70 membrane-positive phenotype is determined in mouse colon carcinoma (CT26), plasmocytoma (ADJ), malignant melanoma (B16/F10) and MOS162 osteosarcoma cells (C3H) derived from different mouse strains (Table 1). In contrast, the mouse pancreatic carcinoma (1048) and the A20 B cell lymphoma cell line are considered as being membrane Hsp70 negative (Table 1).

A detailed macro- and microscopical inspection of tumor-free organs of the mice reveal that the cmHsp70.1 mAb does not bind to any normal mouse tissues. A non-specific up-take of antibody-free fluorescence dye into the tumor is unlikely since different cmHsp70.1-fluorophor conjugates produced identical results.

TABLE 1

Proportion of Hsp70 membrane positive cells in different malignant mouse tumor cell lines.

| Mouse tumor cells (mouse strain) | Origin | Hsp70 membrane-positive cells (%) |
|---|---|---|
| CT26 (BALB/c) | Colon | 44 ± 5.2 |
| 1048 (BALB/c) | Pancreas | 12 ± 10.3 |
| A20 (BALB/c) | B cell | 5 ± 4.3 |
| ADJ (BALB/c) | Plasmocytoma | 45 ± 5.4 |
| B16/F10 (C57/Bl6) | Melanoma | 97 ± 6.2 |
| MOS162 (C3H) | Osteosarcoma | 70 ± 3.6 |

Hsp70 membrane positivity on mouse tumor cell lines is determined by flow cytometry using the cmHsp70.1-FITC mAb at 4° C. In line with previous reports [8, 12, 27] a sample is considered as Hsp70 membrane-positive when more than 15% of the cells are positively stained with the cmHsp70.1-FITC mAb. The data represent the mean of at least 6 independent experiments±S.E.

Similar to the tumor cell lines, single cell suspensions of primary human gastrointestinal and pancreatic tumor samples (n=229) can also be stained with cmHsp70.1 mAb. A membrane Hsp70 positive phenotype with the cmHsp70.1 mAb can be determined in more than 40% of the cases. In contrast, the corresponding reference tissues derived from the same patients are always membrane Hsp70 negative as indicated in Table 2.

TABLE 2

Membrane Hsp70 positive cases in human gastrointestinal and pancreatic carcinomas.
Human samples

| Tumor entity | Membrane Hsp70 positive cases/ total number | Proportion of membrane Hsp70 positive cases (%) |
|---|---|---|
| stomach | 13/32 | 41% |
| colon | 20/45 | 45% |
| caecum | 5/9 | 56% |
| sigmoid | 19/40 | 48% |
| rectum | 35/86 | 41% |
| pancreas | 11/17 | 65% |
| total GIST | 103/229 | 45% |
| corresponding normal tissues | 0/52 | 0% |

The Hsp70 phenotype on freshly prepared samples derived from different anatomic sites of the gastrointestinal tract is determined by flow cytometry using the cmHsp70.1-FITC mAb. A sample is considered as being membrane Hsp70 positive if more than 20% of the viable cells are positively stained with the cmHsp70.1-FITC mAb. None of the corresponding normal tissues that are tested expressed membrane Hsp70. The cmHsp70.1 mAb binds to membrane Hsp70 positive human and mouse tumors. Viable human tumor cell lines such as colon (CX2) and breast (MDA436, MCF-7) carcinomas can be stained with cmHsp70.1 mAb.

Figure 2:
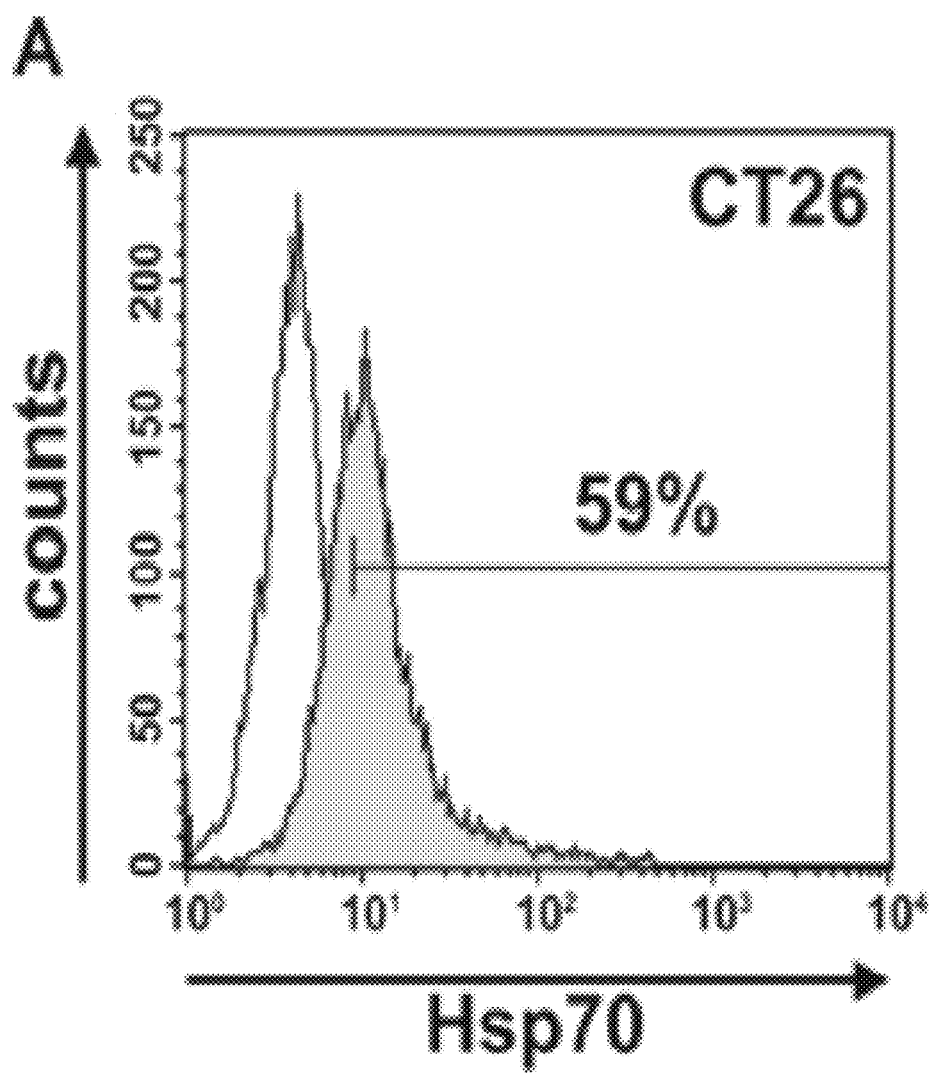
FIG. 2: (A) Flow cytometric analysis. Representative view of the Hsp70 cell surface expression on CT26 mouse colon carcinoma cells after flow cytometric analysis using the cmHsp70.1-FITC conjugated mAb. Results are expressed as log green fluorescence intensity vs relative cell numbers. The IgG1 isotype-matched control is indicated in white and membrane Hsp70 positive population is shown in grey. Only viable (propidium-iodide negative) cells were gated and analyzed. (B) Representative immunofluorescence images of CT26 tumor cells stained with cmHsp70.1-FITC mAb at 4° C. (cell surface staining; left), or following a temperature shift to 37° C. for 15 min (cytosolic staining; right). The scale bar represents 20 µm. (C) Representative views of the kinetics of cmHsp70.1-FITC mAb uptake into CT26 tumor cells. Tumor cells were washed and analyzed by flow cytometry following incubation with cmHsp70.1-FITC mAb or IgG1-FITC for 2, 5, 10, 15, 30 and 60 min cells at 4° C. (left panel) and 37° C. (right panel). The upper graphs indicate the percentage of positively stained cells the lower graphs indicate the antigen densities at the indicated time points, expressed as the mean fluorescence intensity (mfi). The increase in the proportion of membrane Hsp70 positive cells and in the mfi was significant ($p<0.05$) at 37° C. but not at 4° C. (D) Representative immunofluorescence images of CT26 tumor cells either stained with cmHsp70.1-FITC (green, first row) or with Cy3-secondary antibody labelled (red, second row) Rab4 (early endosome), Rab5a (early endosome), Rab7 (late endosome), Rab9 (late endosome), Rab11 (trans golgi network, recycling endosome), LAMP1 (CD107, lysosome), LAMP2 (lysosome) antibodies at 4° C. (left three rows) and after an incubation of 30 min at 37° C. (right three rows). A co-localization of the FITC (green) and Cy3 (red) fluorescence, as indicated in a yellow spectrum (third row), is marked with + in the merged fluorescence staining pattern. Isotype-matched control antibodies did not show any staining (data not shown). Similar results were obtained in 3 independent experiments. The scale bar represents 20 µm.
Figure 2:
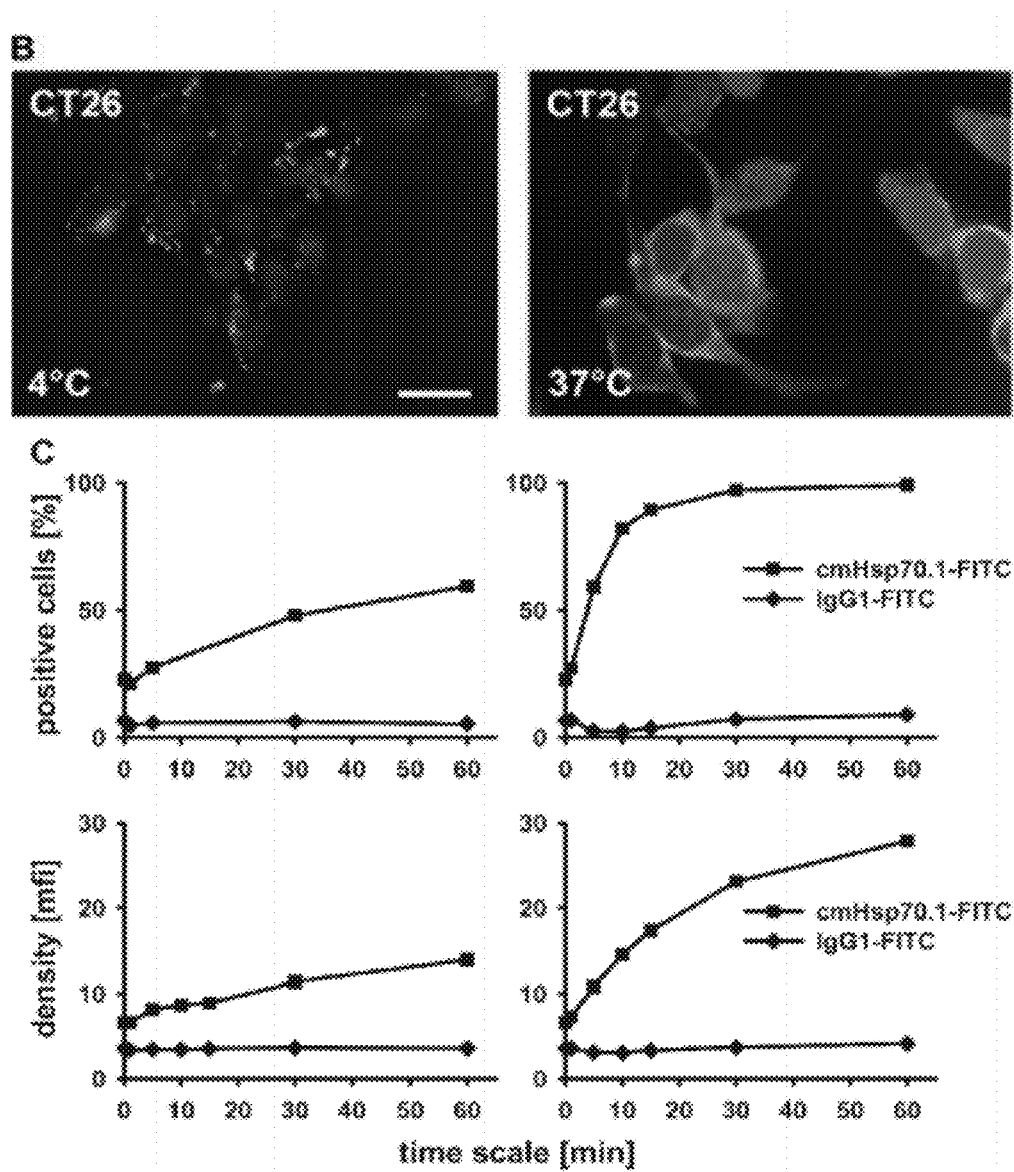
Figure 2:
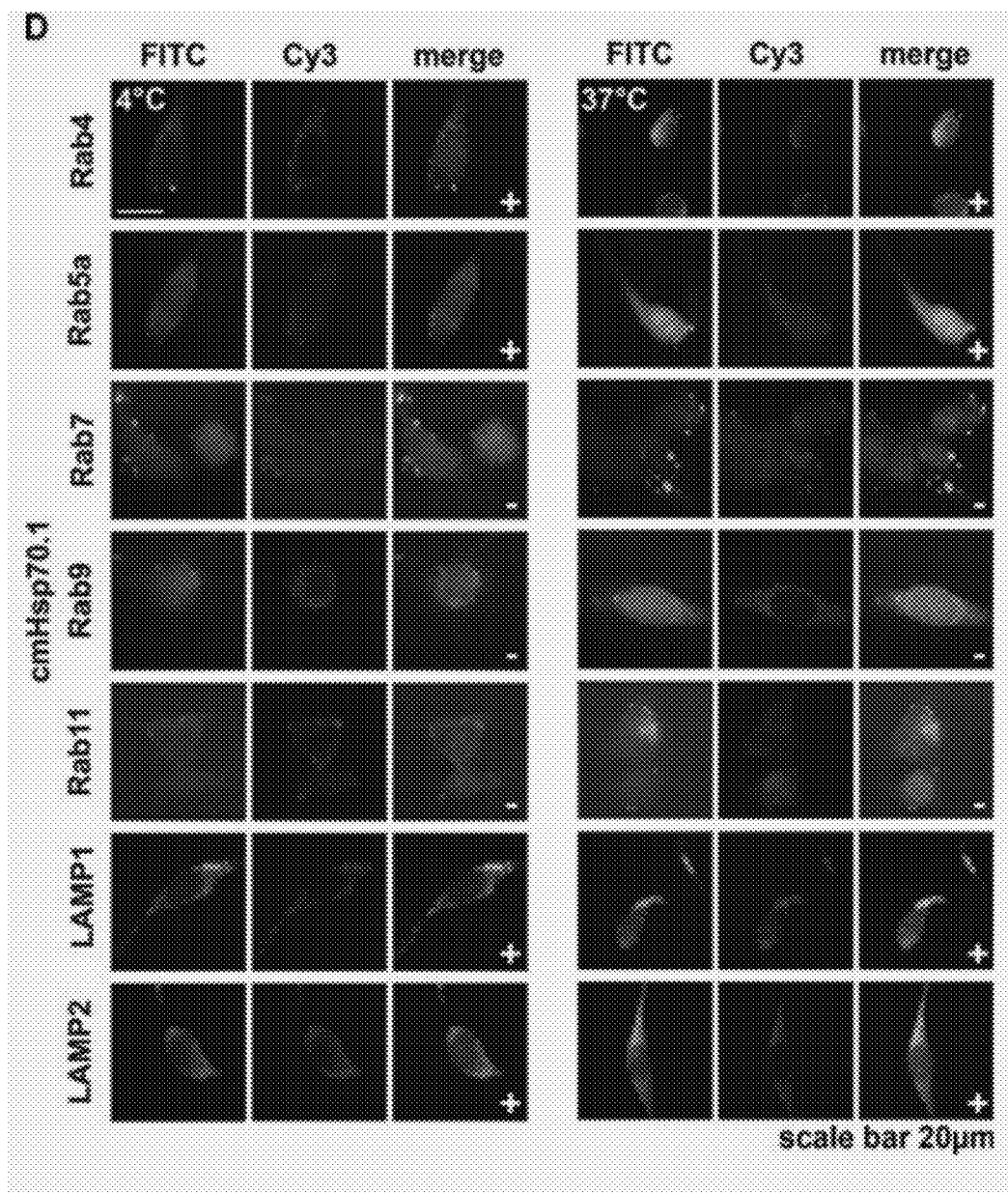

A representative flow cytometric image of the mouse CT26 colon carcinoma cell line is illustrated in FIG. 2A. Cytosolic Hsp70 staining is excluded, as the entire staining procedure is performed at 4° C., and only 7-AAD-negative, viable tumor cells with intact plasma cell membranes are analyzed. FIG. 1B illustrates the different binding patterns of the cmHsp70.1-FITC mAb to CT26 tumor cells at 4° C. (left panel) and at 37° C. (right panel). At 4° C., the binding of cmHsp70.1-FITC mAb to CT26 tumor cells reveals a typical ring-shaped cell surface staining pattern (FIG. 2B, left panel). The dotted staining pattern reflects the localization of membrane-bound Hsp70 in lipid rafts [23,24]. Measurements, using fluorescence-conjugated marker beads reveal that approximately 10,000 Hsp70 molecules are present on the plasma membrane of the mouse tumor cell line CT26 at 4° C. (data not shown).

A shift to 37° C. resulted in a strong intracellular staining pattern, which likely results from the translocation of the FITC-conjugated antibody cmHsp70.1-FITC into the cytosol (FIG. 2B, right panel). Kinetic studies show a significant increase in the proportion of Hsp70 membrane-positive cells at 37° C. between 2 and 15 min after incubation with cmHsp70.1-FITC mAb, but not with an isotype-matched control antibody (FIG. 2C, upper right panel). In contrast, at 4° C. the proportion of Hsp70 membrane-positive tumor cells remained nearly unchanged up to 60 min (FIG. 2C, upper left panel). Furthermore, the mean fluorescence intensity (mfi) of Hsp70 per cell significantly increase after incubation with antibody at 37° C. from 2 to 60 min (FIG. 2C, lower right panel), but remain stably low at 4° C. (FIG. 2C, lower left panel). These data indicate that the cmHsp70.1-FITC staining accumulates in Hsp70 membrane-positive tumor cells at the physiological temperature of 37° C., but not at 4° C. The reason for the antibody uptake is due to a rapid turnover rate of membrane-bound Hsp70. The inventors could show that membrane Hsp70 expression is completely restored already after 15 min after its removal by enzymatic digestion (data not shown). As expected, tumor cells with an initially low Hsp70 membrane expression level, such as 1048 pancreatic carcinoma cells and A20 B cell lymphoma cells, showed little cell surface staining at 4° C., nor did they internalize the cmHsp70.1-FITC mAb at 37° C. (data not shown). In order to identify the endo-lysosomal compartment in which Hsp70 accumulates following endocytosis at 37° C. a co-staining of Hsp70 (cmHsp70.1-FITC) with Cy3 secondary antibody labelled early (Rab4; Rab5a), late (Rab7, Rab9), recycling (Rab11) endosomal and lysosomal (LAMP1, LAMP2) markers was performed. As visualized in FIG. 2D, co-localization of Hsp70 was predominantly found with Rab4, Rab5a, LAMP1 and LAMP2 at 4° C. and at 37° C. (yellow dots in the merged photographs, marked with a +). In summary, the data derived from 3 independent experiments (data not shown) indicate that Hsp70 predominantly accumulates in the early endosomal compartment and becomes degraded in lysosomes.

Example 5

Determination of cmHsp70.1 mAb Affinity Towards Human Recombinant Hsp70 Protein Via Biacore The concentration-dependent affinity of the full length cmHsp70.1 mAb to immobilized human Hsp70 is determined using a Biacore X system (FIG. 3). The sensogram profiles of FIG. 3 are globally fitted to a 1:1 binding model with the BIAevaluation software. The calculated $K_{on}$ value is $6.99 \times 10^4$ $M^{-1}s^{-1}$ and the $K_{off}$ value is $3.79 \times 10^{-4}$ $s^{-1}$ with a dissociation equilibrium constant $K_D$ of 5.4 nM for Hsp70 with a Chi$^2$ of 59.4.

Example 6

In Vivo Tumor Growth of Intraperitoneal (i.p.) and Subcutaneous (s.c.) Transplanted CT26 Cells An i.p. injection of $2.5 \times 10^4$ CT26 mouse colon adenocarcinoma cells suspended in 100 µl PBS resulted in rapidly growing tumors (FIG. 4A, black bars). The average weight of an individual tumor is 2.6 g±1.3 (n=17) on day 19 and most animals became moribund shortly thereafter due to the large tumor weight in the abdomen. Tumor take at any tested time point is always 100%. A comparative phenotyping of CT26 cells from tissue culture and from single cell suspensions derived from tumor-bearing mice on day 14 reveal that the amount of Hsp70 membrane positive cells has been found to be significantly elevated from 56.2±9% (n=6) up to 79.8±14% (n=7) in mouse-derived tumors (data not shown). Tumor growth is similar following s.c. injection of the same number of CT26 cells into the neck, although mice do not die until day 26 (data not shown). An intraperitoneal injection of $2.5 \times 10^4$ CT26 mouse colon tumor cells suspended in 100 µL PBS result in rapidly growing tumors with a tumor take of 100%. A comparative phenotyping of cultured CT26 and single-cell suspensions derived from CT26 tumor-bearing mice on day 14 revealed the proportion of membrane Hsp70$^+$ cells to be significantly greater in the latter 46.2±9%, n=6 vs. 69.8±14%, n=7; P<0.05). Based on the observation of the inventors that the cmHsp70.1 mAb initiates ADCC in membrane Hsp70$^+$ CT26 cells in vitro, the capacity of this antibody to induce tumor killing in CT26 tumor-bearing mice is evaluated. The tumor weights in mice that received two and three consecutive intravenous injections of cmHsp70.1 mAb (20 µg per injection) on days 3, 5, and 7 are significantly lower than those in mice receiving an isotype-matched control antibody (1.7±0.63 g vs. 0.59±0.32 g and 0.44±0.29 g, respectively, P<0.05) (FIG. 4B). Growth curves of CT26 tumors after subcutaneous injection of $1 \times 10^6$ cells after one and three intravenous injections of cmHsp70.1 mAb (20 µg per injection) on days 4, 7, and 10 reveal that three repeated injections of cmHsp70.1 mAb result in a significant growth delay (FIG. 4C) (P<0.05), which is correlated with an increased overall survival (FIG. 4D) (P<0.05).

Immunohistochemical studies of consecutive CT26 tumor sections following one to three injections of cmHsp70.1 mAb revealed a dramatic increase in F4/80$^+$ macrophages and Ly6G/Ly6C$^+$ granulocytes, and a moderate increase in Ly49b$^+$ CD56$^+$ NK cells within the tumor (Table 3). CD3$^+$ T cells began to infiltrate tumor tissue from day 21 onwards (Table 3).

TABLE 3

Semiquantitative analysis of the lymphocytic and granulocytic infiltration of CT26 tumors after one to three injections of the cmHsp70.1 mAb.

| Marker | Treatment with cmHsp70.1 mAb | | | |
|---|---|---|---|---|
| | Ctrl | 1× | 2× | 3× |
| CD3ε (T cells) | − | − | − | + |
| Ly49b/CD56 (NK cells) | + | + | ++ | +++ |
| F4/80 (macrophages) | ++ | ++ | ++ | +++ |

TABLE 3-continued

Semiquantitative analysis of the lymphocytic and
granulocytic infiltration of CT26 tumors after
one to three injections of the cmHsp70.1 mAb.

| Marker | Treatment with cmHsp70.1 mAb | | | |
|---|---|---|---|---|
| | Ctrl | 1× | 2× | 3× |
| Ly6G/Ly6C (Gr-1) (granulocytes/macrophages) | + | ++ | ++ | +++ |

BALB/c mice were injected (intraperitoneally) with CT26 tumor cells ($2.5 \times 10^4$) on day 0 and injected with cmHsp70.1 mAb (20 μg per injection) on days 3, 5, and 7. Mice were killed on day 21 and at least six consecutive tumor sections (5 μm) were examined immunohistochemically using antibodies directed against T cells (CD3ε), NK cells (Ly49b), monocytes (F4/80), and granulocytes (Ly6G/Ly6C). The results indicate the number of infiltrating cells within a defined tumor section of 1 cm²; −, no infiltration (<10); +, weak infiltration (10-50); ++, intermediate infiltration (50-200); +++, strong infiltration (<200).

Example 7

Intraoperative In Vivo Imaging of Hsp70 in Tumor-bearing Mice

Fluorescence-labelled cmHsp70.1-Cy5.5 mAb or IgG1-Cy5.5 (100 μg each) are injected i.v. into the tail vein of tumor-bearing mice on day 14 after i.p. injection of CT26 cells ($2.5 \times 10^4$), at which time the average tumor weight of 1.55 g±0.9 (n=35, FIG. 3). In order to obtain a more detailed overview of the binding characteristics of the cmHsp70.1 mAb in vivo, an intraoperative technique is used for in vivo imaging. The upper part of FIG. 5A illustrates true color autopsy images of the CT26 tumors in mice injected either with the IgG1 isotype-matched control or the cmHsp70.1 mAb, both of which are conjugated with Cy5.5. The regions of the tumors are marked with a white dotted line. The fluorescence images of the IgG1-Cy5.5 control antibody and that of the identically labelled mAb cmHsp70.1-Cy5.5 are indicated below in false multispectral views. As indicated on the left panel, an orange spectrum represents a region of high antibody intensity, whereas a blue and green spectrum represents low antibody staining intensities. Localization of the cmHsp70.1-Cy5.5 (FIG. 5A, lower right panel), but not the IgG1-Cy5.5 isotype-matched control antibody (FIG. 5A, lower left panel), in the tumor is detectable at relatively high amounts, as early as 30 min following i.v. injection of the antibodies in the tail vein. Kinetic studies indicated a progressive accumulation of the cmHsp70.1-Cy5.5 mAb (FIG. 5B, lower panel), but not the IgG1 isotype-matched control (FIG. 5C, lower panel), within the tumor between 2 and 8 h. In FIGS. 5B and 5C the Cy5.5 staining of both, cmHsp70.1-Cy5.5 mAb and isotype control is indicated in red and the antibody-free mouse tissues are represented in light blue color spectra. It appeared that the cmHsp70.1 mAb, but not the IgG1 isotype matched control is predominantly located within the tumor. An overall inspection of different mouse organs and the tumor revealed that apart from the CT26 tumors no other mouse tissues are positively stained for the Cy5.5-labelled mAb cmHsp70.1 (data not shown). These data are confirmed by immunofluorescence studies of sections (10 μm) of the tumors (FIG. 5D, left panel) and normal tissues (lung; FIG. 5D, right panel) of the identical animals. An endo-lysosomal Cy5.5 staining pattern, as already shown for in vitro cultured CT26 tumor cells (FIG. 2D), is detectable only in the tumor sections by using the cmHsp70.1 mAb, but not in normal tissues (FIG. 5D, lower panel). The IgG1 control antibody did neither stain tumor nor normal tissues including liver, lung and heart. The lung is shown as a representative example for the normal tissue in the upper panel of FIG. 5D. The cmHsp70.1-Cy5.5 mean intensity of cell area is 3.7 fold higher in the tumor compared to that in the lung tissue. In line with these findings are the results from immunofluorescence studies of sections (5 μm) derived from tumor-bearing mice that had received FITC-labelled cmHsp70.1 mAb or IgG1 immunoglobulin via the tail vein, the fluorescent intensities of which are identical, as determined by multicolour luminescence reader (data not shown).

Example 8 cmHsp70.1 Specifically Detect Tumor but Not Healthy Tissue

Representative images of sections of tumors (day 14 after i.p. injection of CT26 tumor cells, FIG. 6A) and normal tissues, such as the liver (FIG. 6B), lung (FIG. 6C) and kidney (FIG. 6D) of tumor-bearing mice, which had been injected either with cmHsp70.1-FITC or with IgG1-FITC, clearly demonstrate a time-dependent (from 3 to 72 h) and specific up-take of the Hsp70 specific antibody into the tumors. In contrast, the identically-labelled IgG1 isotype-matched control antibody is only found in the liver 3 h after i.v. injection. A weak staining of the liver is also detectable 3 h after i.v. injection of the cmHsp70.1 mAb, but this had completely disappeared after 24 h. Other normal tissues of the same mice, such as lung (FIG. 6C), kidney (FIG. 6D), heart (data not shown) and spleen (data not shown) do not show any fluorescence staining at the indicated time points. In summary these data show that irrespectively of the fluorescence label (Cy5.5, FIG. 5; FITC, FIG. 6; Alexa, data not shown), the cmHsp70.1 mAb binds to Hsp70 membrane-positive tumors in vivo in a highly selective manner. Due to the time-dependent concentration of the cmHsp70.1 mAb within the tumors of the mice, we hypothesize that in accordance with our in vitro findings (FIG. 2C) the Hsp70 mAb becomes rapidly internalized into the endo-lysosomal compartment also in vivo. A non-specific uptake of the fluorescence dye is unlikely since identical results are obtained using Cy5.5 (FIG. 5), FITC (FIG. 6) and Alexa (data not shown) conjugated reagents.

Example 9

Near-infrared Fluorescence (NIRF) In Vivo Imaging of Hsp70 in Tumor-bearing Mice The Optix system was used for the long-term analysis and for quantification of the fluorescence intensities in mice bearing subcutaneous tumors. Lifetime and fluorescence intensities are determined 0, 24, 48, 72 and 96 h after i.v. injection of the Cy5.5-conjugated antibodies into anaesthetized mice. The fluorescence probes are scanned by Optix in vitro in order to determine their specific fluorescent lifetimes prior to the in vivo experiments. Based on a single exponential fit to the decay of the curve, a fluorescent lifetime of 1.7 ns is calculated for the cmHsp70.1-Cy5.5 and the IgG1-Cy5.5. The dye to antibody molar ratio is 0.74 for the cmHsp70.1 mAb and 1.02 for the IgG1 control. The upper panel of FIG. 7A depicts fluorescence lifetimes of the scanned region in a tumor-bearing animal injected with cmHsp70.1-Cy5.5 mAb, and the lower graph in a tumor-bearing animal injected with IgG1-Cy5.5 at the indicated time points, as determined by NIRF imaging. Lifetime images serve as specificity controls of the Cy5.5 staining and enable specific fluorescence to be distinguished from autofluorescence. The estimated fluorescence lifetime for all scanned points in both mice is approximately 1.7 ns. This value is comparable to that of the Cy5.5 labelled antibodies measured in vitro. Flat-panel volume CT (VCT) images, which are taken 24 h after i.v. injection of the antibodies, reveal comparable volumes of both tumors. The tumor volume of the mouse which had been injected with cmHsp70.1 mAb was 0.227 cm³ and 0.211 cm³ for the IgG1 mAb-injected mouse. Furthermore, anatomical imaging by high resolution 3D flat-panel VCT imaging demonstrates the localization of the tumors (FIG. 7A, right panel) in correlation to the Cy5.5 fluorescence signals (FIG. 7B). FIG. 7B represents a follow-up of the fluorescence intensity of the Cy5.5-labelled cmHsp70.1 mAb (upper panel) and IgG1 isotype-matched control (lower panel) 0, 24, 48, 72 and 96 h after i.v. injection of the probe. The whole body fluorescence intensity scans, which are taken 72 h after i.v. injection, demonstrate a selective binding of the Cy5.5 labelled cmHsp70.1 mAb to the tumor tissues (FIG. 7B, right panel). A quantitative analysis of the average fluorescence intensities in these two mice at the indicated time-points is summarized in FIG. 7C. It appears that the average intensity of the cmHsp70.1 mAb is always stronger than that of the isotype-matched control at all time-points, with a maximum at 24 h. A summary of the average fluorescence intensities for both groups of treated animals (derived from 5 animals per time-point) confirm these results and reveal significantly stronger fluorescence signals over the tumors of mice that receive the cmHsp70.1 mAb in comparison to IgG1 isotype-matched control antibody at the time points 24 (54.33±3.9 vs 16.92±4.9; p<0.001), 72 (32.97±4.7 vs 24.17±3.0; p<0.05) and 96 h (30.29±9.1 vs 12.01±1.9; p<0.05) after i.v. injection (FIG. 7D).

Example 10

Effects of cmHsp70.1 mAb on CT26 Tumor Cells In Vitro

Although it is known that IgG1 mouse monoclonal antibodies in general have a low capacity to mediate antibody dependent cellular cytotoxicity (ADCC), the cmHsp70.1 mAb is tested against Hsp70 membrane-positive CT26 tumor cells. As summarized in FIG. 8, the cmHsp70.1 induces ADCC in CT26 at the very low concentration of 1.4 µg/ml. In contrast, lower concentrations does not affect the viability of CT26 tumor cells.

Example 11

Monoclonal Antibody cmHsp70.1 Initiates ADCC in Membrane Hsp70⁺ Tumors In Vitro

Measurements using fluorescence-conjugated marker beads revealed that ≈10,000 Hsp70 molecules are present on the plasma membrane of CT26 mouse tumor cells as mentioned above. Despite this relatively low surface density, 50 µg/mL cmHsp70.1 mAb could induce significant ADCC-mediated killing of CT26 carcinoma cells by unstimulated mouse spleen effector cells at E:T ratios ranging from 50:1 to 6.25:1 (FIG. 9A) (P<0.05). The 1048 carcinoma cells that contained only a small proportion of Hsp70⁺ cells were not sensitive to ADCC (FIG. 9A). As a control, the capacity of other mouse IgG1 antibodies (SPA810, O×7.11) and the cmHsp70.1 Fab fragment to induce ADCC is assessed and compared with that of cmHsp70.1 mAb. As shown in FIG. 9B, neither SPA810 mAb nor cmHsp70.1 Fab induced any significant ADCC against membrane Hsp70⁺ CT26 tumor cells. Similar negative findings are obtained if mouse BW cells (hybrid cross between New Zealand Black and White mice) are transfected with theta (56% membrane theta⁺ cells) are used as target cells for ADCC (FIG. 9C). In the same experiment, cmHsp70.1 mAb induces significant ADCC in CT26 colon adenocarcinoma cells 60% membrane Hsp70⁺ cells) (FIG. 9C). To determine whether preactivating mouse spleen cells with TKD (2 µg/mL) plus IL-2 (100 IU/mL) improves the killing of membrane Hsp70⁺ CT26 cells in vitro, ADCC experiments are repeated using unstimulated and preactivated effector cells. The stimulation of mouse spleen cells with TKD/IL-2 significantly increased T.N.R. the proportion of CD49b⁺ NK cells and CD25⁺ cells (Table 4) (P<0.05) and the lysis of CT26 cells (FIG. 9D) (P<0.01). An element of this increase in cytolysis could be explained by a direct killing of membrane Hsp70+ tumor cells by TKD/IL-2-activated NK cells (12), as it is apparent in the absence of the cmHsp70.1 mAb (FIG. 9D). However, the presence of cmHsp70.1 mAb further enhances the cytolytic activity of unstimulated and TKD/IL-2-stimulated mouse spleen cells against membrane Hsp70⁺ CT26 cells.

TABLE 4

Proportion (%) of marker positive cells in unstimulated and TKD/IL-2 pre-activated mouse spleen cells;

| | Proportion of antigen positive cells (%) | |
|---|---|---|
| Antigen | Unstimulated | TKD/IL-2 stimulated |
| CD8 (T cells) | 11.2 ± 1.3 | 13.8 ± 3.4 |
| CD4 (T cells) | 21.1 ± 0.9 | 15.4 ± 5.9 |
| CD205 (granulocytes) | 6.4 ± 3.3 | 12.0 ± 5.4 |
| CD11c (APC) | 6.4 ± 3.2 | 8.4 ± 5.5 |
| Ly6G/Ly6C (Gr-1) | 8.7 ± 4.7 | 7.5 ± 3.0 |
| B220 (B cells) | 62.9 ± 5.4 | 61.0 ± 5.3 |
| CD11b (APC) | 14.6 ± 2.9 | 18.2 ± 4.9 |
| CD49b, CD56 (NK cells) | 12.8 ± 4.7 | 22.5 ± 4.0* |
| CD25 (activation marker) | 6.9 ± 4.7 | 9.7 ± 7.1* |

*p < 0.05, corrected for multiple testing.

Example 12

Repeated Injections of cmHsp70.1 mAb Result in a Significant Growth Delay and Increased Overall Survival of the Treated Mice In line with the above-mentioned findings, overall survival was also greater in mice with intraperitoneal CT26 tumors (FIG. 10A, filled squares) (n=24, P<0.0001) than their IgG1 isotype-matched control antibody treated counterparts (FIG. 10A, open circles) (n=14). In contrast, an identical treatment regimen has no significant effect (P=0.310) on the survival of mice bearing A20 B-cell lymphomas, which lack membrane Hsp70 expression (FIG. 10B). Furthermore, the decrease in tumor weight after three intravenous injections of cmHsp70.1 mAb was associated with a significant increase in serum levels of Hsp70 on day 14 (154±41.7 pg/mL vs. 1,434.5±786 pg/mL, n=4, P<0.01), as measured by ELISA.

Example 13

TKD Peptide is the Target for ADCC

Figure 11B:
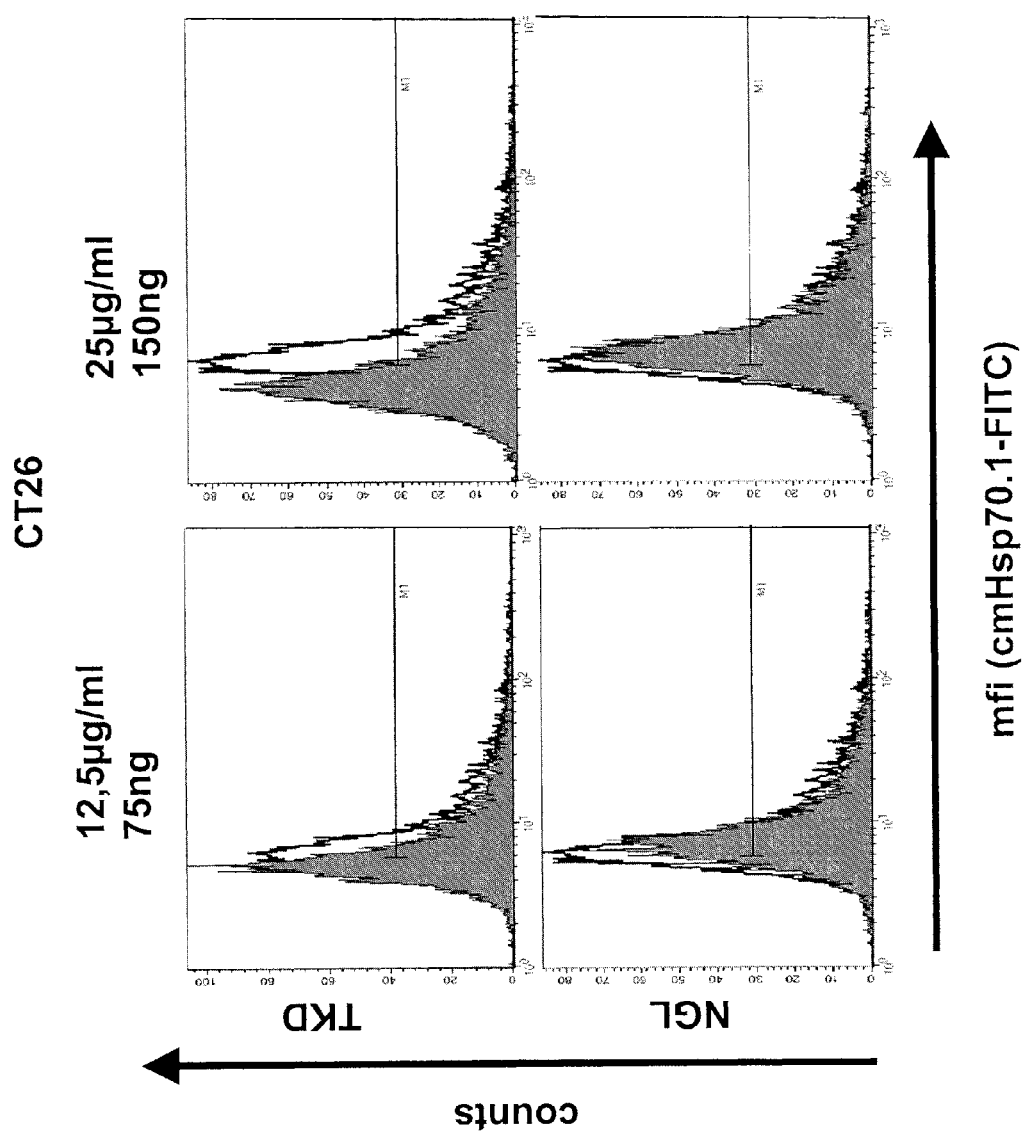

Co-injection of cmHsp70.1 mAb (20 µg per injection) with an excess of Hsp70 peptide TKD (50 µg per injection) into CT26 tumor-bearing mice (intraperitoneally) on days 3, 5, and 7 completely reversed the antitumoral effect of the antibody therapy (P<0.02) (FIG. 11A). This finding indicated that the TKD peptide, which contains the epitope of the cmHsp70.1 mAb, competes with membrane Hsp70 on the cell surface of mouse tumors for binding in vivo. The specificity of the interactions is further confirmed by determining whether the binding of cmHsp70.1 mAb to the cell surface of cultured CT26 tumor cells can be blocked by the TKD peptide, which represents the immunogen, but not by a 14-mer scrambled NGL (NGLTLKNDFSRLEG) (SEQ ID NO: 3) peptide consisting of the same amino acid residues in a different order. The proportion of membrane Hsp70$^+$ cells decrease in a concentration-dependent manner from 59% (white graph) to 44% (gray graph; 12.5 µg/mL) and from 60% (white graph) to less than 15% (gray graph; 25 µg/mL) (FIG. 11B). In contrast, no inhibition in binding is apparent when the same concentrations of NGL peptide are used for the blocking experiments (FIG. 11B, right). As a control, the binding of cmHsp70.1 mAb to CT26 cells is also significantly inhibited using the C-terminal substrate binding domain of Hsp70 (P<0.05) (FIG. 11C). All blocking studies are performed at 4° C. because of the rapid internalization of cmHsp70.1 mAb at higher temperatures.

Discussion

Tumors, but not the corresponding normal tissues, frequently present Hsp70 on their cell surface. Moreover, an Hsp70 membrane-positive phenotype was found to predict a decreased overall survival in tumor patients with an extrahepatic route of metastasis [10], and thus might act as a negative prognostic marker. In contrast, patients whose tumors metastasize into the liver have shown a better clinical outcome due to the presence of hepatic NK cells that may provide an immunological filter for membrane Hsp70 tumor cells [10]. These data indicate the medical need for the development of novel strategies to visualize and target highly aggressive, Hsp70 membrane-positive tumors.

Herein, the role of membrane Hsp70 as a potential tumor-specific target for in vivo imaging was evaluated. Our laboratory generated an IgG1 mouse anti-human Hsp70 specific mAb termed cmHsp70.1 which specifically detects the membrane-bound form of Hsp70 on viable human tumor cells with an intact plasma membrane [5,6]. Human and mouse Hsp70 does not differ within the 8-mer region in the C-terminus, which is recognized by mAb cmHsp70.1 (NLLGRFEL) (SEQ ID NO: 1). Therefore, it was assumed that the antibody shows cross-reactivity for Hsp70 in both species. The membrane Hsp70 phenotype was studied in several mouse tumor cell lines derived from different mouse strains. Among others, the mouse colon carcinoma cell line CT26 was found to be strongly membrane Hsp70 positive. Moreover, a temperature shift from 4° C. to 37° C. resulted in an internalization of the fluorescence-labelled cmHsp70.1 mAb. This result could be explained by a fast turnover rate of membrane-bound Hsp70 into the cytosol at physiological temperatures. The time-dependent and tumor-specific accumulation of the cmHsp70.1-FITC mAb in early endosomes and lysosomes further supports this hypothesis. In line with these findings it has been shown recently that Hsp70 associates with proteins such as MUC1 and caveolin 1 in lipid rafts of breast cancer cells [24]. These protein aggregates rapidly become endocytosed to re-enter the secretory pathway for recycling to the plasma membrane [25]. Co-staining of Hsp70 with the small GTPases Rab4 and Rab5a, which mark transport routes of proteins from the plasma membrane to early endosomes and back to the plasma membrane, also support this recycling pathway [26]. As expected, part of the intracellular located Hsp70 becomes degraded in lysosomes [26].

Given that the membrane Hsp70 positivity of CT26 tumors derived form mice autopsies was even greater than that of in vitro cultured CT26 cells, we addressed the question whether cmHsp70.1 mAb conjugated to different fluorophors also stains mouse tumors in vivo. Intraoperative and NIRF imaging techniques revealed a fast and highly specific binding of the Cy5.5-labelled cmHsp70.1 mAb to i.p. and s.c. localized tumors in living animals, as early as 30 min after i.v. injection into the tail vein which lasts for at least 96 h. In contrast, an identically labelled IgG1 isotype-matched control antibody was found to be enriched in the liver at the identical time frame. A detailed macro- and microscopical inspection of tumor-free organs of the mice showed that the cmHsp70.1 mAb did not bind to any normal mouse tissues. A non-specific up-take of antibody-free fluorescence dye into the tumor is unlikely since different cmHsp70.1-fluorophor conjugates produced identical results.

The tumor-specific binding pattern of mAb cmHsp70.1 was further confirmed by NIRF imaging of s.c. located tumors. In the tumor, the fluorescence signals of an identically labelled IgG1 isotype-matched control was significantly lower than that of the cmHsp70.1 mAb. By comparing the 3D flat-panel VCT data to the 2D fluorescence maps [21], generated by NIRF imaging, we successfully matched fluorescence signals from Cy5.5-labelled cmHsp70.1 mAb to pathologic tumor structures. Co-registration of fluorescence signals obtained by Optix to flat-panel VCT data illustrating anatomical sites, as described by Dullin et al. [21], might be useful for kinetic measurements of i.p. and orthotopically localized tumors in living animals. Since it has been shown that radiochemotherapy enhances the cell surface density of Hsp70 selectively in tumors but not in normal tissues [9,15], the Hsp70-specific antibody might serve as a tool for measuring the therapeutic outcome. Moreover, metastases in general exhibit elevated Hsp70 levels on their cell membranes, compared to primary tumors (unpublished data), and therefore might become detectable earlier by the use of cmHsp70.1 mAb.

Despite the IgG1 isotype of the cmHsp70.1 mAb, its capacity to induce ADCC against membrane Hsp70 tumor cells has been shown. Due to the rapid and tumor-selective uptake of the Hsp70 antibody, which is most likely mediated via a high turnover rate of membrane Hsp70 [27-29], it is conceivable that the anti-tumoral activity of cmHsp70.1 mAb can be further enhanced when applied as an antibody-drug or -radionuclide conjugate.

We have previously demonstrated that the incubation of lymphocytes with Hsp70 peptide "TKD" in the presence of low dose IL-2 results in an enhanced cytolytic and migratory capacity of NK cells towards membrane Hsp70 positive tumor cells in vitro (12) and in a xenograft tumor mouse model (20). The direct cytolytic effects of "TKD" peptide plus IL-2-activated NK cells against membrane Hsp70 positive mouse tumors were clearly detectable in the current study, as has previously been described for human tumors (12, 21-22). In a clinical phase I trial, the tolerability, feasibility and safety of adoptively transferred, autologous TKD/IL-2-activated NK cells has been shown in patients suffering from colorectal and lung carcinomas (21). Here, we show an improvement of the in vitro cytotoxic effects of TKD/IL-2-activated NK cells against membrane Hsp70 positive tumor cells by the addition of cmHsp70.1 mAb, which is most likely mediated by ADCC. The mode of killing of membrane Hsp70 CT26 tumor cells, as visualized in a movie, involves an enhanced migratory capacity of effector cells and a concerted attack of single tumor cells in the presence of cmHsp70.1 mAb. Two to three i.v. injections of relatively low amounts of unconjugated cmHsp70.1 mAb (20 μg per injection) into tumor-bearing mice resulted in a significant growth reduction of CT26 tumors which was accompanied by a massive infiltration of innate immune cells. The finding that the membrane Hsp70 positivity of CT26 tumors derived from mice autopsies was greater than that of in vitro cultured CT26 cells might explain the cmHsp70.1 mAb mediated ADCC effect.

We have also previously reported that membrane Hsp70 positive tumors actively release Hsp70 surface-positive lipid vesicles (23) which have the biophysical characteristics of exosomes (24, 25) and can attract activated, but not resting NK cells. In the current study we have determined a significant increase in circulating Hsp70 in mice showing inhibition of tumor growth. Whether this serum Hsp70 originates from tumor exosomes or from necrotic tumor material has not yet been elucidated. Furthermore, ongoing studies are evaluating whether the administration of low dose IL-2 into tumor-bearing mice might further improve the anti-tumoral effect of cmHsp70.1 mAb via the in vivo activation of mouse NK cells.

Radiochemotherapy has been shown to enhance the cell surface density of Hsp70 on tumors (10, 26-28). We therefore speculate that a combined approach consisting of an Hsp70 mAb-based immunotherapy which involves activated NK cells might provide a new strategy to improve the clinical outcome of patients after a standard radiochemotherapy or patients with distant metastases. These data are further supported by the clinical observation that a metastases-free survival rate can be associated with an enhanced NK cell activity (29). Remarkably, three consecutive i.v. injections of relatively low amounts of cmHsp70.1 mAb not only inhibited primary tumor growth within the first week after injection, but also significantly prolonged the life expectancy of mice bearing membrane Hsp70 positive CT26 tumors. The Hsp70 specificity of this approach is further supported by the finding that cmHsp70.1 mAb affected neither the tumor growth nor the life-expectancy of mice bearing membrane Hsp70 negative A20 B cell lymphomas. Moreover, a co-incubation of membrane Hsp70 positive tumors with an excess of "TKD" peptide plus cmHsp70.1 mAb not only blocks the antibody binding in vitro, but also completely reverses the anti-tumoral effect in vivo. These data confirm that the "TKD" peptide sequence represents the recognition site of cmHsp70.1 mAb, in vitro and in vivo.

References Mentioned in [ ] Brackets

1. Kampinga H H, Hagemann J, Vos M J, et al. Guidelines for the nomenclature of the human heat shock proteins. *Cell Stress Chaperones* 2009; 14: 105-11.
2. Ferrarini M, Heltai S, Zocchi M R, Rugarli C. Unusual expression and localization of heat-shock proteins in human tumor cells. *Int J. Cancer.* 1992; 51: 613-19.
3. Shin B K, Wang H, Yim A M, et al. Global profiling of the cell surface proteome of cancer cells uncovers an abundance of proteins with chaperone function. *J Biol. Chem.* 2003; 278: 7607-16.
4. Multhoff G, Botzler C, Wiesnet M, et al. A stress-inducible 72-kDa heat-shock protein (HSP72) is expressed on the surface of human tumor cells, but not on normal cells. *Int J. Cancer.* 1995; 61: 272-9.
5. Botzler C, Li G, Issels R D, Multhoff G. Definition of extracellular localized epitopes of Hsp70 involved in an NK immune response. *Cell Stress Chaperones.* 1998; 3: 6-11.
6. Multhoff G, Pfister K, Gehrmann M, et al. A 14-mer Hsp70 peptide stimulates natural killer (NK) cell activity. *Cell Stress Chaperones.* 2001; 6: 337-44.
7. Hantschel M, Pfister K, Jordan A, et al. Hsp70 plasma membrane expression on primary tumor biopsy material and bone marrow of leukemic patients. *Cell Stress Chaperones.* 2000; 5: 438-42.
8. Kleinjung T, Arndt O, Feldmann H J, et al. Heat shock protein 70 (Hsp70) membrane expression on head-and-neck cancer biopsy-a target for natural killer (NK) cells. *Int J Radiat Oncol Biol Phys.* 2003; 57: 820-6.
9. Farkas B, Hantschel M, Magyarlaki M, et al. Heat shock protein 70 membrane expression and melanoma-associated marker phenotype in primary and metastatic melanoma. Melanoma Res. 2003; 13: 147-52.
10. Pfister K, Radons J, Busch R, et al. Patient survival by Hsp70 membrane phenotype: association with different routes of metastasis. Cancer. 2007; 110: 926-35.
11. Gehrmann M, Radons J, Molls M, Multhoff G. The therapeutic implications of clinically applied modifiers of heat shock protein 70 (Hsp70) expression by tumor cells. *Cell Stress Chaperones.* 2008; 13: 1-10.
12. Gehrmann M, Liebisch G, Schmitz G, et al. Tumor-specific Hsp70 plasma membrane localization is enabled by the glycosphingolipid Gb3. *Plos One.* 2008. DOI: 10.1371/j.0001925.
13. Falguieres T, Maak M, von Weyhern C, et al. Human colorectal tumors and metastases express Gb3 and can be targeted by an intestinal pathogen-based delivery tool. *Mol. Cancer Ther.* 2008; 7: 2498-508.
14. Schilling D, Gehrmann M, Steinem C, et al. Binding of Hsp70 to extracellular phosphatidylserine promotes killing of normoxic and hypoxic tumor cells. *FASEB J* 2009; 23: 2467-77.
15. Vega V, Rodriguez-Silva M, Frey T, et al. Hsp70 translocates into the plasma membrane after stress and is released into the extracellular environment in a membrane-associated form that activates macrophages. *J Immunol.* 2008; 180: 4299-307.
16. Arispe N, Doh M, Simakova O, et al. Hsc70 and Hsp70 interact with phosphatidylserine on the surface of PC12 cells resulting in a decrease of viability. *FASEB J.* 2004; 18: 1636-45.
17. Gehrmann M, Marienhagen J, Eichholtz-Wirth H, et al. Dual function of membrane-bound heat shock protein 70 (Hsp70), Bag-4, and Hsp40: protection against radiation-induced effects and target structure for natural killer cells. *Cell Death Differ.* 2005; 12: 38-51.
18. Dullin C, Zientkowska M, Napp J, et al. Semiautomatic landmark-based two-dimensional-three-dimensional image fusion in living mice: correlation of near-infrared fluorescence imaging of Cy5.5-labelled antibodies with flat-panel volume computed tomography. *Mol Imaging.* 2009; 8: 2-14.
19. Wang M, Bronte V, Chen P W, et al. Active immunotherapy of cancer with a non-replicating recombinant fowlpox virus encoding a model tumor-associated antigen. *J Immunol.* 1995; 154: 4685-92.
20. Kim K J, Kanellopoulos-Langevin C, Merwin R M, et al. Establishment and characterization of BALB/c lymphoma lines with B cell properties. *J Immunol.* 1979; 122: 549-54.
21. Missbach-Guentner J, Dullin C, Kimmina S, et al. Morphological changes of mammary carcinomas in mice over time as monitored by flat-panel detector volume computed tomography. *Neoplasia.* 2008; 10: 663-73.
22. Zhang H, Liu R, Huang W. A 14-mer peptide from HSP70 protein is the critical epitope which enhances NK activity against tumor cells in vivo. *Immunol Invest.* 2007; 36: 233-46.

23. Broquet A H, Thomas G, Masliah J, et al. Expression of the molecular chaperone Hsp70 in detergent resistant microdomains correlates with its membrane expression and release. *J Biol Chem.* 2003; 278: 21601-6.
24. Staubach S, Razawi H, Hanisch F G. Proteomics of MUC1-containing lipid rafts from plasma membranes and exosomes of human breast carcinoma cells MCF-7. *Proteomics.* 2009; 9: 2820-35
25. Gastpar R, Gehrmann M, Bausero M, et al. Hsp70 surface-positive tumor exosomes stimulate migratory and cytolytic activity of NK cells. *Can Res.* 2005; 65: 5238-47.
26. Stenmark H. Rab GTPases as coordinators of vesicle traffic. *Nature Rev Mol Cell Biol.* 2009; 10: 513-25.
27. Adams G P, Weiner L M. Monoclonal antibody therapy of cancer. *Nat Biotechnol.* 2005; 23: 1147-57.
28. Scallon B J, Snyder L A, Anderson G M, et al. A review of antibody therapeutics and antibody-related technologies for oncology. *J Immunother.* 2006; 29: 351-64.
29. Bonner J A, Harari P M, Giralt J, et al. Radiotherapy plus cetuximab for squamous-cell carcinoma of the head and neck. *N Engl J Med.* 2006; 354: 567-78.

References Mentioned in ( ) Brackets
1. Adams G P, Weiner L M (2005) Monoclonal antibody therapy of cancer. *Nat Biotechnol* 23:1147-1157.
2. Scallon B J, et al. (2006) A review of antibody therapeutics and antibody-related technologies for oncology. *J Immunother* 29:351-364.
3. Bonner J A, et al. (2006) Radiotherapy plus cetuximab for squamous-cell carcinoma of the head and neck. *N Engl J Med* 354:567-578.
4. Edwards J C, et al. (2004) Efficacy of B-cell-targeted therapy with rituximab in patients with rheumatoid arthritis. *N Engl J Med* 350:2572-2581.
5. Ferrarini M, Heltai S, Zocchi M R Rugarli C (1992) Unusual expression and localization of heat-shock proteins in human tumor cells. *Int J Cancer* 51:613-619.
6. Shin B K, et al. (2003) Global profiling of the cell surface proteome of cancer cells uncovers an abundance of proteins with chaperone function. *J Biol Chem* 278:7607-7616.
7. Multhoff G, et al. (1995) A stress-inducible 72-kDa heat-shock protein (HSP72) is expressed on the surface of human tumor cells, but not on normal cells. *Int J Cancer* 61:272-279.
8. Hantschel M, et al. (2000) Hsp70 plasma membrane expression on primary tumor biopsy material and bone marrow of leukemic patients. *Cell Stress Chaperones* 5:438-442.
9. Pfister K, et al. (2007) Patient survival by Hsp70 membrane phenotype: association with different routes of metastasis. *Cancer* 110:926-935.
10. Gehrmann M, et al. (2005) Dual function of membrane-bound heat shock protein 70 (Hsp70), Bag-4, and Hsp40: protection against radiation-induced effects and target structure for natural killer cells. *Cell Death Differ* 12:38-51.
11. Fouchaq B, Benaroudj N, Ebel C Ladjimi M M (1999) Oligomerization of the 17-kDa peptide-binding domain of the molecular chaperone HSC70. *Eur J Biochem* 259:379-384.
12. Multhoff G, et al. (2001) A 14-mer Hsp70 peptide stimulates natural killer (NK) cell activity. *Cell Stress Chaperones* 6:337-344.
13. Stangl S, et al. In vivo imaging of CT26 mouse tumors by using cmHsp70.1 monoclonal antibody. *J Cell Mol. Med.*
14. Horvath I, Vigh L (2010) Cell biology: stability in times of stress. *Nature* 463:436-438.
15. Horvath I, Multhoff G, Sonnleitner A Vigh L (2008) Membrane associated stress proteins: more than simply chaperones. *Biochim Biophy Acta (BBA)* 1778: 1653-1664.
16. Zhang H, Liu R Huang W (2007) A 14-mer peptide from HSP70 protein is the critical epitope which enhances NK activity against tumor cells in vivo. *Immunol Invest* 36:233-246.
17. Wang M, et al. (1995) Active immunotherapy of cancer with a nonreplicating recombinant fowlpox virus encoding a model tumor-associated antigen. *J Immunol* 154:4685-4692.
18. Steplewski Z, Lubeck M D Koprowski H (1983) Human macrophages armed with murine immunoglobulin G2a antibodies to tumors destroy human cancer cells. *Science* 221:865-867.
19. Houghton A N, et al. (1985) Mouse monoclonal IgG3 antibody detecting GD3 ganglioside: a phase I trial in patients with malignant melanoma. *Proc Natl Acad Sci USA* 82:1242-1246.
20. Stangl S, Wortmann A, Guertler U Multhoff G (2006) Control of metastasized pancreatic carcinomas in SCID/beige mice with human IL-2/TKD-activated NK cells. *J Immunol* 176:6270-6276.
21. Krause S W, et al. (2004) Treatment of colon and lung cancer patients with ex vivo heat shock protein 70-peptide-activated, autologous natural killer cells: a clinical phase I trial. *Clin Cancer Res* 10:3699-3707.
22. Milani V, et al. (2009) Anti-tumor activity of patient-derived NK cells after cell-based immunotherapy—a case report. *J Transl Med* 7:50.
23. Gastpar R, et al. (2005) Heat shock protein 70 surface-positive tumor exosomes stimulate migratory and cytolytic activity of natural killer cells. *Cancer Res* 65:5238-5247.
24. Bausero M A, Gastpar R, Multhoff G Asea A (2005) Alternative mechanism by which IFN-g enhances tumor recognition: active release of heat shock protein 72. *J Immunol* 175:2900-2912.
25. Lancaster G I, Febbraio M A (2005) Exosome-dependent trafficking of HSP70: a novel secretory pathway for cellular stress proteins. *J Biol Chem* 280:23349-23355.
26. Gehrmann M, Radons J, Molls M Multhoff G (2008) The therapeutic implications of clinically applied modifiers of heat shock protein 70 (Hsp70) expression by tumor cells. *Cell Stress Chaperones* 13:1-10.
27. Kleinjung T, et al. (2003) Heat shock protein 70 (Hsp70) membrane expression on head-and-neck cancer biopsy-a target for natural killer (NK) cells. *Int J Radiat Oncol Biol Phys* 57:820-826.
28. Farkas B, et al. (2003) Heat shock protein 70 membrane expression and melanoma-associated marker phenotype in primary and metastatic melanoma. *Melanoma Res* 13:147-152.
29. Kondo E, et al. (2003) Preoperative natural killer cell activity as a prognostic factor for distant metastasis following surgery for colon cancer. *Dig Surg* 20:445-451.
30. Frank R (2002) The SPOT-synthesis technique. Synthetic peptide arrays on membrane supports—principles and applications. *J Immunol Methods* 267:13-26.
31. Dressel R, Johnson J P Gunther E (1998) Heterogeneous patterns of constitutive and heat shock induced expression of HLA-linked HSP70-1 and HSP70-2 heat shock genes in human melanoma cell lines. *Melanoma Res* 8:482-492.
32. Kim K J, Kanellopoulos-Langevin C, Mervin R M, Sachs D H Asofsky R (1979) Establishment and characterization of BALB/c lymphoma lines with B cell properties. *J Immunol* 122:549-554.
33. Nishioka Y, et al. (1997) Combined therapy of multidrug-resistant human lung cancer with anti-P-glycoprotein antibody and monocyte chemoattractant protein-1 gene transduction: the possibility of immunological overcoming of multidrug resistance. *Int J Cancer* 71:170-177.

34. Kaplan E, Meyer P (1958) Nonparametric estimation from incomplete observations. *J Am Stat Assoc* 53:457-481.

The invention claimed is:

1. A method of inhibiting growth of tumor cells expressing an extracellular localized epitope of membrane-bound heat shock protein 70 (Hsp70) on the cell surface comprising contacting said tumor cells with a therapeutically effective amount of a monoclonal antibody that binds to an extracellular localized epitope of Hsp70 on tumor cells, wherein said epitope consists of the amino acid sequence of SEQ ID NO: 1 or SEQ ID NO: 2.

2. A method of inhibiting growth of tumor cells expressing an extracellular localized epitope of membrane-bound heat shock protein 70 (Hsp70) on the cell surface comprising contacting said tumor cells with a therapeutically effective amount of a bi- or multifunctional molecule comprising a) an antibody, an immunoglobulin chain or an antigen-binding fragment thereof, that binds to an extracellular localized epitope of Hsp70 on tumor cells, wherein said epitope consists of the amino acid sequence of SEQ ID NO: 1 or SEQ ID NO: 2 and wherein said antibody is the monoclonal antibody cmHsp70.1 as produced by hybridoma cmHsp70.1, deposited with the DSMZ-Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or cmHsp70.2 as produced by hybridoma cmHsp70.2, deposited with the DSMZ-Deutsche Sammlung von Mikroorganismen und Zellkulturen GmbH, Mascheroder Weg 1b, D-38124 Braunschweig, Germany on Nov. 14, 2003, and assigned Accession Number DSM ACC2630; and b) at least one further functional domain selected from the group consisting of a cytotoxic domain and a binding domain, said binding domain is specific for an epitope on a cell surface antigen selected from the group consisting of cytokine and lymphokines receptors, Fc receptors, CD3, CD16, CD28, CD32, CD64, and CD94.

3. The method of claim 1 or claim 2, wherein said tumor cells is contacted with said antibody or said bi- or multifunctional molecule by administration via a route selected from the group consisting of intravenous administration, intramuscular administration, subcutaneous administration, intraperitoneal administration and administration via an aerosol.

4. The method of claim 1, wherein said monoclonal antibody is cmHsp70.1 as produced by hybridoma cmHsp70.1, deposited with the DSMZ-Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or cmHsp70.2 as produced by hybridoma cmHsp70.2, deposited with the DSMZ-Deutsche Sammlung von Mikroorganismen und Zellkulturen GmbH, Mascheroder Weg 1b, D-38124 Braunschweig, Germany on Nov. 14, 2003, and assigned Accession Number DSM ACC2630.

5. The method of claim 1, wherein said antibody is a human, humanized, xenogeneic, or a chimeric human-murine antibody.

6. The method of claim 2, wherein said antigen-binding fragment is selected from the group consisting of a single chain Fv fragment, and F(ab') fragment, an F(ab) fragment, and an F(ab')2 fragment 7. The method of claim 2, wherein the bi- or multifunctional molecule is a bispecific molecule.

8. A method of targeting a therapeutic agent to a tumor cell in a subject, wherein said tumor cell expresses an extracellular localized epitope of membrane-bound heat shock protein 70 (Hsp70) on the cell surface, wherein said epitope consists of the amino acid sequence of SEQ ID NO: 1 or SEQ ID NO: 2, comprising administering to the subject a therapeutically effective amount of the bi- or multifunctional molecule of claim 2.

9. A method of targeting a diagnostic agent to a tumor cell which expresses an extracellular localized epitope of membrane-bound heat shock protein 70 (Hsp70) on the cell surface, wherein said epitope consists of the amino acid sequence of SEQ ID NO: 1 or SEQ ID NO: 2, comprising administering to the subject the bi- or multifunctional molecule of claim 2 conjugated to a diagnostic agent.

* * * * *